(12) United States Patent
Hori

(10) Patent No.: US 8,399,240 B2
(45) Date of Patent: Mar. 19, 2013

(54) METHOD AND GENE FOR PROVIDING OR ENHANCING NONSPECIFIC ADHESIVE PROPERTY AND/OR AUTOAGGLUTINATING PROPERTY FOR MICROORGANISMS

(75) Inventor: Katsutoshi Hori, Aichi (JP)

(73) Assignee: National University Corporation Nagoya University, Aichi (JP)

( * ) Notice: Subject to any disclaimer, the term of this patent is extended or adjusted under 35 U.S.C. 154(b) by 285 days.

(21) Appl. No.: 12/918,547

(22) PCT Filed: Feb. 22, 2008

(86) PCT No.: PCT/JP2008/053591
§ 371 (c)(1),
(2), (4) Date: Aug. 20, 2010

(87) PCT Pub. No.: WO2009/104281
PCT Pub. Date: Aug. 27, 2009

(65) Prior Publication Data
US 2011/0045529 A1 Feb. 24, 2011

(51) Int. Cl.
*C12N 1/20* (2006.01)
*C12P 1/00* (2006.01)
(52) U.S. Cl. .................. 435/252.3; 435/41; 435/252.33
(58) Field of Classification Search ........................ None
See application file for complete search history.

(56) References Cited

PUBLICATIONS

Labigne-Roussel, et al. (Infection and Immunity, Oct. 1984, p. 251-259).*
Takada, Shuhei et al., "Molecular Analysis of the Adhesive Nanofiber of a Highly Adhesive Gram-Negative Bacterium"; The Division of Biotechnology, the Chemical Society of Japan, Aug. 24, 2007, pp. 1-5.
Hori, Katsutoshi "Clarification and Industrial Applicability of Adhesion Mechanisms" (Partial Translation); Fundamentals and Control of Biofilms, Feb. 4, 2008, pp. 1-18.
Bullard, Brian et al. "Regions Important for the Adhesion Activity of Moraxella Catarrhalis Hag"; BMC Microbiology, vol. 7, 2007, pp. 65-77; www.biomedcentral.com/1471-2180/7/65.
Takada, Shuhei, et al., "Analysis of Adhesive Gene of Highly Adhesive Bacteria *Acinetobacter* sp. Tol 5"; (Abstract No. 30F030), The Society of Chemical Engineers, Japan, Aug. 13, 2007, pp. 1-6.
Ishikawa, Masahito, et al., "Molecular Analysis of a Novel Bacterial Adhesin"; (Abstract No. 3E12-3), The Society for Biotechnology, Japan, Aug. 2, 2007, pp. 1-4.
Takada, Shuhei, et al., "Analysis of the Adhesin Gene in *Acinetobacter* sp. Tol 5"; (Abstract No. 2H11-1), The Society for Biotechnology, Japan, Aug. 3, 2006, pp. 1-3.

Hori, Katsutoshi, et al., "Highly Adhesive Bacterial Cell Nanofiber and Adhesion Properties Thereof"; (Abstract No. H306), Society of Chemical Engineers, Japan, Feb. 19, 2007, pp. 1-5.
Hori, Katsutoshi, et al., "Nanofiber and Adhesive Protein of Highly-Adhesive Bacteria, *Acinetobacter* sp. Tol 5", (Abstract No. 3A08p19), Japan Society for Bioscience, Biotechnology, and Agrochemistry, Mar. 5, 2007, pp. 1-3.
Ishii, Shun'ichi, et al., "Effect of Cell Appendages on the Adhesion Properties of a Highly Adhesive Bacterium, *Acinetobacter* sp. Tol 5"; Bioscience, Biotechnology, Biochemistry, 70, (11), 2006, pp. 2635-2640.
Higuchi, Aisuke, et al., "Formation of Adhesive Nanofibers on *Acinetobacter* sp. Tol 5 Cells" (Abstract No. 3C11-5), The Society for Biotechnology, Japan, Aug. 2, 2007, pp. 1-3.
Ishii, Shun'ichi, et al., "Formation of Filamentous Appendages by *Acinetobacter* sp. Tol 5 for Adhering to Solid Surfaces", Journal of Bioscience and Bioengineering, 2008, vol. 105, No. 1, pp. 20-25.
Hori, Katsutoshi, et al., "Monolayer Adsorption of a "Bald" Mutant of the Highly Adhesive and Hydrophobic Bacterium *Acinetobacter* sp. Strain Tol 5 to a Hydrocarbon Surface", Applied and Environmental Microbiology, 2008, vol. 74, No. 8, pp. 2511-2517.
Tomaras, Andrew P., et al., "Attachment to and Biofilm Formation on Abiotic Surfaces by *Acinetobacter baumannii*: Involvement of a Novel Chaperone-Usher Pili Assembly System", Microbiology, 2003, vol. 149, pp. 3473-3484.
Gospodarek, E., "Adhesion of *Acinetobacter calcoaceticus* to Cheek Epithelial Cells", Medycyna Doswiadczalna i Mikrobiologia, 1994, vol. 46 (1-2), pp. 19-23 (Abstract Only).
Boujaafar N., et al., "Cell Surface Hydrophobicity of 88 Clinical Strains of *Acinetobacter baumannii*", Research in Microbiology, 1990, vol. 141, pp. 477-482.
MacIntyre D. E., "Endotoxin-Induced Platelet Aggregation and Secretion I. Morphological Changes and Pharmacological Effects", Journal of Cell Science, 1977, vol. 28, pp. 211-223 (Abstract Only).
Roux, Agnes, et al., "Combined Inactivation and Expression Strategy to Study Gene Function Under Physiological Conditions: Application to Identification of New *Escherichia coli* Adhesins", Journal of Bacteriology, Feb. 2005, vol. 187, No. 3, pp. 1001-1013.
Dams-Kozlowska, H. and Kaplan D., XP002631866, EMBL AC: EU 086055, Aug. 28, 2007, 3 Pages.
Riess, T, et al., XP002631867, EMBL AC: DQ665674, Dec. 23, 2006, 5 Pages.
Capecchi, Barbara, et al., "*Neisseria meningitidis* NadA Is a New Invasion Which Promotes Bacterial Adhesion to and Penetration Into Human Epithelial Cells", Molecular Microbiology, 2005, vol. 55, No. 3, pp. 687-698.

* cited by examiner

*Primary Examiner* — Suzanne M Noakes
*Assistant Examiner* — Jae W Lee
(74) *Attorney, Agent, or Firm* — McCarter & English

(57) ABSTRACT

A method for providing or enhancing a nonspecific adhesive property, an autoagglutinating property, or both properties in a microorganism is provided. The method comprises introducing a nucleic acid encoding autotransporter adhesin from a microorganism having a nonspecific adhesion property into a target microorganism.

12 Claims, 16 Drawing Sheets

Fig. 2

```
GTTAACGCAAGTTGTTTTACTGCTGAAGCTGTCAATTTTTGTCCACGACCTGACTTACGGTCCGGTTGAGTATACACAGCGACGATTTCGTGGT
CAGTTTGAATCAGTGCTGCTAATGCTGAAGCTGCAAATTCGGGTGTGCCTGCAAAAATGATCTTCAAAGGTTGTGCTCAGATTAAATTTTAAAG
TCAATTATAGCAAACATGGTTCTATGGTGGGATTTTCAAATGAAAATTTGATTTTCTCCAAATGTGAAAATTAATTATATTATTTTGACACAAA
GCTATTTATTTATGATTTTGACGTATCTATAGATCTGATATGTTTCTTTTGATTAATGAATTTGATGATATTTTGATCGCAGTATGGGTGATAT
TAAAAAATAATGTGATTTAAATCACATTTAATAGACTATGTTTTATAAAAATTAGAATCATTTTTCAGAGTATGGTTTCTTACATATTGAAATA
ATGATCTGTTTTTTTGTGTTTTGTAAAGTTTTTCTAAACAAAATTAATAAATATTACTCAGAAAAAACACAAAGTAGTGAAAGATAAAAATAAAA
AGCTATTAAGAAAAATTGTAAACACAAAGAATGTAAACTTAATAAAAATATAATTTTGAGGAATGAGTCACACTTATTTTTAACAAATGTGACAA
AATTTGTCACATAATTAATTAGAAATAATGTGATTTTAGTAAAACTTTACAATACTGAGGATAAATATAACTCTATGTTTTTAAATGTAAAAT
ATTAAAAAATGTAAAATAATATAGCTTAATTTCAAAAAAATTAAACCAATTGGTTTAAAAGTTAAAAAAAGTGAAATATATCTCATTTTTTTGAT
TGCTTTAATTGTATGTAAATTGTTAAATAAAAAAAAATTGTACATTTTATATGCATTGCTAAAGCAGAACCTACTGCCCAAAATGCATCTCCTA
AGGAAAAGCGATATGAATAAAATCTACAAAGTGATTTGGAATGCGACTTTGTTGGCATGGGTTGCAGTATCTGAATTGGCAAAAGGGAAAACCA
AATCTACGACATCAAAATCCAAAGCTAAATCATTATCTTCATCTGTAATAGTTGGTGGGATAATATTAACAACACCTTTATCTTTAATAGCAGC
TACTGTTCAAGTTGGAGGGGGAACTAATTCTGGAACAACTGCTACAGCTTCTACGAATTGTGCAGACTTATATAATTATCAAAATCCTGAGAAC
TCAGGCTCTGGAGCGGCTGGGAATTATAATGCAGGAAATCCAAGTGTGTGTTCGATCGCTATAGGTGAAAACGCACAAGGTGGTACTTCTGGAA
CTGGAGGGTCGCCAGGGATAGCGATAGGTGGAAATTCTAAAGCTACGGGTGGTTTATCTGTTGCTATAGGCGGATATGCTCAAGCGACAAATGT
TGGAAGTATTGCTTTAGGCACAGCAGCTTTATCAAGTGGTTTTAACAGTTTAGCAATATCCAGACAAGCTGCTGCAACGAATAACTATTCAATA
GCTATAGGTACAACTTCAGTTTCGAAAGGAGTTGGATCGATTGCTATGGGGCATTCAACGAATGCTTCTGGAGATCAATCGATAGCAATTGGTA
GCTCGGATGCTGTTAATTCAGCAACAGCAACAACAACATACGATGGTACAACAAATACTCAAGCATCAGGTAGTAAATCGATTGCTATAGGTGC
AAGCGCAAAGGCATCAACCAATAACAGCATTGCACTAGGTGCAGGATCGGTAACTTCTGCACAATCTGGTAATTCTTATCTTACTGGTGTAGGT
GCATCAGCTACAAATGGTGTTGTATCTGTTGGAACTTCAACTGCAACACGTCGTATCCAAAATGTAGCAGATGGTTCAGCCGCTTCAGATGCTG
TGACAGTTGCTCAGTTGGATAAAGCTTATGATGATACAAATGGTCGTTTAGCTGCTGCTTTAGGTACAGGTAGTGGTGCTGCCTATAATGCAGC
AAACAATACATATACCGCTCCAACGAATATTGGGGGAACAGGTAAAAATACGATTGATGATGCAATTAAAGCAACTCAACGAAGTGTAGTCGCT
GGATCAAATATTGTCGTTACCCCGACGACAGCTTCTGATGGTTCAATATCGTATTCGGTTGCTACAAGCGCAACACCGACGTTTACAAGTATAA
CTGTAAACAATGCACCAACGGCAGGTACAGATGCGACCAACAAGACTTATGTAGACTCAAAAGCAGCAGCATCGAGAACAGAAGTAGCAGCTGG
AAGCAATGTATCTGGTGTAGTAAAAACGACAGGCGCAAACGGTCAAGACGTTTATACAGTAAATGCCAATGGTACGACTGCATCAGCAGGTTCT
TCAGCAGTTACCGTAACACCAGGCACGAAAGATGCAAATAATGTCACTGACTATAAAGTAGACTTATCAGCGACTACAAAAACCGATATCCAAA
AAGGTGTAGATGCAAAAAATGCTGTAGATACCGCAGGTCTAAAATTTAAAGGTGATACAGCAACCACAAGCAATACCAAGAAATTAGGTGACAC
CGTTTCGATTACGGGTGATACGAACATTAGTACAGTTGCGACAACAGATGGTGTACAGGTTAAGTTAAATCCAAACTTGGATTTAGGAGCAACT
GGTAGCGTTAAAACGGGTAATACCACGATTAACAATGCAGGTGTAACAGCTGATCAAGTTACGGTTGGTGGTGTTGTTATTAACAACACATCAG
GTATTAATGCTGGTGGTAAAGCGATTACTAATGTAGCAGCACCAACAAATAACACAGATGCTGCTAACAAGAAGTATGTAGATGATGCAGGTAC
AGCATTAACCAATTTGGGCTTTGGATTAAAAGCACAAGATGGTACGACTGTGAACAAGAAATTAGGTGAAGCAGTTGATATTGTTGGTTCAAAC
AGCAACATCAGTACAAAAGTAAATGCAGGCAAAGTAGAAGTTGCACTATCCAATACATTGGACTTAGGTACTACAGGTAGCGTTACTACGGGTT
CAACTGTAATTAACAATACTGGTGTTACGGCAACTCAGGTTACCGCAAACAAAGTCACAATAAACAATGCACCAACAGCAGGTACAGATGCGAC
CAACAAGACTTATGTAGACTCAAAAGCAGCAGCATCAAGAACAGAAGTCGCAGCTGGAAGCAATGTATCTGGTGTAGTAAAAACGACAGGCGCA
AACGGTCAAGATATTTATGCAGTAAATGCCAATGGTACGACTGCATCAGCAGGTTCTTCAGCAGTTACCGTAACACCAGGCACGAAAGATGCAA
ATAATGTCACTGACTATAAAGTAGACTTGTCAGCGACTACAAAAACCGATATTCAAAAAGGTGTAGATGCAAAAAATGCTGTAGATACTGCAGG
TCTAAAATTTAAAGGTGATACAGCAACCACAAGCAATACCAAGAAATTAGGTGACACCGTTTCGATTACGGGTGATACGAACATTAGTACAGTT
GCAACAACTGATGGTGTACAGGTTAAGTTAAATCCAAACTTAGATTTAGGAGCAACTGGTAGCGTTAAAACGGGTAATACCACGATTAACAATG
CAGGTGTAACAGCTGACCAAGTTACGGTTGGTGGTGTTGTTATTAACAACACATCAGGTATTAATGCTGGTGGTAAAGCGATTACCAATGTAGC
AGCACCAACAAATAACACAGATGCTGCTAACAAGAAGTATGTAGATGACGCAGGTACAGCATTAACCAATTTGGGCTTTGGATTAAAAGCGCAA
GATGGTACGACTGTGAACAAGAAATTAGGTGAAGCAGTTGATATTGTTGGTTCAAACAGCAACATCAGTACAAAAGTAAATGCAGGCAAAGTAG
AAGTTGCACTATCCAATACATTGGACTTAGGTACTACAGGTAGCGTTACTACGGGTTCAACTGTAATTAACAATGCTGGTGTTACGGCAACTCA
AGTTACCGCAAACAAAGTCACAGTTAATAATGCACCAACAGCAGGTACAGATGCGACCAATAAAACTTATGTAGACTCAAAAGCAGCGGCATCA
AGAACAGAAGTCGCAGCTGGAAGCAATGTATCTGGCGTAGTAAAAACGACAGGTGCAAACGGTCAAGACGTTTATACAGTAAATGCCAATGGTA
CGACTGCATCAGCAGGTTCTTCAGCAGTTACCGTAACACCAGGCACGAAAGATGCAAATAATGTCACTGACTATAAAGTAGACTTGTCAGCGAC
```

Fig. 2 (continued)

```
TACAAAAACCGATATTCAAAAAGGTGTAGATGCAAAAAATGCTGTAGATACCGCAGGTCTAAAATTTAAAGGTGATACAGCAACCACAAGCAAT
ACCAAGAAATTAGGTGACACCGTTTCGATTACGGGTGATACGAACATTAGTACAGTTGCGACAACTGATGGTGTACAGGTTAAGCTAAATCCAA
ACTTGGATTTAGGAGCAACTGGTAGCGTTAAAACGGGTAATACCACGATTAACAATGCAGGTGTAACAGCTGATCAAGTTACAGTTGGTGGTGT
TGTTATTAACAACACATCAGGTATTAATGCTGGTGGTAAAGCGATTACCAATGTAGCAGCACCAACAAATAACACAGATGCTGCTAACAAGAAG
TATGTAGATGATGCAGGTACAGCATTAACCAATTTGGGCTTTGGATTAAAAGCGCAAGATGGTACGACTGTGAACAAGAAATTAGGCGAAGCAG
TTGAAGTTGTTGGTGCGGACAGTAACATCACCACGAAAGTTGCAGGCGGTCAGGTTGCAATTGAGTTAAATAAAAACCTCAACAACTTAACTGG
CATTACCGTGAACGATGGAACCAATGGCACCAATGGTTCAACTGTGATTGGTAAAGATGGTATTTCGGTTAAAGATGGTTCAGGCAATACCATT
GCAGGTGTAGATAACACAGCGTTGACAGTTAAAGATGGCAGTGGCAACACAGAAACCAGCATTAACCAAGCGATCAACACGTTAAATGCAGCGC
AAGGTGAAACTGATAAGTTTGCAGTGAAGTACGACAAAAATGCTGATGGCAGTGTGAACTACAACAACATCACATTGGCAGGTACGACTGCAAG
CAGTACACAAGATGCAACTACAGGCAAGATCACCACAACAGGTGGAACAAGCTTGAACAATGTTGCAAGTGCGGGTGACTACAAAGATGTTGCC
AATGCAAGCAAAGGTGTAAACGCAGGTGACTTAAACAATGCAGTTGTTGATGCAACCAATGCAGCAACCAGCAAAGGCTTTGCATTACAAGCAG
CAGATGGCGCTAAAGTTCAGAAGAACCTAGGCGAAGCAGTTGAAGTTGTCGGTGCCGACAGCAACATCACCACAAAAGTTGCAGGCGGTCAGGT
TGCAATTGAGTTAAATAAAAACCTCAACAACTTAACTGGCATTACCGTGAACGATGGAACCAATGGCACCAATGGTTCAACTGTGATTGGTAAA
GATGGTATTTCAGTTAAAGACGGTTCAGGCAATACCATTGCAGGTGTAGATAACACAGCGTTGACAGTTAAAGATGGCAGTGGCAACACAGAAA
CCAGCATTAACCAAGCGATCAACACGTTAAATGCAGCGCAAGGTGAAACTGATAAGTTTGCAGTGAAGTACGACAAAAATACGGATGGTAGTAC
CAACTACAACAGTATTACTGCAGGCAATGGTAACGGTACTGCAGCAACGATCGGAACTGACACAGCAGGTAATAGTGTTGTGACCAGTGGCGGA
ACTAAAATTAGTAATGTTGCGAATGGTGTCAATGCAAGTGATGCAGTAAACAAAGGTCAATTGGATAGCTTAAGTACAGGTCTTACCAATACAG
GCTTTGGTTTAAAAGCAGCAGATGGCAACACCGTTAACAAAAAATTAGGCGAAGCAGTAGACGTTGTCGGTGCTGACAGCAACATCACCACGAA
AGTTGCAGGCGGTCAGGTTGCGATTGAGTTAAATAAAAACCTCAACAACTTAACTGGCATTACCGTGAACGATGGAACCAATGGCACCAATGGT
TCAACTGTGATTGGTAAAGATGGTATTTCGATTAAAGATGGTTCAGGCAATACCATTGCAGGTGTAGATAACACAGCGTTGACAGTTAAAGATG
GCAGTGGCAACACAGAAACCAGCATTAACCAAGCGATCAACACGTTAAATGCAGCGCAAGGTGAAACTGACAAGTTTGCAGTGAAGTACGACAA
GAATGCTGATGGCAGTGCAAACTACAACAACATCACATTGGCAGGTACGACTGCAAGTAGCACGCAAGATGCAACAACAGGCAAGATCACCACA
ACAGGTGGAACAAGCTTGAACAACGTTGCAAGTGCAGGTGACTACAAAGATGTTGCCAATGCAAGCAAAGGTGTAAACGCAGGTGACTTGAACA
ATGCAGTTGTTGATGCAACCAATGCAGCAACCAGCAAAGGCTTTGCATTACAAGCAGCAGATGGCGCTAAAGTTCAGAAGAACCTAGGCGAAGC
AGTTGAAGTTGTCGGTGCGGACAGCAACATCACCACAAAAGTAGTGGGTGGACAAGTTGCGATTGAGTTAAATAAAAACCTCAACAACTTAACT
GGCATTACCGTGAACGATGGAACCAATGGCACAAATGGTTCAACTGTGATTGGTAAAGATGGTATTTCGGTTAAAGATGGTTCAGGTAATACCA
TTGCAGGTGTAGATAACACAGCGTTGACAGTTAAAGATGGCAGTGGCAACACAGAAACCAGCATTAACCAAGCGATCAACACGTTAAATGCAGC
GCAAGGTGAAACTGATAAGTTTGCAGTGAAGTACGACAAAAATGCTGATGGCAGTGTGAACTACAACAACATCACATTGGCAGGTACGACTGCA
AGCAGTACACAAGATGCAACTACAGGCAAGATCACCACAACAGGTGGAACAAGCTTGAACAATGTTGCAAGTGCGGGTGACTACAAAGATGTTG
CCAATGCAAGCAAAGGTGTAAACGCAGGTGACTTAAACAATGCAGTTGTTGATGCAACCAATGCAGCAACCAGCAAAGGCTTTGCATTACAAGC
AGCAGATGGCGCTAAAGTTCAGAAGAACCTAGGCGAAGCAGTTGAAGTTGTCGGTGCCGACAGCAACATCACCACAAAAGTTGCAGGCGGTCAG
GTTGCAATTGAGTTAAATAAAAACCTCAACAACTTAACTGGCATTACCGTGAACGATGGAACCAATGGCACCAATGGTTCAACTGTGATTGGTA
AAGATGGTATTTCAGTTAAAGACGGTTCAGGCAATACCATTGCAGGTGTAGATAACACAGCGTTGACAGTTAAAGATGGCAGTGGCAACACAGA
AACCAGCATTAACCAAGCGATCAACACGTTAAATGCAGCGCAAGGTGAAACTGATAAGTTTGCAGTGAAGTACGACAAAAATGCTGATGGCAGT
GTGAACTACAACAACATCACATTGGCAGGTACGACTGCAAGCAGTACACAAGATGCAACTACAGGCAAGATCACCACAACAGGTGGTACAAGCT
TGAACAATGTTGCAAGTGCGGGTGACTACAAAGATGTTGCCAATGCAAGCAAAGGTGTAAACGCAGGTGACTTGAACAATGCAGTTGTTGATGC
AACCAATGCAGCGACCAGCAAAGGCTTTGCATTACAAGCAGCAGATGGCGCTAAAGTTCAGAAGAACCTAGGCGAAGCAGTTGAAGTTGTTGGT
GCGGACAGTAACATCACCACGAAAGTTGCAGGCGGTCAGGTTGCAATTGAGTTAAATAAAAACCTCAACAACTTAACTGGCATTACCGTGAACG
ATGGAACCAATGGCACCAATGGTTCAACTGTGATTGGTAAAGATGGTATTTCGGTTAAAGATGGTTCAGGCAATACCATTGCAGGTGTAGATAA
CACAGCGTTGACAGTTAAAGATGGCAGTGGCAACACAGAAACCAGCATTAACCAAGCGATCAACACGTTAAATGCAGCGCAAGGTGAAACTGAT
AAGTTTGCAGTGAAGTACGACAAAAATGCTGATGGCAGTGCAAACTATAACAATGTCACTTTAGCTGGTACAAATGGCACAATAATCAGCAATG
TTAAAGCGGGTGCTGTGACCTCAACATCTACTGATGCGATCAATGGTAGCCAATTATATGGTGTTGCAAACAGCGTGAAGAATGCAATTGGTGG
TTCAACCACAATTGATGCAACGACTGGTGCAATCACGACGACCAATATTGGTGGTACAGGTTCAAATACGATTGATGGTGCAATCAGCAGTATT
AAAGATTCAGCGACTAAAGCGAAAACCACGGTAAGTGCTGGGGATAATGTTGTCGTTACATCGGGTACCAATGCAGATGGCTCAACAAACTATG
AAGTTGCGACAGCGAAAGACGTTAACTTTGACAAAGTGACTGTAGGTAGTGTTGTTGTAGATAAATCAAGCAATACAATCAAAGGATTAAGTAA
```

Fig. 2 (continued)

```
TACCACTTGGAACGGAACAGCAGTATCAGGTCAAGCGGCGACAGAAGACCAGTTAAAAACGGTCAGCGATGCGCAAGGTGAAACTGATAAGTTT
GCAGTGAAGTACGACAAAAATGCTGATGGCAGTGCGAACTACAACAGTATTACTGCAGGCAATGGTAACGGTACTGCAGCAACGATCGGAACTG
ACACAGCAGGTAATAGTGTTGTGACCAGTGGCGGAACTAAAATTAGTAATGTTGCGAATGGTGTCAATGCAAGTGATGCAGTAAACAAAGGTCA
ATTGGATAGCTTAAGTACAGGTCTTACCAATACAGGCTTTGGTTTAAAAGCAGCAGATGGCAACACCGTTAACAAAAAATTAGGCGAAGCAGTA
GACGTTGTCGGTGCTGACAGCAACATCACCACGAAAGTTGCAGGCGGTCAGGTTGCGATTGAGTTAAATAAAAACCTCAACAACTTAACTGGCA
TTACCGTGAACGATGGAACCAATGGCACCAATGGTTCAACTGTGATTGGTAAAGATGGTATTTCGATTAAAGATGGTTCAGGCAATACCATTGC
AGGTGTAGATAACACAGCGTTGACGGTTAAAGATAGCAGTGGCAACACAGAAACCAGCATTAACCAAGCGATCAACACGTTAAATGCAGCGCAA
GGTGAAACTGATAAGTTTGCAGTGAAGTACGATAAGAATGCTGATGGCAGTGTGAACTATAACAATGTCACTTTAGCAGGTACAAATGGCACAA
TAATCAGAAATGTTAAAGCGGGTGCTGTGACCTCAACATCTACTGATGCGATCAATGGTAGCCAATTATACGATATTGCAAACAGCGTGAAGAA
TGCAATTGGTGGTTCAACCACAAGAGATGTAACGACTGGTGCAATCACAACGACCAATATTGGTGGTACAGGTTCAAACACGATTGATGGTGCA
ATCAGCAGTATTAAAGATTCAGCGACTAAAGCGAAAACCACGATAAGTGCTGGGGATAATGTTGTCGTTACATCGGGTACCAATGCAGATGGCT
CAACAAACTATGAAGTTGCGACAGCGAAAGACGTTAACTTTGACAAAGTAACTGTAGGTAATGTTGTTGTTGATAAGGCAAATGACACGATCCA
AGGTTTGAGCAATAAAGATCTAAATTCAACTGATTTTGCGACCAAAGGTAGAGCTGCGACTGAAGAACAGTTAAAAGCAGTGATTACCAGTAAT
ATCACGGAAGTTGTGGATGGTAATGGCAACAAGGTGAATATTATTGACCAAGTTGTAAATACCAAACCTGACAATAAGAACCAAGATTCATTGT
TCTTAACGTATGACAAACAAGGTCAAGAAACCACAGATCGCCTAACGATTGGTCAAACGGTACAGAAGATGAATACTGATGGTATTAAATTCTT
CCATACCAATGCCGATACATCAAAAGGTGATTTGGGTACAACAAATGACTCAAGTGCAGGTGGTTTAAAACTCTACAGCAATTGGTGTAAATGCG
ATTGTTGCGAATGGTGCAGATAGTTCAGTTGCTTTAGGTCATAACACCAAAGTCAATGGTAAACAATCAATTGCAATTGGTTCTGGTGCAGAAG
CTTTAGGCAATCAATCGATCAGTATTGGTACAGGCAATAAAGTCACTGGTGATCATTCGGGTGCGATTGGTGATCCAACTATTGTAAATGGTGC
AAAACAGCTACTCTGTGGGTAATAACAACCAAGTACTTACAGATGACACTTTCGTACTTGGAAACAATGTCACCAAAACTATTGCTGGTTCAGTA
GTATTGGGTAACGGTTCAGCTGCAACGACAGGTGCTGGTGAGGCAGGCTATGCCTTATCTGTAGCAACAAATGCAGATAAAGCCGCGATCACTA
AAACTACGTCAAGCACTGGTGCTGTTGCAGTTGGTGATGCGTCGAGCGGTATTTATCGTCAAATTACCGGTGTTGCTGCGGGTAGCGTAGATTC
AGATGCTGTGAACGTTGCACAGTTAAAAGCGGTGGGTAACCAAGTTGTAACGACTCAAACTACATTGGTGAACAGTTTGGGTGGTAACGCTAAA
GTAAATGCAGACGGTACGATTACAGGACCAACTTATAATGTTGCTCAAGGTAATCAGACCAATGTTGGTGATGCATTAACTGCGCTTGATAACG
CAATTAATACTGCGGCAACAACATCTAAATCGACTGTTTCTAATGGTCAGAATATTGTTGTCAGCAAGAGCAAAAATGCAGATGGTTCAGACAA
CTATGAAGTATCAACAGCAAAAGACTTGACAGTTGATTCTGTCAAAGCGGGTGATACGGTTCTGAATAATGCAGGTATTACAATTGGCAATAAC
GCAGTTGTATTGAACAACACTGGATTAACCATTAGTGGTGGACCAAGTGTTACCTTGGCAGGCATCGATGCAGGCAATAAAACCATTCAAAATG
TTGCGAATGCAGTAAATGCAACAGATGCAGTCAACAAAGGGCAATTGGACAGCGCAATTAACAATGTGAATAACAATGTAAATGAGCTTGCCAA
CAACGCTGTTAAATATGACGATGCATCAAAAGATAAGATCACACTTGGTGGTGGGGCAACTGGTACAACAATCACCAATGTGAAAGATGGTACT
GTTGCGCAAGGTTCTAAAGATGCTGTGAATGGCGGTCAATTGTGGAATGTTCAACAACAAGTTGATCAGAACACAACTGATATTAGCAATATCA
AAAATGATATTAACAACGGTACTGTTGGTTTGGTTCAACAAGCAGGTAAAGATGCACCAGTGACGGTTGCAAAAGATACTGGCGGTACAACGGT
GAATGTCGCTGGAACAGATGGCAACCGAGTAGTGAcAGGTGTTAAGGAAGGTGCAGTGAATGCAACATCTAAAGATGCTGTCAATGGTAGTCAA
TTGAATACAACCAACCAAGCGGTAGTCAATTATCTTGGTGGTGGGGCAGGTTATGACAACATTACAGGTAGCTTCACAGCGCCAAGTTATACGG
TAGGTGACTCGAAATACAACAATGTTGGTGGCGCAATTGATGCATTGAATCAAGCAGATCAAGCATTGAATAGCAAAATTGACAATGTCAGTAA
CAAGTTGGATAACGCATTCCGTATTACCAACAACCGTATTGATGATGTAGAGAAAAAAGCCAATGCTGGTATTGCCGCTGCGATGGCTCTGGAA
TCAGCACCATATGTCCCAGGTAAATATACCTATGCAGCAGGCGCAGCTTACCACGGTGGTGAAAATGCGGTAGGTGTGACTTTACGTAAAACTG
CAGACAATGGTCGTTGGTCGATTACAGGCGGTGTAGCTGCAGCGTCTCAAGGCGATGCAAGTGTTCGTATCGGTATCAGCGGTGTGATTGACTA
ATTCACTCGACAGGGAAGATCTTCGGGTCTTCCTTTTTCTTCGAAAATTTTTTAAGAGAGAAAAAATGAAAGCATTTAACAAAAAAATTATGTT
TGGTGTATTCAGCGGTCTTGTGATGTCATTGAGCCATGCTGCTGAAGTCGAAAGTGCAAATACGCAAGAAATCCATTTTCCTGAAATCAAAGAC
AGCTATTTAAAACAAGTGAACCGTTATGAATATGACGATGTCGCACGTTTAGACAAGGGATTAACCAAAGATCAGATTCGCCATATTTTGGGAA
ATCCTCAATTCTCTGAAGGTCTTTTTGCGGTTAAGACATGGAATTATGTATTGGATATTCGTGAGCCTAACTCAAACCAATATAAGCGTTGCCA
ATTACGCATAGATTTTGATAAGCAATACCGTTCAGACAATCTATATTGGAAAGGTGAACAATGCCAAGGCTTAATGGCTTGGGGGATTAATAAT
CAGTCTGAGACTGAGCAAACGACTCTAGCCACCTGGTGGGCAGTCTGCAAGTGTTTTGTTTTATTTTGATCATGCGGATAAAAATGGTGTAAAGA
ACGCTGAAGTGATTCGTAAAATCGCAGATCAGATTAAACAATCTGATGCGAATAGCCCTGTTTTTGTGGCTGGATATACTGATGTTTAGGATC
ATTTCAGTATAACCAACGTTTATCTGCCCAAAGAGCGAATACAGTCGTTGAACTCTTGAAGCAACAAGGCATTCGTGGCGAGCAAATTCAGTAC
AGTGCTGAAAATAAAACAGATGTGTACCAAAAGTGCGCAGGGATCAATAAAAAAGATCCAACTGGTTGAATGTCTAGCACCTAACCGTCGTGTGA
```

Fig. 2 (continued)

```
ATATCACGTGGTAAGTCTTATTTATTCAATCTAATTTTGGATAATCCAAACAAAAAACGATATGTGTTCCACATTATCGTTTTTTGTTTTTTGA
GCAGGTGTTGATTAAAAAATCAAGGAGCTGATGAGATTGCAAAAATTTCCAATTAATTTAAAACAATAAAGTACGCAAATGATGAAAAAACAGT
TGTGTTAATGATTGGCTTGGGGTTTACCTTTCTGGCACAAGCATTTGATAAAAAAGTAATGATATTTCGATTATCAATATTTGAGCTTCTATGA
ATAGAGATCTTTTATAAAATTAAATTTAGTGATTATTGTTAAATGATAAATATTATTTATTAAAAAATAAAAAATTATTCATAGAAGTTTTGTG
TCTAATCTGGCGTGTTAGCGTTATATTAAATATCAATATTCATTTATCTCTAAACCCTGTTGAAATATAAGTAAACACGTCTTGTTTAAAAAAA
GATCATACTCAAGGTCATTGGTTCTACGTTAACTTATAGTATGATGTGTACATATTTCGACTGATTTATTGCTATATCAGTTTTTATTTAGCCAG
AGTGAATCTGATTCATTTCAAGCTCAAACAATGTNGGAAATACAAATGCCNGACTATCGTTCAAAAACATCGACACATGGAAGAAATATGGCTG
GTGCACGTGGCTTATGGCGTGCAACAGGAATGAAAGATGAAGATTTCGGTAAGCCGATTATTGCGGTAGTCAACTCATTTACCCAGTTTGTGCC
TGGTCATGTCCACCTTAAAGATTTAGGTCAACTGGTTGCGGAACAAATCCAAGCAGCTGGTGGTGTGGCAAAAGAATTTAATACCATTGCCGTG
GATGATGGTATCGCAATGGGGCATGATGGCATGCTGTATTCATTGCCTTCACGTGATTTGATTGCAGACTCTGTCGAATATATGGTCAATGCAC
ACTGCGGCAGATGCCATGGTGTGTATTTCAAACTGTGACAAAATTACCCCAGGGATGTTAATGGCAGCGATGCGGTTAAACATTCCAGTGGTGTT
TGTGTCGGGTGGACCAATGGAAGCGGGTAAAGTTAAAATCCGTGGTACAGAACGTGCAATTGACTTAGTTGATGCGATGGTGGTTGCAGCCGAT
GATAATTTTACAGATGAAGAAGTAAAAGAATACGAGCGTTCAGCATGCCCAACATGTGGTTCATGTTCAGGTATGTTCACAGCAAATTCGATGA
ACTGTTTGACAGAAGCATTGGGGTTGTCGTTACCAGGAAATGGTTCAACATTAGCAACGCATGCTAACCGTAAGAAACTATTCGAAAAAGCAGG
TCAATTGGTTGTTGAATTGGCAAAACGCCATTATGAACAAGATGATTACACGGTATTACCACGTTCGATCGCAACCAAAGCATCTTATGAAAAT
GCCATGACGCTCGATATTGCGATGGGTGGTTCAACCAATACCGTATTGCATTTATTGGCTGCTNCCAGTGAAGCAGGTGTTGACTTTACCATGG
ATGACATTGATCGTTTATCGCGTAAAGTGCCTGTATTATGTAAAGTTGCTCCTGCAAAGCAGGATGTGCATATGGAAGATGTGCATCGTGCCGG
TGGCATCATGTCCATTCTCGGTGAATTGATCGTGCAGGTTTATTAGATACATCGGTACACACTGTGCATGAGCACACCTTAAAAGATGCATTG
GATAAATGGGATATTATTCGTACAGAAGACCCAGTGGTATATGAGTTCTTCCGCTCAGCGCCAGGTGGTGTTCCAACTCAAACAGCATTCTCAC
AAAAATCGCTATTACCAGACTTTGGATGGCAATCGTGAAACAGGTGTGATTCGTAATGCTGAACATGCTTTCTCTAAAGATGGTGGCTTGGCAGT
ATTGTATGGCAACATTGCTGTAGATGGGTGTATTGTTAAAACAGCAGGTGTTGATGATTCAATTTTAAAATTTAATGGAACTGCACGAGTATTT
GAAAGCCAAGATGCTGCAGTAGATTCAATTTTAGGACATGAAATTAAGGCTGGTGATGTGGTTGTGATCCGTTATGAAGGACCACGTGGTGGAC
CGGGTATGCAGGAAATGCTTTATCCGACCAGTTATTTAAAATCAAAAGGCTTAGGTAAAGAATGTGCTTTACTGACAGATGGACGTTTCTCTGG
AGGTTCTTCTGGCCTTTCAATTGGTCATGTATCACCTGAAGCTGCTGAAGGTGGTGTGATTGGATTGGTTGAAGATGGTGATTTGATTGAAATT
GATATTCCAAATCGTACCATCAATCTTGCTGTGGATGAGGCGACCTTAGCTGCTCGACGTAAGCTT
```

<u>Methionyl-tRNA formyltransferase coding region</u>
<u>Putative promoter region</u>
<u>Signal peptide</u>
<u>Head domain</u>
<u>Neck domain</u>
<u>Stalk comain</u>
<u>Membrane anchor domain</u>
<u>Tol-OmpA coding region</u>
<u>Dihydroxyacid dehydratase coding region</u>

Fig. 3

MNKIYKVIWNATLLAWVAVSELAKGKTKSTTSKSKAKSLSSSVIVGGILLTTPLSLIAATVQVGGGTNSGTTATASTNCADLYNYQNPENSGSG
AAGNYNAGNPSVCSIAIGENAQGGTSGTGGSPGIAIGGNSKATGGLSVAIGGYAQATNVGSIALGTAALSSGFNSLAISRQAAATNNYSIAIGT
TSVSKGVGSIAMGHSTNASGDQSIAIGSSDAVNSATATTTYDGTTNTQASGSKSIAIGASAKASTNNSIALGAGSVTSAQSGNSYLTGVGASAT
NGVVSVGTSTATRRIQNVADGSAASDAVTVAQLDKAYDDTNGRLAAALGTGSGAAYNAANNTYTAPTNIGGTGKNTIDDAIKATQRSVVAGSNI
VVTPTTASDGSISYSVATSATPTFTSITVNNAPTAGTDATNKTYVDSKAAASRTEVAAGSNVSGVVKTTGANGQDVYTVNANGTTASAGSSAVT
VTPGTKDANNVTDYKVDLSATTKTDIQKGVDAKNAVDTAGLKFKGDTATTSNTKKLGDTVSITGDTNISTVATTDGVQVKLNPNLDLGATGSVK
TGNTTINNAGVTADQVTVGGVVINNTSGINAGGKAITNVAAPTNNTDAANKKYVDDAGTALTNLGFGLKAQDGTTVNKKLGEAVDIVGSNSNIS
TKVNAGKVEVALSNTLDLGTTGSVTTGSTVINNTGVTATQVTANKVTINNAPTAGTDATNKTYVDSKAAASRTEVAAGSNVSGVVKTTGANGQD
IYAVNANGTTASAGSSAVTVTPGTKDANNVTDYKVDLSATTKTDIQKGVDAKNAVDTAGLKFKGDTATTSNTKKLGDTVSITGDTNISTVATTD
GVQVKLNPNLDLGATGSVKTGNTTINNAGVTADQVTVGGVVINNTSGINAGGKAITNVAAPTNNTDAANKKYVDDAGTALTNLGFGLKAQDGTT
VNKKLGEAVDIVGSNSNISTKVNAGKVEVALSNTLDLGTTGSVTTGSTVINNAGVTATQVTANKVTVNNAPTAGTDATNKTYVDSKAAASRTEV
AAGSNVSGVVKTTGANGQDVYTVNANGTTASAGSSAVTVTPGTKDANNVTDYKVDLSATTKTDIQKGVDAKNAVDTAGLKFKGDTATTSNTKKL
GDTVSITGDTNISTVATTDGVQVKLNPNLDLGATGSVKTGNTTINNAGVTADQVTVGGVVINNTSGINAGGKAITNVAAPTNNTDAANKKYVDD
AGTALTNLGFGLKAQDGTTVNKKLGEAVEVVGADSNITTKVAGGQVAIELNKNLNNLTGITVNDGTNGTNGSTVIGKDGISVKDGSGNTIAGVD
NTALTVKDGSGNTETSINQAINTLNAAQGETDKFAVKYDKNADGSVNYNNITLAGTTASSTQDATTGKITTTGGTSLNNVASAGDYKDVANASK
GVNAGDLNNAVVDATNAATSKGFALQAADGAKVQKNLGEAVEVVGADSNITTKVAGGQVAIELNKNLNNLTGITVNDGTNGTNGSTVIGKDGIS
VKDGSGNTIAGVDNTALTVKDGSGNTETSINQAINTLNAAQGETDKFAVKYDKNTDGSTNYNSITAGNGNGTAATIGTDTAGNSVVTSGGTKIS
NVANGVNASDAVNKGQLDSLSTGLTNTGFGLKAADGNTVNKKLGEAVDVVGADSNITTKVAGGQVAIELNKNLNNLTGITVNDGTNGTNGSTVI
GKDGISIKDGSGNTIAGVDNTALTVKDGSGNTETSINQAINTLNAAQGETDKFAVKYDKNADGSANYNNITLAGTTASSTQDATTGKITTTGGT
SLNNVASAGDYKDVANASKGVNAGDLNNAVVDATNAATSKGFALQAADGAKVQKNLGEAVEVVGADSNITTKVGGGQVAIELNKNLNNLTGITV
NDGTNGTNGSTVIGKDGISVKDGSGNTIAGVDNTALTVKDGSGNTETSINQAINTLNAAQGETDKFAVKYDKNADGSVNYNNITLAGTTASSTQ
DATTGKITTTGGTSLNNVASAGDYKDVANASKGVNAGDLNNAVVDATNAATSKGFALQAADGAKVQKNLGEAVEVVGADSNITTKVAGGQVAIE
LNKNLNNLTGITVNDGTNGTNGSTVIGKDGISVKDGSGNTIAGVDNTALTVKDGSGNTETSINQAINTLNAAQGETDKFAVKYDKNADGSVNYN
NITLAGTTASSTQDATTGKITTTGGTSLNNVASAGDYKDVANASKGVNAGDLNNAVVDATNAATSKGFALQAADGAKVQKNLGEAVEVVGADSN
ITTKVAGGQVAIELNKNLNNLTGITVNDGTNGTNGSTVIGKDGISVKDGSGNTIAGVDNTALTVKDGSGNTETSINQAINTLNAAQGETDKFAV
KYDKNADGSANYNNVTLAGTNGTIISNVKAGAVTSTSTDAINGSQLYGVANSVKNAIGGSTTIDATTGAITTTNIGGTGSNTIDGAISSIKDSA
TKAKTTVSAGDNVVVTSGTNADGSTNYEVATAKDVNFDKVTVGSVVVDKSSNTIKGLSNTTWNGTAVSGQAATEDQLKTVSDAQGETDKFAVKY
DKNADGSANYNSITAGNGNGTAATIGTDTAGNSVVTSGGTKISNVANGVNASDAVNKGQLDSLSTGLTNTGFGLKAADGNTVNKKLGEAVDVVG
ADSNITTKVAGGQVAIELNKNLNNLTGITVNDGTNGTNGSTVIGKDGISIKDGSGNTIAGVDNTALTVKDSSGNTETSINQAINTLNAAQGETD
KFAVKYDKNADGSVNYNNVTLAGTNGTIIRNVKAGAVTSTSTDAINGSQLYDIANSVKNAIGGSTTRDVTTGAITTTNIGGTGSNTIDGAISSI
KDSATKAKTTISAGDNVVVTSGTNADGSTNYEVATAKDVNFDKVTVGNVVVDKANDTIQGLSNKDLNSTDFATKGRAATEEQLKAVITSNITEV
VDGNGNKVNIIDQVVNTKPDNKNQDSLFLTYDKQGGQETTDRLTIGQTVQKMNTDGIKFFHTNADTSKGDLGTTNDSSAGGLNSTAIGVNAIVAN
GADSSVALGHNTKVNGKQSIAIGSGAEALGNQSISIGTGNKVTGDHSGAIGDPTIVNGANSYSVGNNNQVLTDDTFVLGNNVTKTIAGSVVLGN
GSAATTGAGEAGYALSVATNADKAAITKTTSSTGAVAVGDASSGIYRQITGVAAGSVDSDAVNVAQLKAVGNQVVTTQTTLVNSLGGNAKVNAD
GTITGPTYNVAQGNQTNVGDALTALDNAINTAATTSKSTVSNGQNIVVSKSKNADGSDNYEVSTAKDLTVDSVKAGDTVLNNAGITIGNNAVVL
NNTGLTISGGPSVTLAGIDAGNKTIQNVANAVNATDAVNKGQLDSAINNVNNNVNELANNAVKYDDASKDKITLGGGATGTTITNVKDGTVAQG
SKDAVNGGQLWNVQQQVDQNTTDISNIKNDINNGTVGLVQQAGKDAPVTVAKDTGGTTVNVAGTDGNRVVTGVKEGAVNATSKDAVNGSQLNTT
NQAVVNYLGGGAGYDNITGSFTAPSYTVGDSKYNNVGGAIDALNQADQALNSKIDNVSNKLDNAFRITNNRIDDVEKKANAGIAAAMALESAPY
VPGKYTYAAGAAYHGGENAVGVTLRKTADNGRWSITGGVAAASQGDASVRIGISGVID

<u>Signal peptide</u>
<u>Head domain</u>
<u>Neck domain</u>
<u>Stalk domain</u>
<u>Membrane anchor domain</u>

Wild-type DH5α strain (upper left), DH5α::aadA (upper right), DH5α::aadA-ompA (lower)

Fig. 12

| SEQ ID NO: | Primer | Sequence (5'→3') | bp | Tm (°C)* | Description |
|---|---|---|---|---|---|
| 16 | T1-5kb RC | GTCGACTAAACGACCATTTGTATCATCATAAGC | 33 | 72 | Inverse PCR(Tol5-5kb) |
| 17 | T1-5kb RC-2 | TAAACGACCATTTGTATCATCATAAGC | 27 | 72 | Inverse PCR(Tol5-5kb) |
| 18 | T1-5kb R3 | GTCGACGGTACAGGTAGTGGTGCTGCCTA | 29 | 72 | Inverse PCR(Tol5-5kb) |
| 19 | T1-5kb R3-2 | GGTACAGGTAGTGGTGCTGCCTA | 23 | 72 | Inverse PCR(Tol5-5kb) |
| 20 | Tol5-TKD-F | AATTTCAAAAAAATTAAACCAATTGG | 26 | 62 | PCR(AadA,adhesin operon) |
| 21 | Tol5-TKD-R | GTTAAATGCTTTCATTTTTCTCTC | 25 | 62 | PCR(AadA) |
| 22 | Tol5-ad-probe2F | CACGAAAGTTGCAGGCGGTC | 20 | 64 | Probe(Tol5-No.6,CC,C2) |
| 23 | Tol5-ad-probe5F | ACAATGTTGCAAGTGCGGGTG | 21 | 64 | Probe(Tol5-B,M,S) |
| 24 | Tol5-ad-probe2R | TGCAATGGTATTGCCTGAACC | 21 | 62 | Probe(Tol5-No.6,CC,C2) |
| 25 | Tol5-ad-probe6R | GTTCTTCTGAACTTTAGCGCCA | 22 | 64 | Probe(Tol5-B,M,S) |
| 26 | Tol5-ad-op-R3 | TGTTTGAGCTTGAAATGAATCAGA | 24 | 64 | RT-PCR |
| 27 | pUC118R | CAGGAAACAGCTATGACCATGA | 22 | 64 | RT-PCR,PCR(adhesin operon) |
| 28 | pUC118F | GTTTTCCCAGTCACGACGTTG | 21 | 64 | PCR, Sequence |

*Tm[°C] = (G+C) × 4 +(A+T) × 2

METHOD AND GENE FOR PROVIDING OR ENHANCING NONSPECIFIC ADHESIVE PROPERTY AND/OR AUTOAGGLUTINATING PROPERTY FOR MICROORGANISMS

FIELD OF THE INVENTION

The present invention relates to a method for providing or enhancing nonspecific adhesive property and/or auto agglutinating property for a target microorganism, DNA used for such method, a protein encoded by such DNA, a microorganism obtained by such method, and a method for culturing such microorganism.

BACKGROUND OF THE INVENTION

Microorganisms have activity of conversion of substances based on excellent catalytic action. Thus, microorganisms have been extensively used in the fields of, for example, brewing, fermented food production, and wastewater or gas treatment. Recently, production of pharmaceutical products with the use of recombinant microorganisms, fermentative production of bioethanol, and synthesis of chemical products with the use of microorganisms have been implemented or researched, and techniques involving the use of microorganisms are industrially important. However, production of microbial cells that play key roles in reactions is costly in terms of, for example, media and energy. In addition, microbial reactions are often carried out in aqueous solutions, which necessitate the separation of microorganisms from reaction solutions after substances are produced. Microorganisms were mainly separated via centrifugation or filtration in the past.

In order to facilitate separation and continuously or repeatedly use valuable microbial cells, immobilization and auto-agglutination of microbial cells were considered to be effective. Examples of conventional immobilization techniques include immobilization through entrapment in a gel such as alginic acid and surface immobilization to allow microorganisms to adsorb on the surfaces of porous carriers. However, the entrapment immobilization method is disadvantageous in that transportation of oxygen and substrates in gel is often limited in the rate, gel is brittle in mechanical strength and thus is likely to be destroyed by agitation or the like, and microbial cells leak from gel, for example. Also, a conventional technique of surface immobilization does not involve accumulation of target microorganisms on a surface, and the technique merely involves introduction of porous carriers or the like for use in the fields of wastewater processing or environmental cleanup where large quantities of many sorts of microorganisms are present, thereby allowing easily-adhering microorganisms to be carried on a surface as a biofilm. That is, there is no technique that allows microorganisms of interest to adhere to a solid surface as one likes. Regarding agglutination, a method involving the use of coagulating agents, such as high-molecular-weight polymers, is extensively used in wastewater processing. In addition, a method involving screening of agglutinating microorganisms for use thereof has been employed. However, there is no technique that enables spontaneous agglutination of non-agglutinating microbial cells, and particularly bacteria.

SUMMARY OF THE INVENTION

A method for providing or enhancing a nonspecific adhesive property or an autoagglutinating property, or both a nonspecific adhesive property and an autoagglutinating property in a target microorganism comprising introducing into the target microorganism a nucleic acid encoding autotransporter adhesin, wherein the nucleic acid sequence is derived from a microorganism having a nonspecific adhesive property is provided.

In another embodiment of the invention a microorganism obtained by the method is provided.

Another embodiment of the invention provides an isolated nucleic acid selected from the group consisting of (a) an isolated nucleic acid comprising the nucleotide sequence of SEQ ID NO: 1; (b) an isolated nucleic acid having at least 70% homology to the nucleotide sequence of SEQ ID NO: 1, wherein the isolated nucleic acid encodes a protein that provides or enhances a nonspecific adhesive property, an autoagglutinating property, or both a nonspecific adhesive property and an autoagglutinating property in a microorganism; and (c) an isolated nucleic acid consisting of a part of the nucleotide sequence of SEQ ID NO: 1, wherein the nucleic acid sequence encodes a protein that provides or enhances a nonspecific adhesive property, an autoagglutinating property, or both a nonspecific adhesive property and an autoagglutinating property in a microorganism.

In another embodiment of the invention a protein selected from the group consisting of (a) a protein comprising the amino acid sequence of SEQ ID NO: 2; (b) a protein comprising an amino acid sequence derived from the amino acid sequence of SEQ ID NO: 2 by deletion, substitution, insertion, or addition of one or more amino acids, wherein the protein provides or enhances a nonspecific adhesive property, an autoagglutinating property, or both a nonspecific adhesive property and an autoagglutinating property of the microorganism; and (c) a protein consisting of a part of the amino acid sequence of SEQ ID NO: 2, wherein the protein provides or enhances a nonspecific adhesive property, an autoagglutinating property, or both a nonspecific adhesive property and an autoagglutinating property of the microorganism is provided.

Additional embodiments of the invention provide methods for culturing a microorganism comprising allowing a plurality of the microorganisms of the invention to autoagglutinate and/or adhere to a carrier.

Also provided is a method for production of a chemical product comprising culturing microorganisms of the invention.

BRIEF DESCRIPTION OF THE DRAWINGS

FIG. 2 shows whole the nucleotide sequence determined as a result of cloning and sequencing in Example 1.

FIG. 3 shows the amino acid sequence of AadA.

FIG. 12 shows a table summarizing primers used in Example 1.

DETAILED DESCRIPTION OF THE INVENTION

Figure 1:
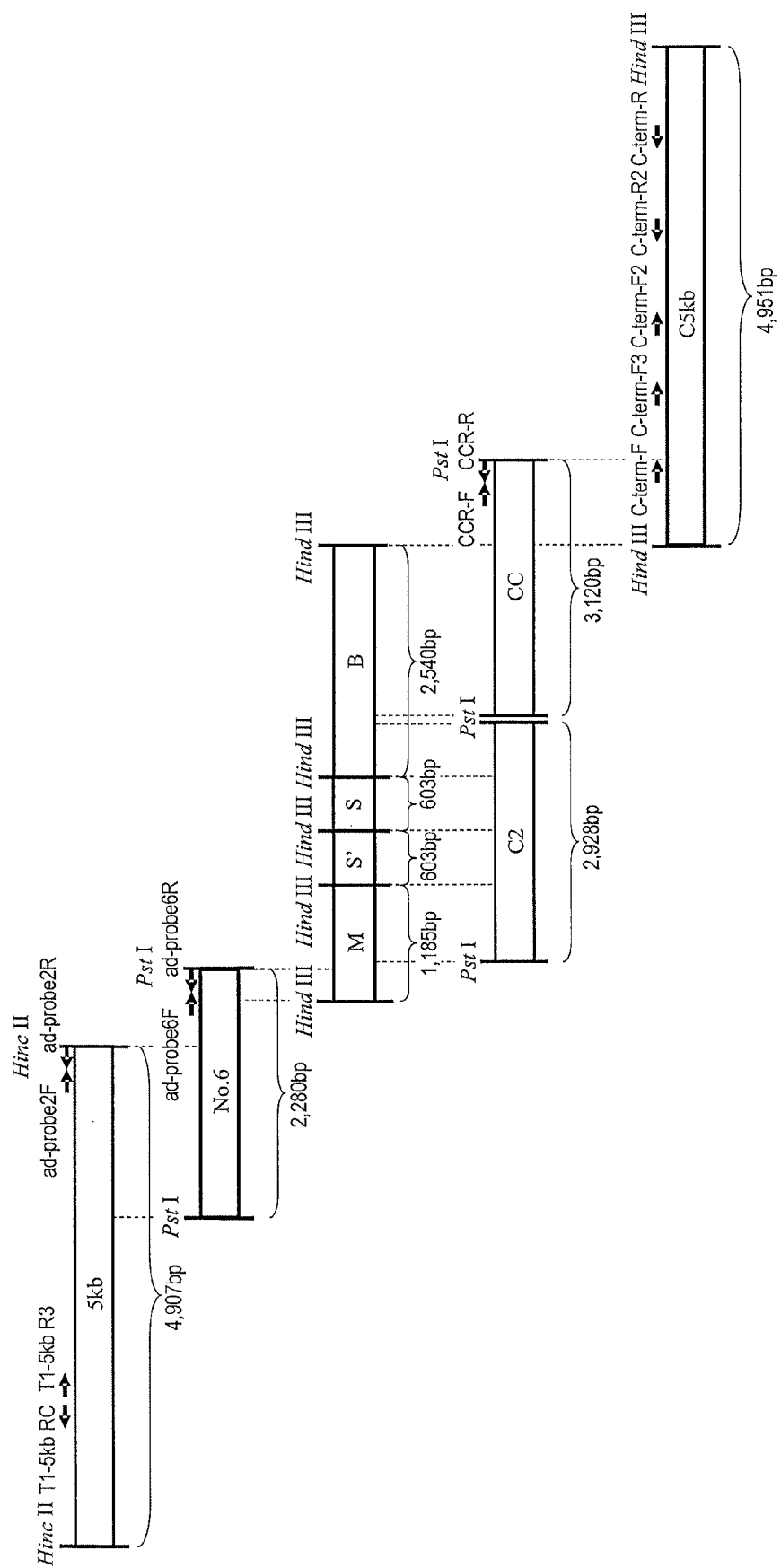
FIG. 1 shows the positional relationship of sequence fragments obtained in Example 1.

The method of the present invention comprises introducing a DNA encoding autotransporter adhesin from a microorganism having nonspecific adhesive property (i.e., the autotransporter adhesin gene) into the target microorganism.

Some pathogenic microorganisms adhere to certain biotic surfaces (e.g., surfaces of certain cells, organisms, or tissues thereof) and form colonies. However, the term "microorganism having nonspecific adhesive property" used in the present invention refers to a microorganism that is capable of adhering to any type of biotic or abiotic surfaces, including abiotic surfaces of carriers or the like, in addition to certain types of biotic surfaces. A microorganism having nonspecific adhesive property can adhere to, for example, glass, plastic, and metal carriers.

Examples of microorganisms having nonspecific adhesive property include Gram-negative bacteria, such as *Acinetobacter* bacteria, *Pseudomonas* bacteria, *Escherichia* bacteria, *Caulobacter* bacteria, *Xanthomonas* bacteria, *Haemophilus* bacteria, *Yersinia* bacteria, *Bartonella* bacteria, *Neisseria* bacteria, and *Actinobacillus* bacteria. In the present invention, *Acinetobacter* spp. are particularly preferable.

A specific example of a microorganism having nonspecific adhesive property is strain *Acinetobacter* sp. Tol 5. This strain is capable of degrading toluene and was isolated from a reactor for off-gas treatment. The strain is deposited at the International Patent Organism Depositary of the National Institute of Advanced Industrial Science and Technology, Incorporated Administrative Agency (Tsukuba Central 6, 1-1-1 Higashi, Tsukuba, Ibaraki, Japan) under the Accession Number: FERM P-17188.

Nonspecific adhesive property of microorganisms can be evaluated by an adhesion test via crystal violet staining (the CV adhesion test). Specifically, the bacterial cell liquid culture is subjected to centrifugation, the culture supernatant is removed, an inorganic salt medium is added to the cell pellet, the cell suspension is obtained via ultrasonication, the turbidity ($OD_{660}$) of the cell suspension is adjusted to a constant level (0.5 or lower) with a medium, 1 ml each of the suspension is added to each well of a 48-well plastic plate, incubation is carried out at an optimal temperature for the relevant microorganisms for 2 hours, the suspensions are completely removed from the wells using a pipette, the wells are washed with 1 ml of inorganic salt medium, the plate is air dried, an aqueous solution of 1% aqueous crystal violet solution is added to the wells, incubation is carried out at room temperature for 15 minutes, crystal violet is removed with the use of a pipette, the wells are washed twice with 1 ml of inorganic salt medium, the plate is air dried, 1 ml of inorganic salt medium is added to detach the stained bacterial cells from the inner wall of the wells, the cells are dispersed via ultrasonication, and absorbance ($A_{590}$) is then measured. Microorganisms exhibiting an absorbance $A_{590}$ of 0.15 or higher, preferably 0.18 or higher, and more preferably 0.2 or higher can be evaluated as having nonspecific adhesive property.

Autotransporter adhesins are proteins that are reported as adhesive nanofibers of Gram-negative bacteria. They are known to interact specifically with tissues, cell surface molecules, and extracellular matrix of hosts, although it is not reported that autotransporter adhesins nonspecifically adhere to a variety of solid surfaces. It is said that autotransporter adhesins have functions such as adhesion, invasion, cytotoxicity; serum tolerance, and intercellular propagation. Autotransporter adhesins have a common domain organization (i.e., the N-terminal signal peptide, the internal passenger domain, and the C-terminal translocator domain). In particular, the C-terminal translocator domain characterizes this protein family. Autotransporter adhesin secretion begins with an export across the inner membrane by the Sec system, which is mediated by the signal peptide. Subsequently, the translocator domain is inserted into the outer membrane and the β barrel structure is formed. In the end, the passenger domain passes through the outer membrane and appears on the bacterial cell surface. Autotransporter adhesins are divided into monomeric autotransporter adhesin and trimeric autotransporter adhesins (Shane E. Cotter, Neeraj K. Surana and Joseph W. St GemeIII, 2005, Trimeric autotransporters: a distinct subfamily of Autotransporter proteins, TRENDS in Microbiology, 13: 199-205). The translocator domain of monomeric autotransporter adhesin is considered to form the β barrel structure, which is a hydrophilic pathway consisting of 14 transmembrane antiparallel β-sheets and the transmembrane α helices, from a single subunit. In contrast, it is known that the translocator domain of trimeric autotransporter adhesins forms a thermostable and SDS-resistant trimer in the outer membrane, a subunit having four β-sheets is oligomerized, and thus the 12-stranded β barrel structure is formed from 3 subunits. Also, many general autotransporter adhesins have intramolecular chaperone regions, although the trimeric autotransporter adhesin subfamily does not have the chaperone. In addition, the passenger domains of practically all monomeric autotransporter adhesins form non-covalent bonds with the translocator domains for linking to surfaces of bacteria, or are released outside the cells. However, the passenger domains of all trimeric autotransporter adhesin proteins are considered to remain linked to the translocator domains via covalent bonds.

Trimeric autotransporter adhesin is abbreviated as TAA, and it is also referred to as the Oca family (i.e., the Oligomeric Coiled-coil Adhesin Family) as a new class that forms a common oligomer structure, a coiled-coil structure (Andreas Roggenkamp, Nikolaus Ackermann, Christoph A. Jacobi, Konrad Truelzsch, Harald Hoffmann, and Jurgen Heesemann 2003, Molecular analysis of transport and oligomerization of the *Yersinia enterocolitica* adhesin YadA. J. Bacteriol. 185: 3735-3744).

In the present invention, trimeric autotransporter adhesin is preferable. Examples of trimeric autotransporter adhesins include *Yersina enterocolitica* adhesin (YadA, *Yersina* adhesin A) (El Tahir Y, Skurnik M. 2001, YadA, the multifaceted *Yersinia* adhesin, Int. J. Med. Microbiol., 291:209-218), *Haemophilus influenzae* Hia that causes meningitis (St. Geme J W 3rd, Cutter D., 2000, The *Haemophilus influenzae* Hia adhesin is an autotransporter protein that remains uncleaved at the C terminus and fully cell associated, J. Bacteriol., 182: 6005-13), *Aggregatibacter* (*Actinobacillus*) *actinomyceteincomitans* EmaA that causes periodontal diseases (Mintz, K. P. 2004, Identification of an extracellular matrix protein adhesin, EmaA, which mediates the adhesion of *Actinobacillus actinomycetemcomitans* to collagen, Microbiology. 150, 2677-2688), *Moraxella catarrhalis* UpsA1 and A2 that are major pathogens of respiratory infections (Lafontaine E R, Cope L D, Aebi C, Latimer J L, McCracken G H Jr, Hansen E J. 2000, The UspA1 protein and a second type of UspA2 protein mediate adherence of *Moraxella catarrhalis* to human epithelial cells in vitro, J. Bacteriol., 182: 1364-73),

*Bartonella henselae* BadA that causes cat-scratch diseases (Riess T, Andersson S G, Lupas A, Schaller M, Schäfer A, Kyme P, Martin J, Wälzlein J H, Ehehalt U, Lindroos H, Schirle M, Nordheim A, Autenrieth I B, Kempf V A., 2004, *Bartonella* adhesin a mediates a proangiogenic host cell response. J. Exp. Med., 200: 1267-78), *Neisseria meningitides* (meningococci) NadA (Capecchi B, Adu-Bobie J, Di Marcello F, Ciucchi L, Masignani V, Taddei A, Rappuoli R, Pizza M, Aricò B. 2005, *Neisseria meningitidis* NadA is a new invasin which promotes bacterial adhesion to and penetration into human epithelial cells, Mol. Microbiol., 55: 687-98), and phytopathogenic bacteria; i.e., *Xanthomonas oryzae* XadA (Ray S K, Rajeshwari R, Sharma Y, Sonti R V., 2002, A high-molecular-weight outer membrane protein of *Xanthomonas oryzae* pv. *oryzae* exhibits similarity to non-fimbrial adhesins of animal pathogenic bacteria and is required for optimum virulence, Mol. Microbiol., 46: 637-47).

Examples of preferable autotransporter adhesins include a protein comprising the amino acid sequence as shown in SEQ ID NO: 2 and proteins that are functionally equivalent thereto. The term "proteins that are functionally equivalent" refers to proteins having biological and biochemical functions equivalent to those of the protein comprising the amino acid sequence as shown in SEQ ID NO: 2. An example of a protein that is functionally equivalent to the protein comprising the amino acid sequence as shown in SEQ ID NO: 2 is a protein comprising an amino acid sequence derived from the amino acid sequence as shown in SEQ ID NO: 2 by deletion, substitution, insertion, or addition of one or several amino acids and having activity of providing or enhancing nonspecific adhesive property and/or autoagglutinating property for a microorganism. A further example is a protein consisting of a part of the amino acid sequence as shown in SEQ ID NO: 2 and having activity of providing or enhancing nonspecific adhesive property and/or autoagglutinating property for a microorganism; that is, a deficient protein comprising an amino acid sequence derived from the amino acid sequence as shown in SEQ ID NO: 2 by deletion of one or several regions comprising several tens to several hundreds, and optionally 1,000 or more, continuous amino acid residues and maintaining the activity of providing or enhancing nonspecific adhesive property and/or autoagglutinating property for a microorganism.

Deletion, substitution, insertion, or addition of one or several amino acids can be performed by modifying the sequence of DNA encoding the protein of interest (e.g., the nucleotide sequence as shown in SEQ ID NO: 1) by a conventional technique such as site-directed mutagenesis (Zoller et al., Nucleic Acids Res., 10, 6478-6500, 1982).

Side chains of amino acids constituting proteins vary in terms of hydrophobic properties, electric charge, size, and other conditions. Nevertheless, several highly conserved relationships between amino acid residues are known on an empirical basis or as a result of physicochemical measurement, in which the highly conserved relationships means that the side chains would not substantially influence the three-dimensional structure of the entire protein (also referred to as a "conformation"). Examples of known conservative substitutions between different amino acid residues include substitutions between amino acids such as glycine (Gly) and proline (Pro); glycine and alanine (Ala) or valine (Val); leucine (Leu) and isoleucine (Ile); glutamic acid (Glu) and glutamine (Gln); aspartic acid (Asp) and asparagine (Asn); cysteine (Cys) and threonine (Thr); threonine and serine (Ser) or alanine; and lysine (Lys) and arginine (Arg). Thus, amino acid substitution is preferably conservative.

The protein comprising the amino acid sequence as shown in SEQ ID NO: 2 is trimeric autotransporter adhesin comprising a signal peptide, a head domain, a neck domain, a stalk domain, and a membrane anchor domain. Thus, amino acid mutation preferably maintains such domain structure. In the amino acid sequence as shown in SEQ ID NO: 2, the signal peptide corresponds to amino acids 1 to 57, the head domains correspond to amino acids 108 to 269 and amino acids 2997 to 3148, the neck domains correspond to amino acids 296 to 319 and amino acids 3149 to 3172, the stalk domains correspond to amino acids 406 to 2966 and amino acids 3173 to 3537, and the membrane anchor domain corresponds to amino acids 3538 to 3630.

The term "several" means usually 2 to 10, preferably 2 to 5, and more preferably 2 to 3. Functionally equivalent proteins usually have high homology at the amino acid sequence level. The term "high homology" refers to usually 70% or more, preferably 80% or more, more preferably 90% or more, further preferably 95% or more, and most preferably 99% or more homology (or identity) at the amino acid level.

Concerning a protein consisting of a part of the amino acid sequence as shown in SEQ ID NO: 2, a sequence of several tens to several hundreds continuous amino acids that can be deleted from the sequence of SEQ ID NO: 2 is preferably a sequence corresponding to either of or both the stalk domains, either of the head domains, or either of the neck domains, and one or a plurality thereof may be deleted. In the aforementioned domains, deletion of the entire region from the head domain to the stalk domain that is located more closely to the amino terminus (i.e., positions 108 to 2966) or the entire region from the head domain to the stalk domain that is located more closely to the carboxyl terminus (i.e., positions 2997 to 3537) is more preferable. Further preferably, a plurality of repeated regions observed in the stalk domain are deleted such that each region appears only once without repetition. Most preferably, any one of the plurality of repeated regions observed in the stalk domain is deleted.

Examples of a preferable autotransporter adhesin gene (i.e., a DNA encoding autotransporter adhesin) include DNA comprising the nucleotide sequence as shown in SEQ ID NO: 1 and DNA that is functionally equivalent thereto. An example of DNA that is functionally equivalent to DNA comprising the nucleotide sequence as shown in SEQ ID NO: 1 is DNA comprising a nucleotide sequence having 70% or more, preferably 80% or more, more preferably 90% or more, further preferably 95% or more, and most preferably 98% or more homology (or identity) to the nucleotide sequence as shown in SEQ ID NO: 1 and encoding a protein having activity of providing or enhancing nonspecific adhesive property and/or autoagglutinating property for a microorganism. Another example is a DNA hybridizing under stringent conditions to a DNA comprising a nucleotide sequence complementary to the nucleotide sequence as shown in SEQ ID NO: 1 and encoding a protein having activity of providing or enhancing nonspecific adhesive property and/or autoagglutinating property for a microorganism. A further example is a DNA consisting of a part of the nucleotide sequence as shown in SEQ ID NO: 1 and encoding a protein having activity of providing or enhancing nonspecific adhesive property and/or autoagglutinating property for a microorganism; that is, a DNA of a deficient gene comprising a nucleotide sequence derived from the nucleotide sequence as shown in SEQ ID NO: 1 by deletion of 1 or several regions comprising continuous nucleotides of several tens to several hundreds, and optionally 1,000 or more, and encoding a protein that maintains the activity of providing or enhancing nonspecific adhesive property and/or autoagglutinating property for a microorganism.

Under stringent conditions, a specific hybrid is formed, but a nonspecific hybrid is not formed. Hybridization may be carried out under low or high stringency conditions, with high stringency conditions being preferable. Under low stringency conditions, hybridization is followed by washing at 42° C. in 5×SSC and 0.1% SDS, and preferably at 50° C. in 5×SSC and 0.1% SDS, for example. Under high stringency conditions, hybridization is followed by washing at 65° C. in 0.1×SSC and 0.1% SDS, for example.

A mutation of a nucleotide sequence preferably maintains a domain structure comprising a signal peptide, a head domain, a neck domain, a stalk domain, and a membrane anchor domain. In the nucleotide sequence as shown in SEQ ID NO: 1, the signal peptide corresponds to nucleotides 1 to 171, the head domains correspond to nucleotides 322 to 807 and nucleotides 8989 to 9444, the neck domains correspond to nucleotides 886 to 957 and nucleotides 9445 to 9516, the stalk domains correspond to nucleotides 1216 to 8898 and nucleotides 9517 to 10611, and the membrane anchor domain corresponds to nucleotides 10612 to 10890.

Concerning a DNA consisting of a part of the nucleotide sequence as shown in SEQ ID NO: 1, a sequence of several tens to several hundreds continuous nucleotides that can be deleted from the sequence of SEQ ID NO: 1 is preferably a sequence encoding either of or both the stalk domains, either of the head domains, or either of the neck domains, and one or a plurality thereof. In the aforementioned domains, deletion of the region encoding the entire region from the head domain to the stalk domain that is located more closely to the amino terminus (i.e., nucleotide positions 322 to 8898) or the region encoding the entire region from the head domain to the stalk domain that is located more closely to the carboxyl terminus (i.e., nucleotide positions 8989 to 10611) is more preferable. Further preferably, a plurality of repeated regions observed in the coding region of the stalk domain are deleted in such a manner that each region appears only once without repetition. Most preferably, any one of the plurality of repeated regions observed in the coding region of the stalk domain is deleted.

By introducing a DNA encoding autotransporter adhesin with a DNA of the nucleotide sequence as shown in SEQ ID NO: 3 into a target microorganism, nonspecific adhesive property and/or autoagglutinating property of the target microorganism can further be improved. DNA of the nucleotide sequence as shown in SEQ ID NO: 3 has homology with the OmpA gene of the outer membrane protein of Acinetobacter bacteria, and it thus encodes the outer membrane protein. A gene functionally equivalent to DNA comprising the nucleotide sequence as shown in SEQ ID NO: 3 may be introduced. An example of DNA that is functionally equivalent to DNA comprising the nucleotide sequence as shown in SEQ ID NO: 3 is DNA comprising a nucleotide sequence having 90% or more, preferably 95% or more, and more preferably 98% or more homology to the nucleotide sequence as shown in SEQ ID NO: 3. Another example is DNA hybridizing under stringent conditions to DNA comprising a nucleotide sequence complementary to the nucleotide sequence as shown in SEQ ID NO: 3.

An operon comprising a DNA encoding autotransporter adhesin derived from a microorganism having nonspecific adhesive property may be introduced into a target microorganism. For example, DNA comprising the nucleotide sequence as shown in SEQ ID NO: 5 may be introduced into the target microorganism, so that DNA encoding autotransporter adhesin and DNA encoding the outer membrane protein can be introduced into the target microorganism. An operon that is functionally equivalent to the above operon may be introduced. An example of a functionally equivalent operon is an operon comprising DNA comprising a nucleotide sequence having 70% or more, preferably 80% or more, more preferably 90% or more, further preferably 95% or more, and most preferably 98% or more homology to the nucleotide sequence as shown in SEQ ID NO: 5 and having activity of providing or enhancing nonspecific adhesive property and/or autoagglutinating property for a host microorganism.

Target microorganisms into which DNA encoding autotransporter adhesin is to be introduced include, but not particularly limited to, microorganisms with weak or without nonspecific adhesive property and/or autoagglutinating property. Examples include: bacteria of the genus *Escherichia*, such as *Escherichia coli*; bacteria of the genus *Acinetobacter*, such as *Acinetobacter calcoaceticus*; bacteria of the genus *Ralstonia*, such as *Ralstonia eutropha*; bacteria of the genus *Pseudomonas*, such as *Pseudomonas putida* and *Pseudomonas fluorescens*; bacteria of the genus *Aeromonas*, such as *Aeromonas caviae*; bacteria of the genus *Alcaligenes*, such as *Alcaligenes latus*; and bacteria of the genus *Xanthomonas*, such as *Xanthomonas campestris*.

By introducing a DNA encoding autotransporter adhesin into a target microorganism through transformation, a microorganism for which nonspecific adhesive property and/or autoagglutinating property have been provided or enhanced can be obtained. Typically, a DNA encoding autotransporter adhesin is ligated to an adequate vector, and a target microorganism (i.e., a host microorganism) is transformed with such vector to produce a microorganism for which nonspecific adhesive property and/or autoagglutinating property have been provided or enhanced. Specifically, multiple copies of the aforementioned DNA may be introduced into the host microorganism, such DNA may be ligated under the control of a constitutive expression promoter, or such DNA may be ligated under the control of a promoter in inducible enzyme systems, to produce a microorganism for which nonspecific adhesive property and/or autoagglutinating property have been provided or enhanced. The same applies to a case in which a DNA encoding the outer membrane protein is introduced with a DNA encoding autotransporter adhesin and to a case in which an operon comprising a DNA encoding autotransporter adhesin is introduced.

At the outset, DNA of interest is ligated to a vector to prepare a recombinant vector. As the vector, a phage, cosmid, artificial chromosome, or plasmid vector that can autonomously replicate in a host cell can be used. When a plasmid is introduced into a chromosome as an expression cassette, for example, a vector must be capable of autonomous replication in a host, which is necessary for constructing such expression cassette (e.g., *E. coli*), but a vector is not necessarily capable of autonomous replication in a host into which the expression cassette is to be introduced (e.g., a yeast host). As such recombinant vector, for example, a shuttle vector that is designed to be used in *E. coli*, and yeast hosts can also be used.

Examples of plasmids include *E. coli*-derived plasmids (e.g., pET21a(+), pET32a(+), pET39b(+), pET40b(+), pET43.1a(+), pET44a(+), pKK223-3, pGEX4T, pUC118, pUC119, pUC18, and pUC19), *Bacillus subtilis*-derived plasmids (e.g., pUB110 and pTP5), yeast-derived plasmids (e.g., YEp13, YEp24, and YCp50), plasmids for the yeast *Pichia pastoris* (e.g., pPICZ, pPICZα, pHIL-D2, pHIL-S1, pPIC9, pPIC6, pGAPZ, pPIC9K, pPIC3.5K, pAO815, and pFLD), and λ phages such as phage DNA (e.g., λgt11 and λZAP). In addition, animal virus vectors, such as vaccinia virus vectors, and insect virus vectors, such as baculovirus vectors, can be used. Further, a commercially available cloning vector, such as pCR4-TOPO®, may be used for cloning and sequencing.

In order to insert DNA into a vector, purified DNA is first cleaved with an adequate restriction enzyme and inserted into a restriction enzyme site or multicloning site of an adequate vector DNA to ligate DNA of interest to the vector. For example, DNA of interest can be synthesized by a conventional technique. For the purpose of incorporating such DNA into a vector, the DNA may be amplified via PCR with primers, such that the resultant comprises the cleavage sites with adequate restriction enzymes at both ends. PCR conditions can be adequately determined by a person skilled in the art.

In addition to a promoter and DNA of the present invention, a cis element such as an enhancer, a splicing signal, a poly A addition signal, a selection marker, a ribosome binding sequence (an SD sequence), or the like may be ligated to the recombinant vector according to need. Examples of selectable markers include, but are not limited to, drug-resistant markers, such as kanamycin, ampicillin, tetracycline, and chloramphenicol, and auxotrophic markers, such as leucine, histidine, lysine, methionine, arginine, tryptophan, and uracil.

Promoters are not particularly limited, and a person skilled in the art can select adequate promoters in accordance with host microorganisms. When K coli hosts are used, for example, T7 promoters, lac promoters, trp promoters, or λ-PL promoters can be used. In addition, a promoter comprising the nucleotide sequence as shown in SEQ ID NO: 28 and a promoter that is functionally equivalent thereto, such as a promoter comprising a nucleotide sequence having 90% or more, preferably 95% or more, and more preferably 98% or more homology to the nucleotide sequence as shown in SEQ ID NO: 28, can be preferably used.

In order to ligate a DNA fragment to a vector fragment, a known DNA ligase is used. The DNA fragment is annealed to the vector fragment, followed by ligation to prepare a recombinant vector. Preferably, a recombinant vector can be obtained by performing a ligation reaction with the use of a commercially available ligation kit, such as Ligation High (TOYOBO Co., Ltd.) under the indicated conditions.

Recombinant DNA techniques including cloning, ligation, PCR, or the like, described in, for example, Sambrook, J. et al., Molecular Cloning 2nd ed., 9.47-9.58, Cold Spring Harbor Lab. Press, 1989 and Short Protocols In Molecular Biology, Third Edition, A Compendium of Methods from Current Protocols in Molecular Biology, John Wiley & Sons, Inc. may be employed.

According to need, the obtained vector may be purified via the boil method, an alkali SDS method, or the magnetic bead method, or with the use of commercially available kits based on the principles of such methods. Further, the vector may be concentrated via a means such as ethanol precipitation or polyethylene glycol precipitation.

A recombinant vector may be introduced into a target microorganism by any method without particular limitation. Examples include a method involving the use of calcium ions, electroporation, and lipofection.

A transformed microorganism comprising DNA of interest can be selected with the aid of a marker gene in the recombinant vector. For example, a transformed microorganism of interest can be selected by forming colonies on an LB agar medium plate comprising antibiotics such as ampicillin or kanamycin. In order to verify whether or not a cloned host microorganism has been transformed by a recombinant vector, a sample from the microorganism may be subjected to verification of amplification of the insert via PCR or sequence analysis by the dideoxy method using a sequencer. In addition to the introduction of an autonomously replicable plasmid, chromosomal integration may be carried out by positioning a region homologous to the chromosomal gene in a vector to induce homologous recombination, thereby introducing the target gene.

The obtained transgenic microorganism is cultured in a medium by a method that is commonly used for culture of the target microorganism. A natural or synthetic medium may be used for culturing the transgenic microorganism obtained from a microbial host, such as E. coli or yeast, provided that such medium comprises carbon sources, nitrogen sources, inorganic salts, and the like assimilable by the microorganism and such medium can efficiently culture the transgenic microorganism. Specific examples include M9 medium, M9G medium, BS medium, LB medium, nutrient broth medium, meat extract medium, SOB medium, SOC medium, and PDA medium.

Any assimilable carbon compounds can be used as carbon sources. Examples of carbon compounds that can be used include: saccharides such as glucose; polyols such as glycerin; alcohols such as methanol; and organic acids such as pyruvic acid, succinic acid, and citric acid. Any nitrogen compounds can be used as nitrogen sources. Examples thereof that can be used include peptone, meat extract, yeast extract, casein hydrolysate, an alkaline extract of soy bean cake, alkylamines such as methylamine, and ammonia or a salt thereof. In addition, phosphate, carbonate, salts of sulfate, magnesium, calcium, potassium, iron, manganese, and zinc, given amino acids, given vitamins, antifoaming agents, or the like may be used according to need. Further, an inducer of protein expression, such as isopropyl-β-D-thiogalactopyranoside, may be added to a medium according to need.

In general, culture is conducted under aerobic conditions, such as shake culture or aeration and agitation culture conditions, at preferably 0° C. to 40° C., more preferably 10° C. to 37° C., and particularly preferably 15° C. to 37° C. During culture, the pH level of the medium can be adequately changed, provided that a host can grow therein and the activity of autotransporter adhesin is not deteriorated. The pH level is preferably between about 4 and 8. The pH level is adjusted with the use of an inorganic or organic acid, an alkaline solution, or the like. If necessary, antibiotics such as ampicillin or tetracycline may be added to the medium during the culture.

Thus, a microorganism for which nonspecific adhesive property and/or autoagglutinating property have been provided or enhanced can be obtained. Nonspecific adhesive property of the resulting microorganism can be evaluated by the aforementioned adhesion test via crystal violet staining (the CV adhesion test), and autoagglutinating property can be evaluated in the following manner, for example. Specifically, the bacterial cell liquid culture is centrifuged, the culture supernatant is removed, inorganic salt medium is added to the cell pellet, the cell suspension is obtained via ultrasonication, the turbidity ($OD_{660}$) of the cell suspension is adjusted to a constant level with a medium, and this $OD_{660}$ value is defined as the initial $OD_{660}$ value. The cell suspension in a glass centrifuge tube is allowed to stand at room temperature, resulting in the sedimentation of aggregated cells, and changes over time in the $OD_{660}$ values in the supernatant are assayed. A microorganism exhibiting a decrease in the $OD_{660}$ value relative to the initial $OD_{660}$ value of 10% or more, preferably 15% or more, and more preferably 20% or more can be evaluated as having autoagglutinating property.

The resulting microorganisms are cultured, and bacteria or cells are then disrupted by a known technique, such as a mechanical technique, an enzymatic technique involving the use of lysozyme, or chemical processing with e.g., a surfactant. Thus, autotransporter adhesin proteins can be isolated.

The present invention can be directly applied within the conventional fermentation industry or for waste treatment. In addition, the present invention is very effective for biomass energy production and green biotechnology involving the use of microbial cells. In particular, it is desirable to carry out production of energy or chemical products at low cost. Provision or enhancement of nonspecific adhesive property and/or autoagglutinating property for a microorganism leads to immobilization or aggregation of cells of the microorganisms, which directly leads to promotion of production efficiency and serves as a foundation for the development of the aforementioned industries.

EXAMPLES

Example 1

Analysis of an Adhesion-Associated Gene 1-1: Preparation of the Less-Adhesive Mutant T1 and Primers Used for Inverse PCR In order to analyze an adhesion-associated gene from *Acinetobacter* sp. strain Tol 5, less-adhesive mutants were produced via random transposon insertion. Tol 5 WT strain (Tol 5 wild-type strain) as the recipient cells were conjugated with *E. coli* S17-1 strain having transposon vector as the donor cells at 28° C. for 22 to 24 hours. Selection was performed on a medium containing toluene and tetracycline, and the obtained cells were subjected to an adhesion test. As a result, several strains exhibiting less adhesive property were obtained. Genomic DNAs thereof were obtained and treated with the HindIII restriction enzyme, and Southern hybridization was carried out using the resultants as templates and DIG-labeled tetA as a probe. As a result, an intensive band was detected at around 5 kb in one strain, and this strain was designated as the less-adhesive strain, T1. The surface structure of the T1 strain was observed under an electron microscope, and it was found to lack appendages (i.e., cell surface projections).

Subsequently, a DNA fragment of approximately 5 kb, which was detected via Southern hybridization, was excised from agarose gel in order to analyze the transposon insertion site of the T1 strain. This fragment was designated as T1-5 kb. T1-5 kb was inserted into the pUC118 vector and the resultant was cloned in *E. coli* DH5α. Both ends of the insert portion in the resulting plasmid DNA were sequenced. As a result, a 68-bp nucleotide sequence from the Tol 5 WT strain was found (SEQ ID NO: 6), in addition to the Tn5 sequence, in T1-5 kb.

1-2: Cloning of the Adhesion-Associated Gene

In order to analyze the nucleotide sequence of the transposon insertion site in the less-adhesive mutant, T1, inverse PCR of chromosomal DNA of the WT strain was performed on the basis of the 68-bp sequence of the insertion site, which had become apparent via analysis of T1. At the outset, the Tol 5 wild-type strain was cultured in BS medium, followed by extraction of DNA and treatment with RNase. The obtained genomic DNA was treated with restriction enzymes, other than Hind III, of which sites were present in the pUC118 multicloning site (i.e., Acc I, Hae III, Hinc II Kpn I, Pst I, Pvu II Sal I, Sau3AI, Sma I, or Xba I) and verified via agarose gel electrophoresis (hereafter referred to as "E.P."). The restriction enzyme Hind III was excluded from the step because the Hind III site was found within the 68-bp sequence when it was used for analyzing T1 and thus use of Hind III was considered to be inappropriate for obtaining a target region. Based on the results of E.P., some enzymes of which bands remained at positions of high molecular weights equal to that of the genome were determined to be not appropriate because it appears that there are not a sufficient number of restriction enzyme reaction sites of the enzymes and thus resulting fragments are too long. Also, enzymes of which bands exhibiting low molecular weights were observed were also determined to be not appropriate because resulting fragments are too short and thus sequencing thereof would provide only a little sequence information. As a result, Hinc II that showed signals between 1,500-bp to 5,000-bp was selected. The genomic DNA was treated with Hinc II (Tol 5/Hinc II). Tol 5/HincII, which had been subjected to DNA purification, was ligated to cause self-ligation (self-cyclization) (Tol 5/HincII/circular). Subsequently, inverse PCR was carried out using the resultant as a template. Primers with the Hinc II linker were used herein for the ligation into a Hinc II-treated vector. The conditions used are described below. The resultant 5-kb PCR product was designated as Tol 5-5 kb.

Inverse PCR Conditions
Polymerase: KOD-plus-
Template DNA: Tol 5/HincII/circle
Primer F: T1-5 kb R3
Primer R: T1-5 kb RC
Annealing: 66° C.
Extension: 5 Minutes The resultant PCR product was purified and treated with the restriction enzyme Hinc II. This treatment is intended to shorten the fragment for the purpose of improving the success rate of cloning and to cleave the linker with Hinc II. DNAs were extracted from agarose gel so as to obtain separately samples of the fragments (QIAquick Gel Extraction Kit). The resultant 2.8-kb fragment and 1.8-kb fragment were designated as Tol 5-2.8 kb and Tol 5-1.8 kb, respectively. Tol 5-2.8 kb and Tol 5-1.8 kb were ligated into vectors. Thereafter, transformation was carried out (via a chemical procedure; blue/white colony selection). White colonies were picked up and cultured in LB liquid medium. Thereafter, small-scale extraction of plasmid DNA was performed. Plasmid DNA was treated with the restriction enzyme. Hinc II, and confirmed via E.P. As a result of restriction enzyme treatment, bands of the vector plus 2.8 kb and 1.8 kb were ideally obtained. The size and the orientation of the insert fragment were verified via PCR. The conditions used are shown below.

PCR Conditions
Polymerase: Blend Taq
Template DNA: Tol 5-1.8 kb, Tol 5-2.8 kb
Primer F: T1-5 kb R3, pUC118F
Primer R: T1-5 kb RC, pUC118R
Annealing: 62° C.
Extension: 2 Minutes As a result of PCR, regarding Tol 5-2.8 kb, a 2.8-kb fragment was amplified with the use of the primer pair of pUC118R and T1-5 kb R3 and, regarding Tol 5-1.8 kb, a 1.8-kb fragment was amplified with the use of the primer pair of pUC118F and T1-5 kb RC. Based on such results, the size of the inserted fragment was confirmed, and the orientation of fragment insertion was determined. These 2 strains were subjected to sequencing via a primer-walking method. However, the sequencer signal was disordered, and computational assembly also yielded the problem of inconsistent nucleotides at sites that were considered to be the overlapping regions. As a result of analysis, a plurality of long repeat sequences were found in the sequences. This also results in the problem that the lengths of the assembled sequences were less than those of the insert fragments of interest; i.e., 2.8 kb and 1.8 kb. Thus, primer designing and sequencing were repeated and, consequently, nucleotide sequences corresponding to the length of the insert fragments were determined. Because of such repeat sequences, however, reliability of the results was insufficient. In order to enhance the certainty of sequencing, accordingly, we attempted to directly clone Tol 5-5 kb for sequencing it again. In order to perform TA cloning, Taq-based DNA polymerase Easy-A exhibiting high accuracy was used to perform PCR to amplify Tol 5-5 kb. PCR conditions used are shown below.

PCR Conditions
Polymerase: Easy-A High-Fidelity PCR Cloning Enzyme
Template DNA: Tol 5/Hinc II/circular
Primer F: T1-5 kb R3-2
Primer R: T1-5 kb RC-2
Annealing: 67.9° C.
Extension: 5 Minutes TA cloning was carried out using the resultant PCR product. Transformation was carried out via a chemical procedure and the resultants were spread on LB/Km agar medium. Colonies were cultured in LB/Km liquid medium, and after culturing, plasmid DNA was extracted. In order to verify the insert, the DNA was treated with the restriction enzyme EcoRI. As a result, the existence of the vector and a 5-kb fragment was observed. Further, the size of the insert fragment was confirmed via PCR. The conditions are shown below.

PCR Conditions
Polymerase: Blend Taq
Template DNA: Tol 5-5 kb plasmid No. 5
Primer F: pUC118F
Primer R: pUC118R
Annealing: 65° C. to 71° C.
Extension: 5 Minutes As a result of PCR, a 5-kb band of the insert was observed and it was subjected to sequence analysis. Sequencing was carried out by the primer walking method again, which was still very difficult because of the repeat structure. Based on the aforementioned sequence information of the 1.8-kb and 2.8-kb fragments, primer designing and sequencing were carefully repeated, and a 4,907-bp sequence having a gigantic repeat structure was obtained as a result of a laborious and time-consuming procedure. The Tol 5-2.8 kb sequence and the Tol 5-1.8 kb sequence were completely consistent with the sequences of Tol 5-5 kb. Thus, the accuracy of sequencing was improved. The obtained Tol 5-5 kb sequence is shown in SEQ ID NO: 7. Based on this sequence, the translated proteins were subjected to homology search via BLAST. As a result, a 4,026-bp ORF exhibiting 20% to 30% homology to the autotransporter adhesin, of which the sequence has been reported in other bacteria, was found, and transposon was found to have been inserted into this ORF. Thus, the existence of ORF associated with high adhesive property and appendage production of the Tol 5 strain was demonstrated. This ORF was, however, discontinued at the 3' end of Tol 5-5 kb, which necessitated further cloning of a downstream region following Tol 5-5 kb, in order to elucidate the entire ORF. Even if autotransporter adhesin associated with bacteria adhesion was hit via homology search, homology was low, and the membrane anchor domain at the carboxyl terminus, which defines this group, did not appear. Thus, it could have been another protein having a partially similar sequence.

In order to obtain sequential information of further downstream regions based on the resulting sequence, the southern hybridization was carried out in an attempt to obtain a target fragment. In order to prepare a DIG-labeled probe, primers were designed while avoiding the repeat portion. With the use of the primers and chromosomal DNA of the Tol 5 strain as a template, a target band of 160 by was amplified. PCR conditions used are shown below.

PCR Conditions
Polymerase: Blend Taq
Template DNA: Tol 5 genome
Primer F: Tol 5-ad-probe2F
Primer R: Tol 5-ad-probe2R
Annealing: 66° C. to 72° C.
Extension: 1 Second Since a plurality of bands were amplified, it was deduced that the probe sequence portions without repetition in the portion analyzed above have further repeats in a downstream region that had not been analyzed. In order to advance sequencing, the 160-bp target band alone was excised from it with the use of the QIAquick Gel Extraction Kit. The resultant was used as a template to prepare a probe via PCR. PCR conditions used are shown below.

PCR Conditions
PCR DIG Probe Synthesis Kit
Template DNA: Tol 5 160 bp probe Gel Extraction
Primer F: Tol 5-ad-probe2F
Primer R: Tol 5-ad-probe2R
Annealing: 67.9° C.
Extension: 2 Minutes The products of digestion of chromosomal DNAs of the Tol 5 strain with a variety of restriction enzymes were subjected to southern hybridization with the use of the resulting probes. As a result, signals representing probe hybridization were detected at 3 kb and 2.3 kb of the digestion product with the Pst I restriction enzyme. These two DNA fragments were excised from agarose gel and extracted (QIAquick Gel Extraction Kit). The resultant fragments were designated as Tol 5-3 kb and Tol 5-2.3 kb. The excised DNA was ligated to Pst I-digested pUC118. The resultant recombinant vector was used to transform *E. coli* DH5α (a chemical procedure; blue/white colony selection). In addition, colony hybridization was carried out to select transformants into which such fragments had been introduced. As a result, signals were observed only in the colonies into which Tol 5-3 kb had been introduced. Colonies in which signals were observed (i.e., Tol 5-CC, -C1, -C2, and -C3) were picked up and cultured in LB/Amp liquid medium, and small-scale extraction of plasmid DNA was performed. The resultants were each treated with the Pst I restriction enzyme. The resultants were subjected to southern hybridization, and signals were detected in Tol 5-CC, -C2, and -C3. These colonies were subjected to DNA sequencing. As a result of sequencing of the both ends of the inserts, there was no fragment, which was consistent with a known sequence. In addition, these sequences were different from each other. That is, cloning of a downstream region of the 5-kb region (Tol 5-5 kb), the nucleotide sequence of which had been determined in advance, failed. The cause thereof could not be identified at this time. However, the present inventors considered that the problem existed due to the following point. That is, they had unwillingly selected a signal from among a plurality of signals detected via southern hybridization with the use of chromosomal DNA of the Tol 5 strain as a template, wherefrom the fragment containing such signal was excised, and then designed the probe based on the fragments. Thus, these clones were temporarily set aside, and acquisition of a fragment that would follow Tol 5-5 kb was attempted.

pUC118::Tol 5-5 kb plasmid DNA was used as a template instead of the Tol 5 chromosomal DNA to prepare a novel DIG-labeled probe via PCR. Since this plasmid contains only one probe region, it was considered that only one amplification product labeled with DIG is produced. PCR conditions used are shown below.

PCR Conditions
PCR DIG Probe Synthesis Kit
Template DNA: pUC118::Tol 5-5 kb plasmid DNA
Primer F: Tol 5-ad-probe2F
Primer R: Tol 5-ad-probe2R
Annealing: 68° C.
Extension: 2 Minutes As expected above, only one amplified fragment having the target size (i.e., 160 bp) was found. New probes with high purity were successfully prepared. With the use of this probe, the plates obtained after the transformation with the use of the aforementioned vector comprising Tol 5-3 kb and Tol 5-2.3 kb were subjected to colony hybridization. Colonies that were deduced to have emitted signals were picked up, cultured on the plate, and then subjected to colony hybridization again for verification. Colonies in which signals were detected (i.e., clones No. 3 (3 kb) and Nos. 6, 12, 13, 21, and 22 (2.3 kb)) were picked up and cultured in LB/Amp liquid medium, and small-scale extraction of plasmid DNA was performed. The resultant plasmid DNA was treated with the Pst I restriction enzyme. As a result, plasmids were found to comprise target fragments of 3 kb (No. 3) or 2.3 kb (Nos. 6, 12, 13, 21, and 22), and all such insert fragments were found to have hybridized with the 160-bp probe. If these fragments comprise downstream regions that follow Tol 5-5 kb as expected, such fragments should comprise a nucleotide sequence of about 1.5 kb sandwiched between the Pst I site and the Hinc II site, as a region overlapping with Tol 5-5 kb. If the aforementioned plasmid, in which such fragment has been inserted into the Pst I site of the multicloning site, is digested with the restriction enzyme Hinc II, accordingly, a DNA fragment of about 1.5 kb resulting from the addition of a very small part of the multi-cloning site to the 1.5-kb overlapped fragment should be obtained. Plasmids Nos. 3, 6, and 22 were digested with Hinc II and roughly-1.5-kb DNA fragments were obtained therefrom. However, the sizes thereof were somewhat different from each other. Among them, Plasmid No. 6 were subjected to sequencing at first. Plasmid No. 6 was cut into a 3.3-kb fragment, which is considered to comprise a 3.1-kb vector fragment, and a 600-bp fragment, in addition to the 1.5-kb fragment. Based on the result of sequencing or southern hybridization that had been carried out previously, it was considered that sequencing of the plasmid may not be accurately conducted via primer walking, which is a well-established high-throughput technique at present, since the plasmid comprises many repeat sequences and thus may cause annealing to a plurality of sites. In addition, it was deduced to have problems in the computational sequence assembly. That is, difficulty, which was experienced in the case of Tol 5-5 kb, might recur. Thus, production of a series of deletion mutants was to be carried out instead of primer walking, although such procedure is laborious and time-consuming. In order to prepare mutants by successively deleting the 2.3-kb Tol 5 DNA fragment inserted in No. 6 from the aforementioned 1.5-kb overlapping fragment, the plasmid was treated with Sac I for a 3' protruding end and Xba I for a 5' protruding end, followed by digestion with exonuclease III. By preparing a series of samples by differentiating the duration during which exonuclease III would be allowed to react, deletion products with different lengths of deletion were obtained. Thereafter, blunt ending with the use of Mung Bean Nuclease and end repair with the use of the Klenow fragment were further carried out, and the samples were subjected to blunt end ligation in the end to obtain a series of deletion plasmids. After purification via ethanol precipitation, the samples were treated with Xba I, which should have disappeared due to digestion with exonuclease III, to eliminate the influence by unreacted plasmids, and *E. coli* DH5α was transformed with this DNA to obtain a series of deletion mutants. Many transformed colonies were picked up and cultured, and the extracted plasmids were digested with the restriction enzyme Hinc II. By taking the size of a sequencing path (800 by or longer) into consideration, deletion mutants were selected at adequate intervals, and they were sequenced. The 2,280-bp nucleotide sequence was determined by assembling the sequencing results. The determined sequence is shown in SEQ ID NO: 8 (Tol 5-No. 6). Tol 5-No. 6 comprises a sequence of about 1.5 kb overlapping with Tol 5-5 kb, and thus a nucleotide sequence of about 750 by following Tol 5-5 kb was determined based thereon. Thus, ORF encoding to the aforementioned protein exhibiting low homology to the autotransporter adhesin was extended to as long as 4,707 bp, and the amino acid sequence of the protein encoded thereby contained 1,569 residues. However, the ORF had not yet been terminated, and the sequence was discontinued at the 3' end. This necessitated further cloning of a downstream region following Tol 5-No. 6. In addition, the sequence exhibited the highest homology to EmaA of *Actinobacillus actinomycetemcomitans*, but it was as low as 26% homology at the amino acid level. Further, it had not yet reached the coding region of the membrane anchor domain. Thus, the corresponding protein was not concluded to be a protein of the TAA family. In any case, it was deduced that a protein encoded by the adhesion-associated gene, which had been destroyed via transposon insertion, was a novel adhesive protein which was very large and in which long-repeat sequences were arranged in a complex manner.

In order to obtain sequential information on the downstream following Tol 5-No. 6, a 158-bp probe was produced via PCR using the plasmid containing Tol 5-No. 6 as a template, which had been designed based on the sequence newly determined with avoiding a repeat sequence. PCR conditions used are shown below.

PCR Conditions
PCR DIG Probe Synthesis Kit
Template DNA: pUC118::Tol 5-No. 6
Primer F: Tol 5-ad-probe5F
Primer R: Tol 5-ad-probe6R
Annealing: 65° C.
Extension: 2 Minutes The restriction enzyme Hind III site existed in a region immediately upstream of the synthesized probe region. Thus, chromosomal DNA of Tol 5 was digested with Hind III, subjected to E.P., and then subjected to southern hybridization with the use of a 158-bp probe. As a result, three signals were observed again, all the signal portions were excised from agarose gel, and DNAs were extracted (using DEAE papers). The resultants were designated as Tol 5-B (2,500 bp), Tol 5-M (1,200 bp), and Tol 5-S (600 bp) in descending order of molecular sizes. The excised DNA fragments were ligated to Hind III-treated pUC118. After the ligation, DNAs were purified and then transformed (electroporation; blue/white colony selection). The plates on which colonies had been formed were subjected to colony hybridization with the use of the 158-bp probe mentioned above. Colonies in which signals were detected were picked up and cultured in LB/Amp liquid medium. Small-scale extraction of plasmid DNA was performed and it was treated with the restriction enzyme Hind III to verify the length of the insert fragment. As a result, insertion of DNA fragments of the strain Tol 5 of 2,500 bp, 1,200 bp, and 600 by in length was confirmed, and these plasmids were subjected to sequencing. Since the M fragment and the S fragment were short, the nucleotide sequences of 1,185 by and 603 by were determined via single-path sequencing. Deletion mutants were prepared for sequencing of the B fragment. A plasmid containing the B fragment was treated with Sad for a 3' protruding end and Xba I for a 5' protruding end and then digested with exonuclease III. By preparing a series of samples by differentiating the duration during which exonuclease III would be allowed to react, deletion products with different length of deletion were obtained. Thereafter, blunt ending with the use of Mung Bean Nuclease and end repair with the use of the Klenow fragment were carried out, and the samples were subjected to blunt end ligation in the end, to obtain a series of deletion plasmids. After purification via ethanol precipitation, the samples were digested with XbaI, which should have disappeared due to digestion with exonuclease III, to eliminate the influence by unreacted plasmids, and E. coli DH5α was transformed with the resultant DNA to obtain a series of deletion mutants. Many transformed colonies were picked up and cultured, and the extracted plasmids therefrom were subjected to dual digestion with the restriction enzymes HindIII and EcoRI. By taking the size of a sequencing path (800 by or longer) into consideration, deletion mutants were selected at adequate intervals and they were sequenced. The 2,540-bp nucleotide sequence of the B fragment was determined by assembling the sequencing results. The Tol 5-B, Tol 5-M, and Tol 5-S sequences determined are shown in SEQ ID NOs: 9 to 11. The Tol 5-M fragment comprised a 533-bp nucleotide sequence as an overlapping region that is 100% consistent with Tol 5-No. 6. The HindIII fragments, Tol 5-B, -M, and -S fragments, did not comprise overlapping regions from each other, the -M fragment was deduced to follow Tol 5-No. 6, but the positional relationship between the other 2 fragments was not found. These fragments comprised almost the same nucleotide sequence regions, and the 158-bp probe region was located therein. That is, these fragments were also deduced to be parts of a gigantic fragment in which repeat sequences are formed. ORF was extended to as long as 5,358 by because of the overlapping of the Tol 5-M fragment, and the amino acid sequence of the protein encoded thereby comprised 1,785 residues. However, ORF had not yet been terminated, and the sequence was discontinued at the 3' end. This necessitated further elucidation of the nucleotide sequence of a downstream region following the Tol 5-M fragment. Although the sequence exhibited the highest homology to EmaA of *Actinobacillus actinomycetemcomitans* again, which was as low as 25% homology at the amino acid level, it has not yet reached the coding region of the membrane anchor domain. Thus, whether or not the protein of interest belongs to the autotransporter adhesin family is not yet known.

Sequencing of the Tol 5 DNA fragments, i.e., Tol 5-CC and Tol 5-C2, which were obtained via southern hybridization in an attempt to clone the downstream region subsequent to Tol 5-5 kb but were not found to follow Tol 5-5 kb, was attempted again. Since these fragments were deduced to comprise repeat sequences, independent deletion mutants thereof were produced. After the plasmids were treated with Sad for a 3' protruding end and XbaI for a 5' protruding end, a series of deletion mutants were prepared in the same manner as described above, they were sequenced and assembled into a single sequence, and the nucleotide sequences of Tol 5-CC and Tol 5-C2 were determined. The determined Tol 5-C2 and Tol 5-CC nucleotide sequences are shown in SEQ ID NOs: 12 and 13, respectively.

The positional relationship was determined by analyzing sequence overlapping of the Tol 5-B, M, and S fragments and the Tol 5-CC and C2 fragments. Only the sequences exhibiting 100% identity were determined as overlapping sequences. Although three signals were detected via southern hybridization with the use of a 158-bp probe, the results of overlapping analysis and Tol 5-C2 analysis demonstrated that there were in fact four fragments. Since the fourth fragment had almost the same size and sequence as those of Tol 5-S, it existed while overlapping with a signal at around 600 bp. This region was designated as Tol 5-S'. Based on the above, it was found that Tol 5-M, Tol 5-S', Tol 5-S, Tol 5-C2, Tol 5-B, and Tol 5-CC fragments were located in that order while overlapping with each other. As a result, ORF was extended to as long as 10,798 bp, and the amino acid sequence of the protein encoded thereby comprised 3,598 residues. However, ORF was not terminated and discontinued at the 3' end yet. This necessitated further cloning of a downstream region following Tol 5-CC. The sequence exhibited the highest homology to TAA of *Burkholderia phymatum*, but it was as low as 25% homology at the amino acid level. It seemed to contain part of the membrane anchor domain sequence, but it did not comprise the entire sequence. Further, a higher-order structure of such portion could not be predicted. Thus, it could not be concluded that it belonged to the TAA family. Also, the size thereof was found to be much greater than that of BadA of *Bartonella henselae* (3,036 amino acids), which was the largest among members of the TAA family that had been previously reported.

As a result of sequencing that had been conducted as described above, no repeat sequences were observed in the C terminal region of Tol 5-CC. Thus, a 507-bp probe was produced in the C terminal region, and southern hybridization was carried out with the use of DNA of the Tol 5 strain treated with the restriction enzyme Hind III as a template. As a result, a signal was detected at 5 kb and this fragment was designated as Tol 5-05 kb. This DNA was excised from agarose gel and extracted (using the DEAE paper). The extracted DNA fragment was ligated to the Hind III-digested pUC118 vector and subjected to transformation (electroporation; blue/white colony selection). White colonies were picked up and cultured in LB/Amp liquid medium. Plasmid DNA was extracted from bacteria in liquid medium and treated with the restriction enzyme Hind III to verify the insert. It was deduced that Tol 5-05 kb did not contain a repeat structure, and the sequence was determined via primer walking. The determined Tol 5-C5 kb sequence is shown in SEQ ID NO: 14. Tol 5-05 kb was found to overlap with the Tol 5-CC sequence and to be a downstream region following Tol 5-CC. As a result of connection of these fragments, a gigantic ORF as large as 10,893 by (SEQ ID NO: 1) was completed, and a gigantic protein comprising 3,630 amino acids (SEQ ID NO: 2) encoded thereby was elucidated. This is the identity of the gene associated with adhesion which was destroyed via transposon insertion. The positional relationship of the sequence fragments described above is shown in FIG. 1. Thus, the 15,011-bp nucleotide sequence of the gene fragment of the Tol 5 strain comprising a gigantic ORF encoding the protein associated with adhesion was determined.

1-3: Sequence of the Adhesion-Associated Gene

The partial sequences obtained as a result of sequencing of various clones were assembled into a single sequence with GENETYX. Since the gene of interest was found to have many complicated repeat structures, only the sequence portions exhibiting 100% identity were determined to be overlapping sequences when assembling sequences. Whole the nucleotide sequence determined as a result of cloning and sequencing in this example is shown in FIG. 2 and SEQ ID NO: 15.

1-4: Bioinformatic Analysis

It is necessary to identify the region in the nucleotide sequence that encodes a protein. A region encoding a protein was deduced with the use of the ORF finder and GeneMark. As a result, the obtained gene was deduced to comprise four ORFs. Transposon was inserted into the aforementioned gigantic ORF, and a protein encoded by such ORF can be said to be an adhesion factor. Since the termination codons of ORFs at the 5' end and the 3' end are not observed, the ORFs are discontinued in the middle. When encoding a protein, a ribosome binding site and a promoter site are present upstream of the initiation codon. Since sequences thereof are often conserved, the existence of a promoter region for the gigantic ORF of the adhesion-associated gene was searched for. As a result, the presence thereof was verified. The regions are shown below. Thus, the initiation codon at position 949 was deduced to be the correct codon instead of that at position 925.

12 β strands, the β barrel structure is formed in the outer membrane of Gram-negative bacteria, and it functions as a tunnel for protein secretion. The secondary structure was deduced based on the amino acid sequence of the membrane anchor-equivalent region of the adhesion-associated protein of Tol 5, and it was deduced to have 1 α helix and 4 β strands. Based on such deduction and the domain alignment, the adhesion-associated protein of the Tol 5 strain was deduced to be a novel protein of the TAA family, and it was designated as AadA, representing an *Acinetobacter* adhesin. The nucleotide sequence of the aadA gene is shown in SEQ ID NO: 1 and the amino acid sequence of AadA is shown in FIG. 3 and SEQ ID NO: 2. AadA is composed of 3,630 amino acids encoded by a 10,893-bp gene. AadA is a unique member of the TAA family, which have been reported in the past, due to the points below. That is, it is much greater than proteins of the TAA family that have been already reported, the stalk domain comprising a plurality of long-repeat structures that are arranged in a complex manner has low homology to other proteins, and the head domain and the neck domain exist at sites located more closely to the carboxyl terminus at which

```
              -35 region              -10 region
--TATCTCATTTTTTTGATTGCTTTAATTGTATGTAAATTGTTAAATAAAAAAATTGTACATITTATATGCATTGCTA AAGCAGAACCTACTGCCCAAAATGCATCTCCTAAGGAAAAGCGATATGAATAAAATCTACAAAGTGA--
                     925           SD sequence      949  initiation codon
```

ORFs were subjected to homology search with NCBI-BLAST. As a result, there was no protein found to exhibit homology in the entire gigantic protein encoded by the gigantic ORF associated with adhesion. The protein, however, comprised a region exhibiting homology to proteins of the TAA family in one part thereof.

Figure 4:
FIG. 4 shows the results of preparation of multiple alignments of each of the signal peptide, the head domain, the neck domain, and the membrane-anchor domain of autotransporter adhesin with ClustalW for sequence comparison.
Figure 4:
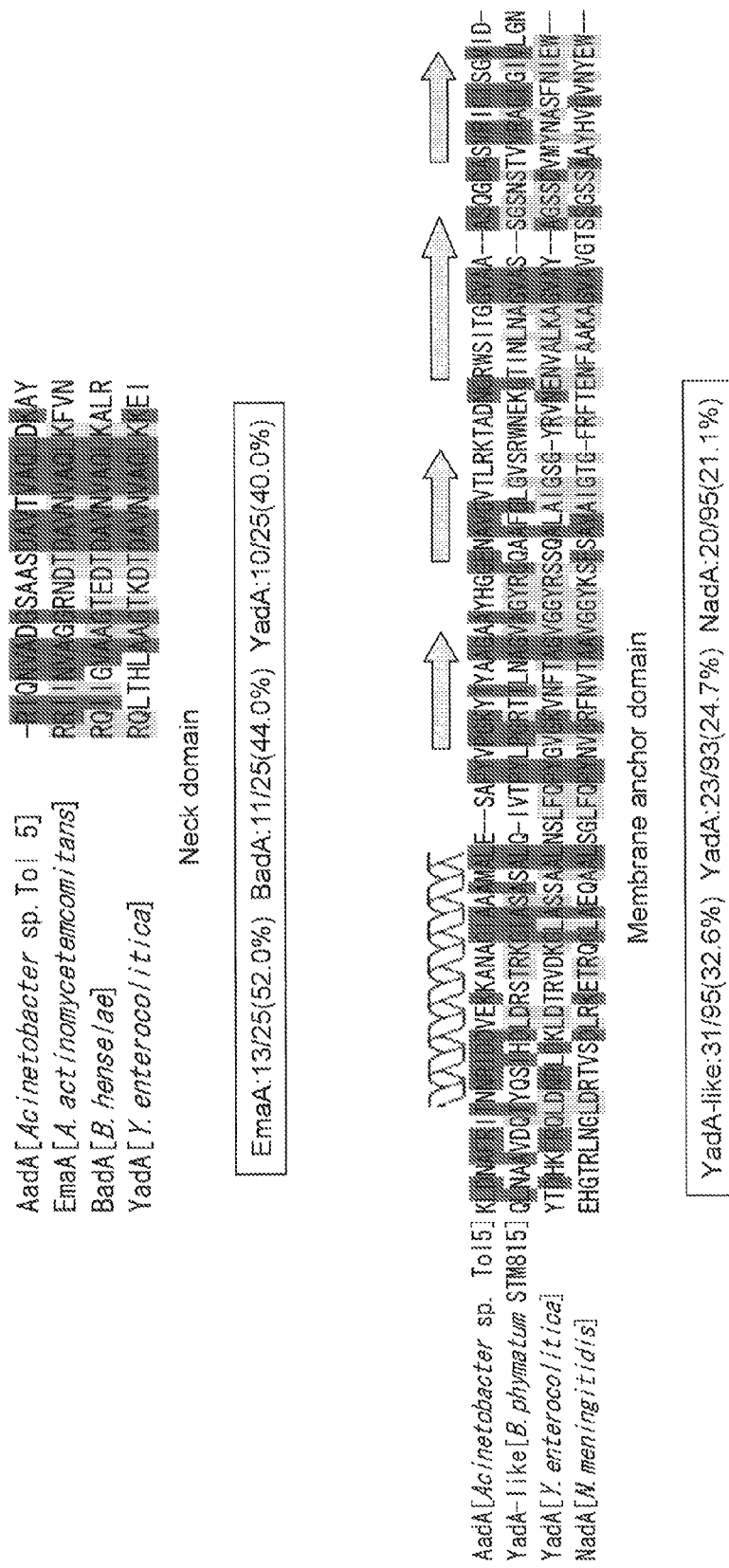

A protein of the TAA family comprises a signal peptide, a head domain, a neck domain, a stalk domain, and a membrane anchor domain. Thus, multiple alignments were prepared for each domain with ClustalW, and the sequence comparisons were performed. The results are shown in FIG. 4. Regarding the membrane anchor domain, the results of prediction of the secondary structure with PredictProtein are also shown. The members of the TAA family were compared. As a result, the sequences of the signal peptide, the head domain, and the neck domain were found to exhibit the highest homology to EmaA of *Aggregatibacter* (*Actinobacillus*) *actinomycetemcomitans*, which were 34%, 44%, and 52%, respectively. In addition, such sequences exhibited 11%, 23%, and 40% homology, respectively, to YadA of *Yersinia enterocolitica*, which has been the most studied protein in the TAA family and can be said to be a prototype of the TAA family. The membrane anchor domain exhibited 48% homology to autotransporter adhesin of *Haemophilus somnus* and 25% homology to YadA. The stalk domain composed of 2,591 amino acids was found to exhibit partial homology to a member of the TAA family via BLAST analysis, although the homology was low. For example, the stalk domain exhibited the highest homology to the YadA-like protein of *Actinobacillus succinogenes*; however, a region composed of only 800 out of 2,591 amino acids exhibited 33% homology to the protein of interest. Thus, a protein of the TAA family was demonstrated to have homology to the domains of the gigantic protein via BLAST analysis, although such homology was not sufficiently high. The most characteristic feature of the TAA family is a conformation of the membrane anchor domain. TAA is a homotrimer, a polypeptide strand has an α helix and 4 β strands, 3 sets of such strands collectively form the membrane anchor domain exists in addition to the amino terminus. Whether or not such specific properties yield high adhesive property or nonspecific adhesive property of the Tol 5 strain is not yet known at present. However, TAA proteins that have been reported in the past function for specifically adhering to host cells or extracellular matrices when pathogenic bacteria infect, and such proteins do not exhibit high adhesive property.

Figure 5:
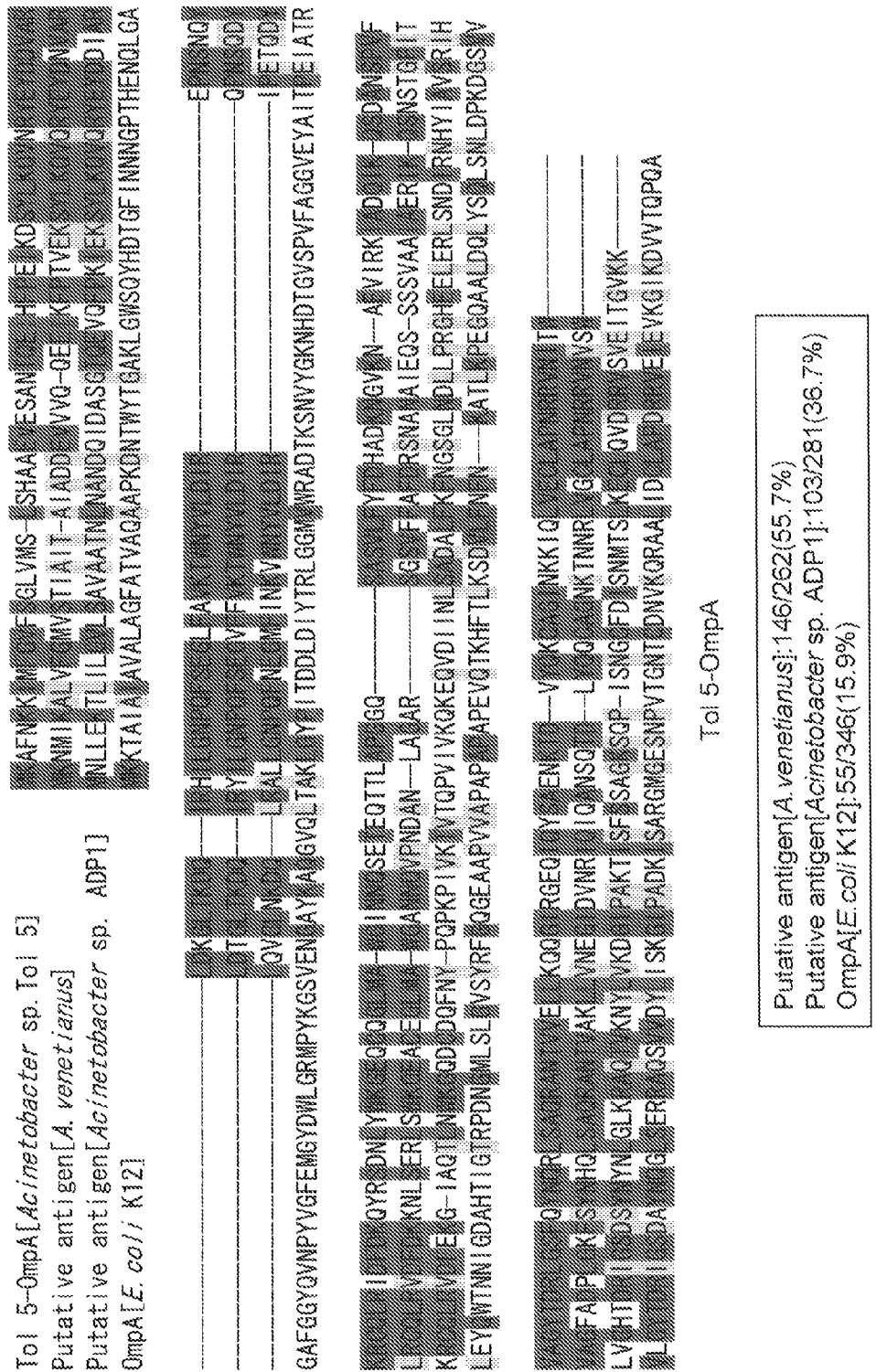
FIG. 5 shows the results of a comparison of the sequence of Tol 5-OmpA and that of an outer membrane protein having homology thereto.

As a result of a homology search of ORF, an ORF of a protein exhibiting homology to the outer membrane protein OmpA of other bacteria of the genus *Acinetobacter* was found immediately downstream of the aadA gene. It was designated as Tol 5-OmpA. The nucleotide sequence of Tol 5-OmpA is shown in SEQ ID NO: 3, and the amino acid sequence thereof is shown in SEQ ID NO: 4. Tol 5-OmpA consists of 264 amino acids encoded by the 795-bp gene. A multiple alignment was prepared using ClustalW, and it was compared with the sequences of the outer membrane proteins exhibiting homology to the Tol 5-OmpA sequence. The results are shown in FIG. 5. In comparison with OmpA of *E. coli*, it exhibits high homology in the C terminal region but exhibits low homology in the N terminal region. In contrast, it exhibits high homology to the entire outer membrane protein of bacteria of the genus *Acinetobacter*. However, functions thereof have not been reported. Since it is adjacent to ORF of AadA, aadA and Tol 5-ompA are highly likely to exist on the same operon. Since it is an outer membrane protein, Tol 5-ompA may also be associated with adhesion or production of adhesive appendages.

An ORF at the 5' end of the 15,011-bp gene fragment of the Tol 5 strain, the nucleotide sequence of which has been determined, exhibited high homology to methionyl-tRNA formyltransferase of, for example, *Acinetobacter* sp. ADP1. An ORF at the 3' end exhibited high homology to dihydroxyacid dehydratase of, for example, *Acinetobacter* sp. ADP 1. Since there is no report that such proteins have functions associated with adhesion, these proteins were deduced to have no association with adhesion in *Acinetobacter* sp. Tol 5.

1-5: Cloning of Full-Length AadA Gene

In order to verify that sequencing had been carried out accurately, full-length aadA comprising a putative promoter site was amplified via PCR, and the length thereof was confirmed. The Tol 5-TKD-F and Tol 5-TKD-R primer regions are shown below.

Primer Tol 5-TKD-F:

```
5'-AATATAGCTTAATTTCAAAAAAATTAAACCAATTGGTTTAAAAGTTA

AAAAAAGTGAAATATATCTCATTTTTTTGATTGCTTTAATTGTATGTAAA

TTGTTAAATAAAAAAAATTGTACATTTTATATGCATTGCTAAAGCAGAAC

CTACTGCCCAAAATGCATCTCCTAAGGAAAAGCGATATGAATAAAATCTA

CAAAGTGATTTGGAATGCGACTTTGTTGGCATGGG-3'
```

Primer Tol 5-TKD-R (Complement):

```
5'--GGCGGTGTAGCTGCAGCGTCTCAAGGCGATGCAAGTGTTCGTATCG

GTATCAGCGGTGTGATTGACTAATTCACTCGACAGGGAAGATCTTCGGGT

CTTCCTTTTTCTTCGAAAATTTTTTAAGAGAGAAAAAATGAAAGCATTTA

ACAAAAAAATTATGTTTGGTGTATTCAGCGGTCTTGTGATGTCATTGAGC

CATGCTGCTGAAGTCGAAAGTGCAAATACGCAAGAA--3'
```

PCR Conditions used are as follows.
PCR Conditions
Polymerase: Easy-A High-Fidelity PCR Cloning Enzyme
Template DNA: Tol 5 genome
Primer F: Tol 5-TKD-F
Primer R: Tol 5-TKD-R
Annealing: 55° C. to 64.5° C.
Extension: 11 Minutes As a result of PCR, a band corresponding to a 11,145-bp sequence (about 11 kb) obtained via cloning and sequencing was obtained, and it was designated as Tol 5-11 kb. Subsequently, TA cloning was carried out using the product. Transformation was carried out via electroporation, and the resultants were spread on LB/Km agar medium. The formed colonies were cultured in LB/Km liquid medium, and after culturing plasmid DNA was extracted. DNA was treated with the EcoR I restriction enzyme in order to verify the insert. It was further confirmed via PCR. The conditions used are shown below.
PCR Conditions
Polymerase: Blend Taq
Template DNA: pCR-XL-TOPO::Tol 5-11 kb plasmid
Primer F: pUC118F
Primer R: pUC118R
Annealing: 56° C. to 68° C.
Extension: 11 Minutes As a result of restriction enzyme treatment, a vector and a band ideal for aadA were clearly observed. Also, a band having the size of aadA was observed as a result of PCR. As a result of sequencing of plasmid DNA, further, the sequences at the both ends of the inserted fragment were completely consistent with the nucleotide sequence, which had been determined in advance. Thus, sequencing accuracy was verified, and the aadA gene (about 11 kb) comprising a putative promoter sequence was satisfactorily cloned.

Further, cloning of a genetic region of about 12,505 by comprising a putative promoter, aadA, and Tol 5-ompA was performed. The fragment was amplified via PCR. The conditions used are as follows.

PCR Conditions
Polymerase: Easy-A High-Fidelity PCR Cloning Enzyme
Template DNA: Tol 5 genome
Primer F: Tol 5-TKD-F
Primer R: Tol 5-ad-op-R3
Annealing: 50° C. to 60° C.
Extension: 14 Minutes The primer Tol 5-ad-op-R3 region used is shown below.

```
5'--TATGATGTGTACATATTTCGACTGATTTATTGCTATATCAGTTTTA

TTTAGCCAGAGTGAATCTGATTCATTTCAAGCTCAAACAATGTNGGAAAT

ACAAATGCCNGACTATCGTTCAAAAACATCGACACATGGAAGAAATATGG

CTGGTGCACGTGGCTTATGGCGTGCAAC--3'
```

The obtained fragment of about 13 kb was designated as Tol 5-13 kb and it was subjected to TA cloning. Transformation was carried out via electroporation, and the resultants were spread on LB/Km agar medium. The colonies were cultured in LB/Km liquid medium and after culturing plasmid DNA was extracted. DNA was treated with the restriction enzyme EcoRI in order to verify the insert. It was further confirmed via PCR. The conditions used are shown below.
PCR Conditions
Polymerase: Blend Taq
Template DNA: pCR-XL-TOPO::Tol 5-13 kb plasmid
Primer F: pUC118F
Primer R: pUC118R
Annealing: 50° C. to 60° C.
Extension: 14 Minutes As a result of restriction enzyme treatment and PCR, a band of the insert having a theoretical length was observed. This plasmid DNA was subjected to sequencing and, consequently, the sequences of the both ends of the inserted fragment were found to be completely consistent with known sequences. Thus, a genetic region comprising a putative promoter, aadA, and Tol 5-ompA; i.e., the genetic region of about 13 kb comprising the 11,858 by aadA-ompA operon (SEQ ID NO: 5), was successfully cloned. In the nucleotide sequence as shown in SEQ ID NO: 5, a region comprising nucleotides 1 to 106 is a promoter-ribosome binding region (SEQ ID NO: 29), a region comprising nucleotides 107 to 10,999 is the aadA gene, and a region comprising nucleotides 11,064 to 11,858 is the Tol 5-ompA gene.

Example 2

Property Evaluation of *E. coli* into which the Adhesion-Associated Gene of the *Acinetobacter* sp. Tol 5 Strain has been Introduced Properties of the *E. coli* DH5α strains transformed with vectors into which the aadA gene and the aadA-ompA operon have been inserted (such strains being designated as DH5α::aadA and DH5α::aadA-ompA) were compared with those of the wild-type *E. coli* DH5α strain (WT) as a control. The *E. coli* DH5α strain transformed with a vector into which the aadA-ompA operon had been inserted was accepted by the Patent Microorganisms Depositary, the Department of Biotechnology, National Institute of Technology and Evaluation, Incorporated Administrative Agency (2-5-8 Kazusakamatari, Kisarazu-shi, Chiba, Japan) as "DH5α-XLTOPO::aadA-ompA" under the provisional accession number: NITE ABP-490 (date of accession: Feb. 19, 2008).

2-1: Morphological Observation Using Optical Microscope

Figure 6:
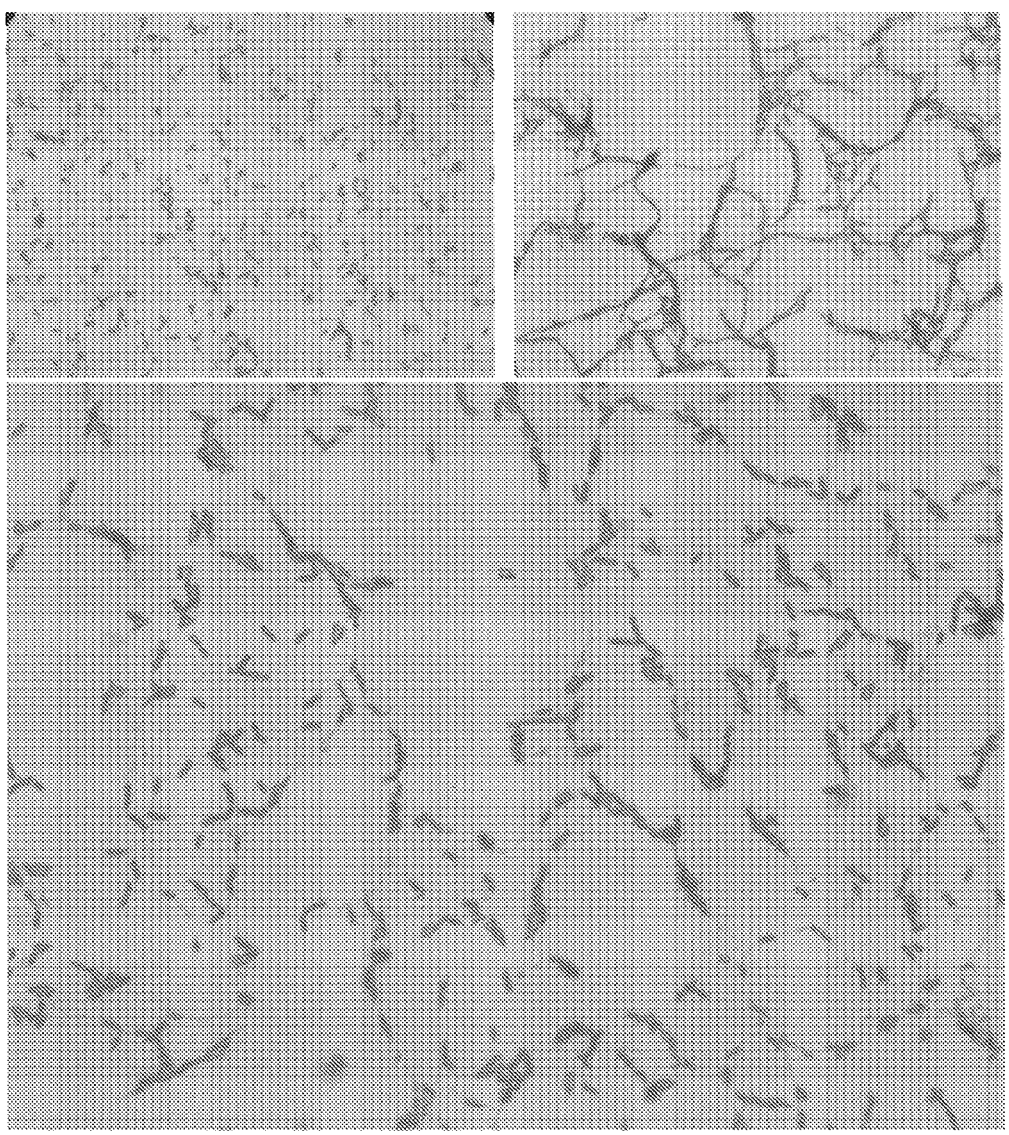
FIG. 6 shows the results of optical microscopic observation of morphological changes resulting from introduction of the aadA gene and the aadA-ompA operon.

In order to observe morphological changes resulting from introduction of the aadA gene and the aadA-ompA operon, 3 types of strains (i.e., DH5α::aadA, DH5α::aadA-ompA, and DH5αWT strains) were subjected to Gram staining, and the stained strains were observed under an optical microscope. The results are shown in FIG. 6.

In the DH5α::aadA-ompA strain into which the aadA-ompA operon had been introduced, filamentous structures that link a bacterial cell to other cells were observed. The filamentous substances that look like extracellular polymers (EPS) are considered to be associated with the addition of adhesion. In the DH5α::aadA strain into which aadA had been introduced, bacterial cells were long and thin, and the cells were linked to each other at their poles. Both transgenic strains were apparently different from the wild-type strain in terms of morphology, which indicates morphological changes resulting from introduction of the adhesion-associated gene.

2-2: Morphological Observation Using Electron Microscope

Figure 7:
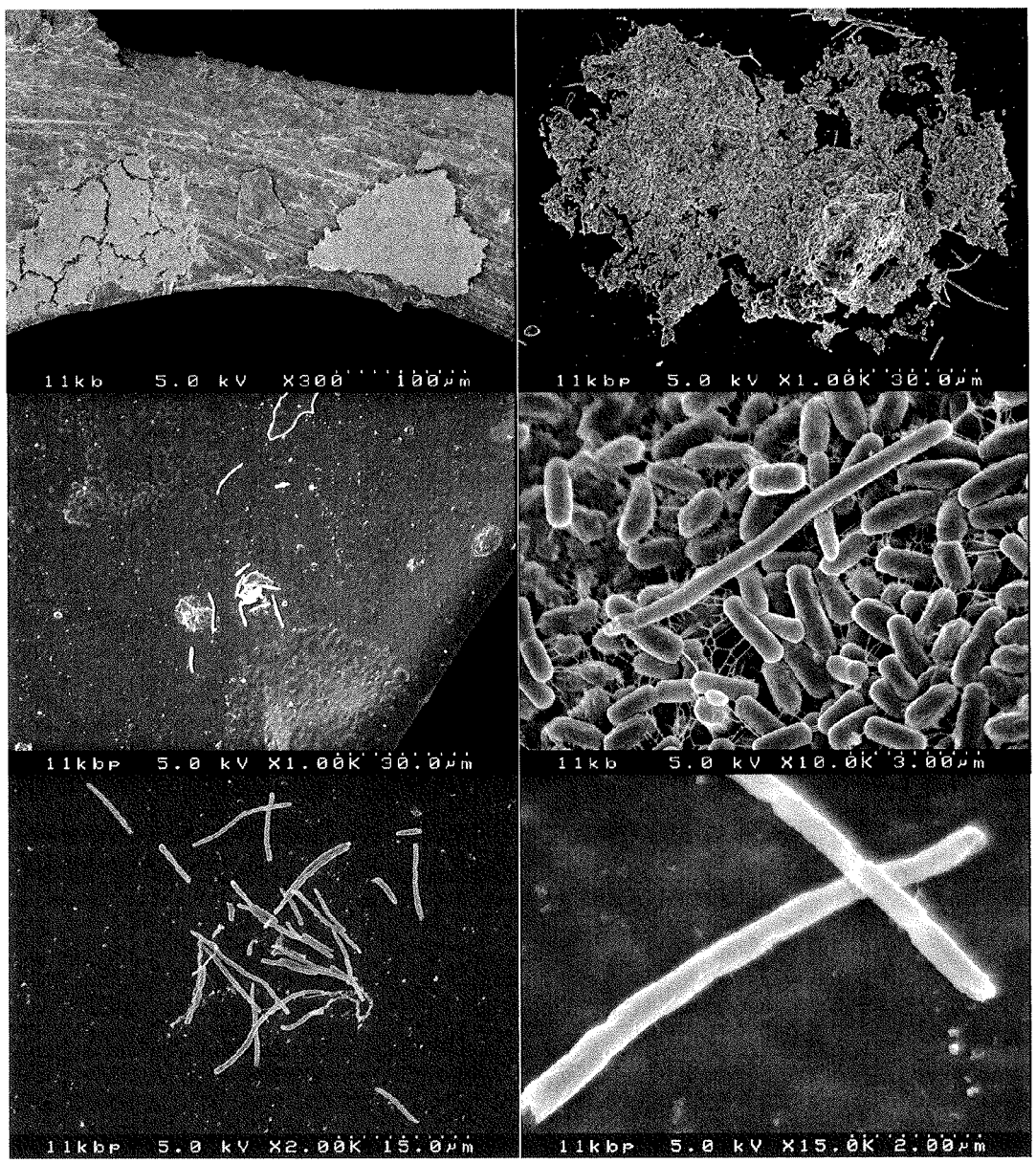
FIG. 7 shows an electron micrograph of DH5α::aadA that has adhered to a polyurethane surface.
Figure 8:
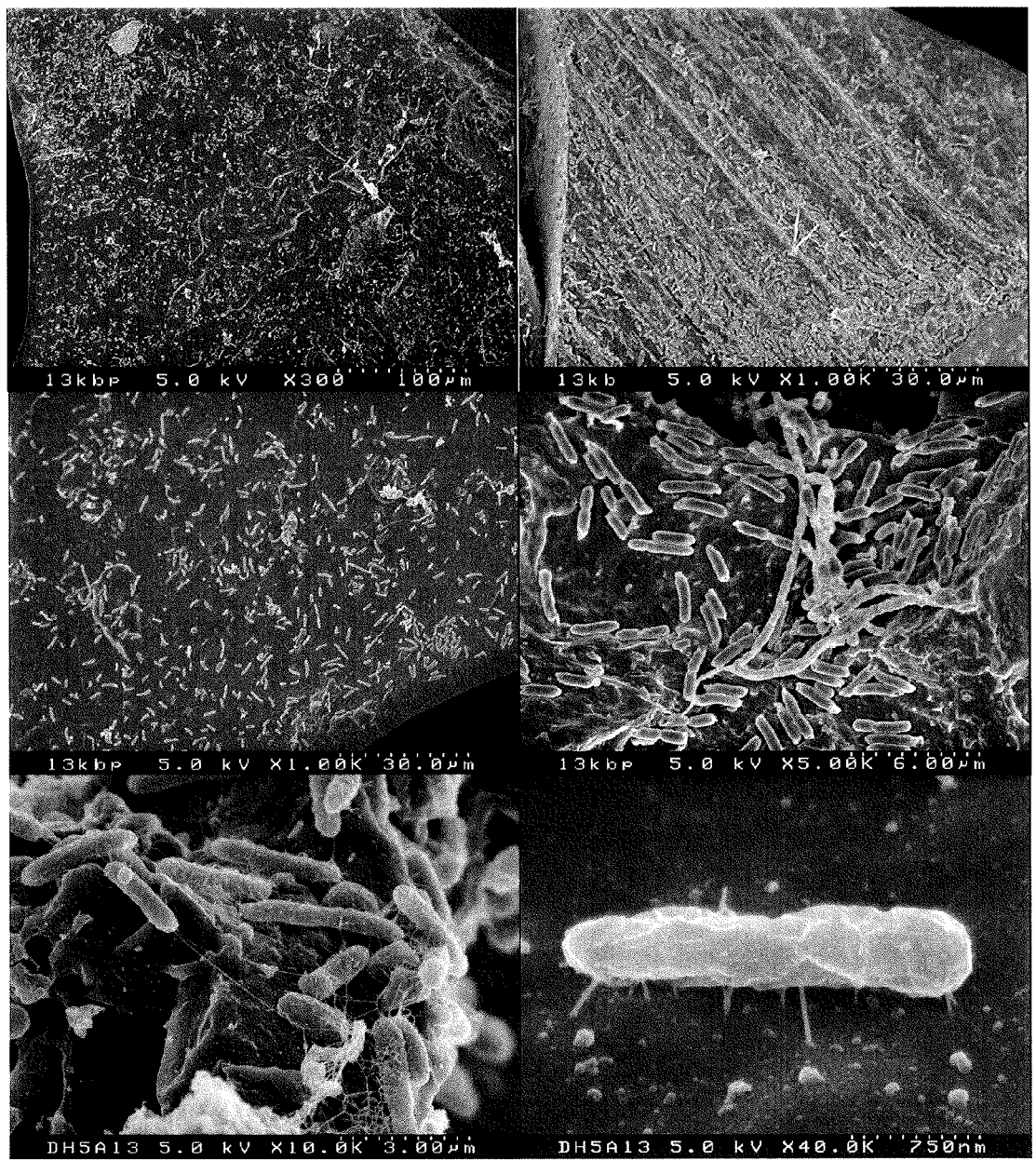
FIG. 8 shows an electron micrograph of DH5α::aadA-ompA that has adhered to a polyurethane surface.
Figure 9:
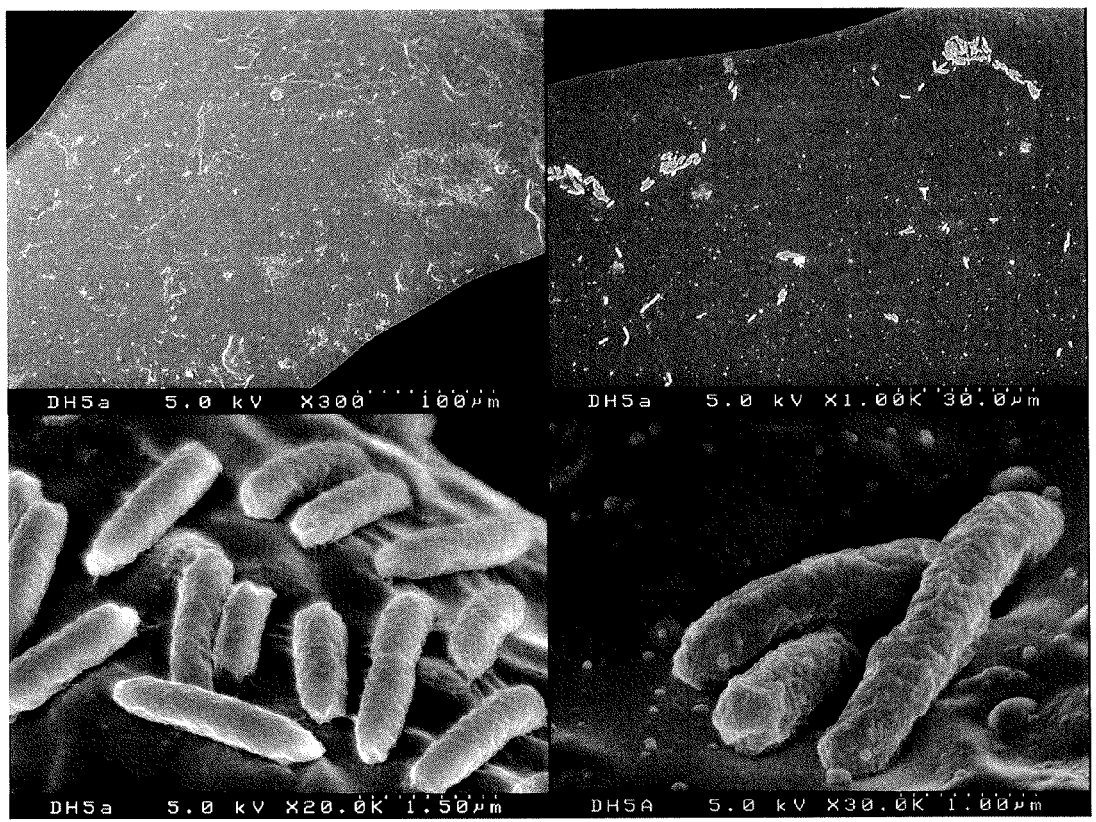
FIG. 9 shows an electron micrograph of DH5α (WT) that exists on a polyurethane surface.

In order to observe morphological changes resulting from gene introduction in greater detail, 3 types of strains (i.e., DH5α::aadA, DH5α::aadA-ompA, and DH5αWT strains) were subjected to morphological observation under a scanning electron microscope (FE-SEM) and under a transmission electron microscope (TEM). The results of observation via FE-SEM are shown in FIGS. 7 to 9.

In the DH5α::aadA strain, polyurethane carrier surfaces to which bacterial cells had adhered were clearly distinguishable from polyurethane carrier surfaces to which the cells had not adhered. The cells autoagglutinated and seemed to adhere to the surfaces in the aggregated forms. In the aggregates, large quantities of EPS-like structures were produced and bacterial cells were stacked up and had adhered to each other throughout multiple layers. In addition, relatively large quantities of DH5α::aadA cells elongated into long and thin shapes, which is consistent with the image, obtained as a result of optical microscopic observation. In the enlarged image, portions that look like joints were observed among the long and thin shapes, and the bacterial cells were linked each other at their poles. Further, structures that look like appendages were observed in the bacterial cells that had elongated into the long and thin shapes (FIG. 7).

In the DH5α::aadA-ompA strain, numerous bacterial cells appeared to have adhered to polyurethane carriers. It seems that each of the bacterial cells adheres to a carrier in a mariner such that a uniform monolayer film is formed on the carrier surface. In the DH5α::aadA-ompA strain, production of EPS-like structures was also observed. This is consistent with the results of optical microscopic observation. In the DH5α::aadA-ompA strain, many substances that look like appendages linking bacterial cells to the carrier were observed (FIG. 8).

Unlike the two recombinant strains, there were substantially no *E. coli* DH5αWT cells that had adhered to polyurethane carriers, and the cells appeared to have "ridden by accident" rather than "adhered" to the polyurethane carriers. Also, only a small quantity of the cells produced a structure such as an appendage (FIG. 9).

Thus, introduction of the aadA gene and the aadA-ompA operon of the *Acinetobacter* sp. Tol 5 strain into the *E. coli* DH5αstrain resulted in changes in the form of adhesion.

Further, differences were observed between adhesion forms of DH5α::aadA-ompA and DH5α::aadA. In the DH5α::aadA-ompA strain, while each bacterial cell independently adhered to a carrier and formed a uniform layer, a multilayer was not formed via agglutination of the cells. In contrast, in the DH5α::aadA strain, bacterial cells formed gigantic aggregates and adhered to the carrier in the form of a multilayer, but each cell did not independently adhere to the carrier.

2-3: Adhesion Test and Agglutination Test

In order to examine changes in adhesion resulting from introduction of the aadA gene and the aadA-ompA operon, an adhesion test via crystal violet staining (the CV adhesion test) was carried out. The adhesion test was evaluated in the following manner.

<Adhesion Test>

1. A bacterial liquid culture is centrifuged at 3,400 rpm and room temperature for 10 minutes.

2. A medium is removed via decantation, and an adequate amount of BS medium for the MATS test is added.

3. Ultrasonication is carried out with the use of UD-200 (TOMY) under the conditions of OUTPUT=5 and TIME=20 seconds to suspend bacterial cells, followed by adjustment of $OD_{660}$ to approximately 0.2.

4. The suspension is added to each well of a 48-well microplate (Iwaki) in amounts of 1 ml each, and incubated at 37° C. for 2 hours.

5. The suspension in the wells is completely pipetted out. In this case, care should be taken so as not to scrape the plate with the end of a chip.

6. Wells are washed with 1 ml of BS medium for the MATS test, and the plate is then air dried.

7. 1% Crystal violet is added to the wells, and incubated at room temperature for 15 minutes.

8. 1% Crystal violet is completely pipetted out, the wells are washed twice with 1 ml of BS medium for the MATS test, and the plate is then air dried.

9. 1 ml of BS medium for the MATS test is added, and ultrasonication is carried out under the conditions of OUTPUT=4 and TIME 20 seconds to disperse stained bacteria in BS medium.

10. $A_{590}$ is measured.

The results of the adhesion test of bacteria cultured in M9 medium are shown below.

| Samples | $A_{590}$ |
|---|---|
| 13 kb | 0.226 |
| 11 kb | 0.173 |
| WT | 0.081 |

*E. coli* into which the adhesion-associated gene had been introduced exhibited improved adhesiveness to a solid surface compared with a wild-type strain. The results demonstrate that introduction of the adhesion-associated gene confers the adhesive property to bacteria with low adhesiveness. In addition, the results demonstrate that the aadA gene and the aadA-ompA operon obtained herein are associated with the adhesion of microorganisms.

Figure 10:
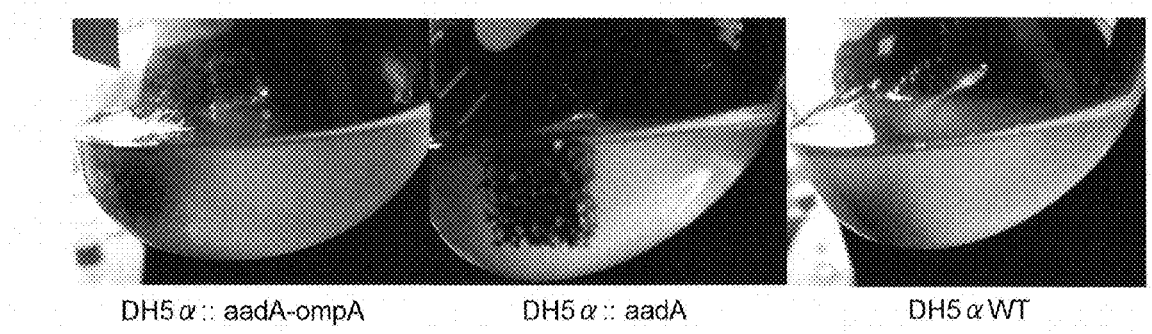
FIG. 10 shows photographs of liquid cultures of DH5α::aadA-ompA, DH5α::aadA, and DH5αWT.

Differences were observed among culture broth of the strains (FIG. 10). While the liquid culture of the wild-type strain was homogeneously clouded, the DH5α::aadA-ompA cells and the DH5α::aadA cells aggregated to the extent that such agglutination could be visually observed, and the culture solutions were clear.

Agglutination tests were performed in order to quantitate autoagglutination. The agglutinating property was evaluated in the following manner.

<Autoagglutination Test>

1. The bacterial culture broth was centrifuged and the culture supernatant was removed.

2. An inorganic salt medium was added to the bacterial pellet and cell suspension was obtained via ultrasonication.

3. The turbidity ($OD_{660}$) of the bacterial suspension was adjusted to a constant level with a medium. The $OD_{660}$ value at this time was defined as the initial $OD_{660}$ value.

4. The cell suspension in a glass centrifuge tube was allowed to stand at room temperature for sedimentation of the formed aggregates of cells, and changes over time in the $OD_{660}$ value of the supernatant were measured.

5. The percentage of autoagglutination (aggregation) was determined by the following equation.

$$\mathrm{Aggregation}(\%) = \frac{\text{initial } OD660 - OD660 \text{ after sampling}}{\text{initial } OD660} \times 100$$

Figure 11:
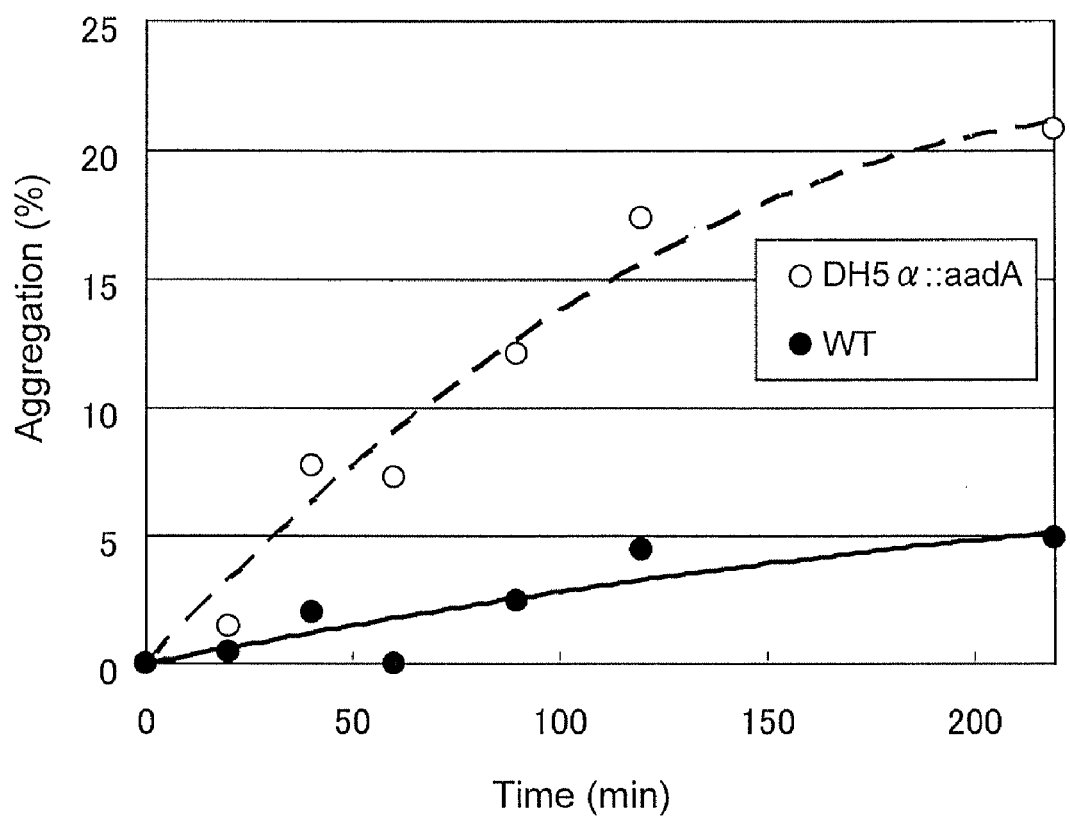
FIG. 11 shows the results of the autoagglutination tests of DH5α::aadA and DH5αWT.

The results are shown in FIG. 11.

As shown in the chart, autoagglutinating property of DH5α::aadA was improved compared with that of DH5αWT. The results are consistent with the clarity of the liquid culture and the results of FE-SEM observation. It was thus demonstrated that introduction of the aadA gene would also provide autoagglutinating property to bacterial cells.

All publications, patents, and patent applications cited herein are incorporated herein by reference in their entirety.

I claim:

1. A recombinant microorganism comprising
   (a) an isolated nucleic acid comprising the nucleotide sequence of SEQ ID NO: 1; or
   (b) an isolated nucleic acid having at least 98% homology to the nucleotide sequence of SEQ ID NO: 1, wherein the isolated nucleic acid encodes a protein that provides or enhances a nonspecific adhesive property, an autoagglutinating property, or both a nonspecific adhesive property and an autoagglutinating property in the microorganism; or
   (c) an isolated nucleic acid consisting of a part of the nucleotide sequence of SEQ ID NO: 1, wherein the nucleic acid sequence encodes a protein that provides or enhances a nonspecific adhesive property, an autoagglutinating property, or both a nonspecific adhesive property and an autoagglutinating property in the microorganism.

2. The recombinant microorganism of claim 1, wherein the microorganism is a bacterium of the genus *Escherichia*.

3. The recombinant microorganism of claim 2, wherein the microorganism is *Escherichia coli*.

4. A The recombinant microorganism of claim 1, further comprising a nucleic acid comprising the nucleotide sequence of SEQ ID NO:3 or a nucleic acid having at least 90% homology with the nucleotide sequence of SEQ ID NO:3, wherein the nucleic acid encodes an outer membrane protein and provides or enhances the nonspecific adhesive property, the autoagglutinating property or both the nonspecific adhesive property and the autoagglutinating property of the microorganism, when comprised in the microorganism with the nucleic acid of any one of nucleic acids (a) to (c) of claim 1.

5. The recombinant microorganism of claim 4 comprising a nucleic acid comprising the nucleotide sequence of SEQ ID NO:5 or a nucleic acid having at least 98% homology with the nucleotide sequence of SEQ ID NO:5, wherein the nucleic acid sequence encodes a protein that provides or enhances the nonspecific adhesive property, the autoagglutinating property or both the nonspecific adhesive property and the autoagglutinating property of the microorganism.

6. A method for production of a chemical product comprising culturing the microorganism of claim 1, wherein the microorganism synthesizes a chemical product.

7. The recombinant microorganism of claim 1, wherein the microorganism is genetically engineered to synthesize a chemical product.

8. A method for production of a chemical product comprising culturing the microorganism of claim 7, wherein the microorganism synthesizes a chemical product.

9. The recombinant microorganism of claim 4, wherein the microorganism is genetically engineered to synthesize a chemical product.

10. A method for production of a chemical product comprising culturing the microorganism of claim 9, wherein the microorganism synthesizes a chemical product.

11. The recombinant microorganism of claim 5, wherein the microorganism is genetically engineered to synthesize a chemical product.

12. A method for production of a chemical product comprising culturing the microorganism of claim 11, wherein the microorganism synthesizes a chemical product.

* * * * *

SEQUENCE LISTING

```
<160> NUMBER OF SEQ ID NOS: 29

<210> SEQ ID NO 1
<211> LENGTH: 10893
<212> TYPE: DNA
<213> ORGANISM: Acinetobacter sp. Tol5

<400> SEQUENCE: 1
atgaataaaa tctacaaagt gatttggaat gcgactttgt tggcatgggt tgcagtatct      60
gaattggcaa aagggaaaac caaatctacg acatcaaaat ccaaagctaa atcattatct     120
tcatctgtaa tagttggtgg gataatatta acaacacctt tatctttaat agcagctact     180
gttcaagttg gaggggaac taattctgga acaactgcta cagcttctac gaattgtgca      240
gacttatata attatcaaaa tcctgagaac tcaggctctg gagcggctgg gaattataat     300
gcaggaaatc caagtgtgtg ttcgatcgct ataggtgaaa acgcacaagg tggtacttct     360
ggaactggag ggtcgccagg gatagcgata ggtgaaaatt ctaaagctac gggtggttta     420
tctgttgcta taggcggata tgctcaagcg acaaatgttg gaagtattgc tttaggcaca     480
gcagctttat caagtggttt taacagttta gcaatatcca gacaagctgc tgcaacgaat     540
aactattcaa tagctatagg tacaacttca gtttcgaaag gagttggatc gattgctatg     600 ggcattcaa cgaatgcttc tggagatcaa tcgatagcaa ttggtagctc ggatgctgtt     660
aattcagcaa cagcaacaac aacatacgat ggtacaacaa atactcaagc atcaggtagt     720
aaatcgattg ctataggtgc aagcgcaaag gcatcaacca ataacagcat tgcactaggt     780
gcaggatcgg taacttctgc acaatctggt aattcttatc ttactggtgt aggtgcatca     840
gctacaaatg gtgttgtatc tgttggaact tcaactgcaa cacgtcgtat ccaaaatgta     900
gcagatggtt cagccgcttc agatgctgtg acagttgctc agttggataa agcttatgat     960
gatacaaatg gtcgtttagc tgctgcttta ggtacaggta gtggtgctgc ctataatgca    1020
gcaaacaata catataccgc tccaacgaat attgggggaa caggtaaaaa tacgattgat    1080
gatgcaatta aagcaactca acgaagtgta gtcgctggat caaatattgt cgttaccccg    1140
acgacagctt ctgatggttc aatatcgtat tcggttgcta caagcgcaac accgacgttt    1200
acaagtataa ctgtaaacaa tgcaccaacg gcaggtacag atgcgaccaa caagacttat    1260
gtagactcaa aagcagcagc atcgagaaca gaagtagcag ctggaagcaa tgtatctggt    1320
gtagtaaaaa cgacaggcgc aaacggtcaa gacgtttata cagtaaatgc caatggtacg    1380
actgcatcag caggttcttc agcagttacc gtaacaccag gcacgaaaga tgcaaataat    1440
```

```
gtcactgact ataaagtaga cttatcagcg actacaaaaa ccgatatcca aaaaggtgta   1500
gatgcaaaaa atgctgtaga taccgcaggt ctaaaattta aaggtgatac agcaaccaca   1560
agcaatacca agaaattagg tgacaccgtt tcgattacgg gtgatacgaa cattagtaca   1620
gttgcgacaa cagatggtgt acaggttaag ttaaatccaa acttggattt aggagcaact   1680
ggtagcgtta aaacgggtaa taccacgatt aacaatgcag gtgtaacagc tgatcaagtt   1740
acggttggtg gtgttgttat taacaacaca tcaggtatta atgctggtgg taaagcgatt   1800
actaatgtag cagcaccaac aaataacaca gatgctgcta acaagaagta tgtagatgat   1860
gcaggtacag cattaaccaa tttgggcttt ggattaaaag cacaagatgg tacgactgtg   1920
aacaagaaat taggtgaagc agttgatatt gttggttcaa acagcaacat cagtacaaaa   1980
gtaaatgcag gcaaagtaga agttgcacta tccaatacat tggacttagg tactacaggt   2040
agcgttacta cgggttcaac tgtaattaac aatactggtg ttacggcaac tcaggttacc   2100
gcaaacaaag tcacaataaa caatgcacca acagcaggta cagatgcgac caacaagact   2160
tatgtagact caaaagcagc agcatcaaga acagaagtcg cagctggaag caatgtatct   2220
ggtgtagtaa aaacgacagg cgcaaacggt caagatattt atgcagtaaa tgccaatggt   2280
acgactgcat cagcaggttc ttcagcagtt accgtaacac caggcacgaa agatgcaaat   2340
aatgtcactg actataaagt agacttgtca gcgactacaa aaaccgatat tcaaaaggt   2400 gtagatgcaa aaaatgctgt agatactgca ggtctaaaat ttaaaggtga tacagcaacc   2460
acaagcaata ccaagaaatt aggtgacacc gtttcgatta cgggtgatac gaacattagt   2520
acagttgcaa caactgatgg tgtacaggtt aagttaaatc caaacttaga tttaggagca   2580
actggtagcg ttaaaacggg taataccacg attaacaatg caggtgtaac agctgaccaa   2640
gttacggttg gtggtgttgt tattaacaac acatcaggta ttaatgctgg tggtaaagcg   2700
attaccaatg tagcagcacc aacaaataac acagatgctg ctaacaagaa gtatgtagat   2760
gacgcaggta cagcattaac caatttgggc tttggattaa aagcgcaaga tggtacgact   2820
gtgaacaaga aattaggtga agcagttgat attgttggtt caaacagcaa catcagtaca   2880
aaagtaaatg caggcaaagt agaagttgca ctatccaata cattggactt aggtactaca   2940
ggtagcgtta ctacgggttc aactgtaatt aacaatgctg gtgttacggc aactcaagtt   3000
accgcaaaca agtcacagt taataatgca ccaacagcag gtacagatgc gaccaataaa   3060
acttatgtag actcaaaagc agcggcatca agaacagaag tcgcagctgg aagcaatgta   3120
tctggcgtag taaaaacgac aggtgcaaac ggtcaagacg tttatacagt aaatgccaat   3180
ggtacgactg catcagcagg ttcttcagca gttaccgtaa caccaggcac gaaagatgca   3240
aataatgtca ctgactataa agtagacttg tcagcgacta caaaaaccga tattcaaaaa   3300
ggtgtagatg caaaaaatgc tgtagatacc gcaggtctaa aatttaaagg tgatacagca   3360
accacaagca ataccaagaa attaggtgac accgtttcga ttacgggtga tacgaacatt   3420
agtacagttg cgacaactga tgtgtacag gttaagctaa atccaaactt ggatttagga   3480
gcaactggta gcgttaaaac gggtaatacc acgattaaca atgcaggtgt aacagctgat   3540
caagttacag ttggtggtgt tgttattaac aacacatcag gtattaatgc tggtggtaaa   3600
gcgattacca atgtagcagc accaacaaat aacacagatg ctgctaacaa gaagtatgta   3660
gatgatgcag gtacagcatt aaccaatttg gctttggat taaaagcgca agatggtacg   3720
actgtgaaca agaaattagg cgaagcagtt gaagttgttg gtgcggacag taacatcacc   3780
acgaaagttg caggcggtca ggttgcaatt gagttaaata aaaacctcaa caacttaact   3840
```

-continued

```
ggcattaccg tgaacgatgg aaccaatggc accaatggtt caactgtgat tggtaaagat      3900
ggtatttcgg ttaaagatgg ttcaggcaat accattgcag gtgtagataa cacagcgttg      3960
acagttaaag atggcagtgg caacacagaa accagcatta accaagcgat caacacgtta      4020
aatgcagcgc aaggtgaaac tgataagttt gcagtgaagt acgacaaaaa tgctgatggc      4080
agtgtgaact acaacaacat cacattggca ggtacgactg caagcagtac acaagatgca      4140
actacaggca agatcaccac aacaggtgga acaagcttga acaatgttgc aagtgcgggt      4200
gactacaaag atgttgccaa tgcaagcaaa ggtgtaaacg caggtgactt aaacaatgca      4260
gttgttgatg caaccaatgc agcaaccagc aaaggctttg cattacaagc agcagatggc      4320
gctaaagttc agaagaacct aggcgaagca gttgaagttg tcggtgccga cagcaacatc      4380
accacaaaag ttgcaggcgg tcaggttgca attgagttaa ataaaaacct caacaactta      4440
actggcatta ccgtgaacga tggaaccaat ggcaccaatg gttcaactgt gattggtaaa      4500
gatggtattt cagttaaaga cggttcaggc aataccattc aggtgtaga taacacagcg      4560
ttgacagtta agatggcagt ggcaacacag aaaccagca ttaaccaagc gatcaacacg      4620
ttaaatgcag cgcaaggtga aactgataag tttgcagtga agtacgacaa aaatacggat      4680
ggtagtacca actacaacag tattactgca ggcaatggta acggtactgc agcaacgatc      4740
gaactgaca cagcaggtaa tagtgttgtg accgtggcg gaactaaaat tagtaatgtt      4800
gcgaatggtg tcaatgcaag tgatgcagta acaaaggtc aattggatag cttaagtaca      4860
ggtcttacca atacaggctt tggtttaaaa gcagcagatg gcaacaccgt taacaaaaaa      4920
ttaggcgaag cagtagacgt tgtcggtgct gacagcaaca tcaccacgaa agttgcaggc      4980
ggtcaggttg cgattgagtt aaataaaaac ctcaacaact taactggcat taccgtgaac      5040
gatggaacca atggcaccaa tggttcaact gtgattggta agatggtat ttcgattaaa      5100
gatggttcag gcaataccat tgcaggtgta gataacacag cgttgacagt taagatggc      5160
agtggcaaca cagaaaccag cattaaccaa gcgatcaaca cgttaaatgc agcgcaaggt      5220
gaaactgaca gtttgcagt gaagtacgac aagaatgctg atggcagtgc aaactacaac      5280
aacatcacat tggcaggtac gactgcaagt agcacgcaag atgcaacaac aggcaagatc      5340
accacaacag gtgaacaag cttgaacaac gttgcaagtg caggtgacta caaagatgtt      5400
gccaatgcaa gcaaaggtgt aaacgcaggt gacttgaaca atgcagttgt tgatgcaacc      5460
aatgcagcaa ccagcaaagg ctttgcatta caagcagcag atggcgctaa agttcagaag      5520
aacctaggcg aagcagttga agttgtcggt gcggacagca acatcaccac aaaagtagtg      5580
ggtggacaag ttgcgattga gttaaataaa aacctcaaca acttaactgg cattaccgtg      5640
aacgatggaa ccaatggcac aaatggttca actgtgattg gtaaagatgg tatttcggtt      5700
aaagatggtt caggtaatac cattgcaggt gtagataaca cagcgttgac agttaaagat      5760
ggcagtggca acacagaaac cagcattaac caagcgatca cacgttaaa tgcagcgcaa      5820
ggtgaaactg ataagtttgc agtgaagtac gacaaaaatg ctgatggcag tgtgaactac      5880
aacaacatca cattggcagg tacgactgca agcagtacac aagatgcaac acaggcaag      5940
atcaccacaa caggtggaac aagcttgaac aatgttgcaa gtgcgggtga ctacaaagat      6000
gttgccaatg caagcaaagg tgtaaacgca ggtgacttaa acaatgcagt tgttgatgca      6060
accaatgcag caaccagcaa aggctttgca ttacaagcag cagatggcgc taaagttcag      6120
aagaacctag gcgaagcagt tgaagttgtc ggtgccgaca gcaacatcac cacaaaagtt      6180
gcaggcggtc aggttgcaat tgagttaaat aaaaacctca caacttaac tggcattacc      6240
```

```
gtgaacgatg gaaccaatgg caccaatggt tcaactgtga ttggtaaaga tggtatttca   6300
gttaaagacg gttcaggcaa taccattgca ggtgtagata acacagcgtt gacagttaaa   6360
gatggcagtg gcaacacaga aaccagcatt aaccaagcga tcaacacgtt aaatgcagcg   6420
caaggtgaaa ctgataagtt tgcagtgaag tacgacaaaa atgctgatgg cagtgtgaac   6480
tacaacaaca tcacattggc aggtacgact gcaagcagta cacaagatgc aactacaggc   6540
aagatcacca acacaggtgg tacaagcttg aacaatgttg caagtgcggg tgactacaaa   6600
gatgttgcca atgcaagcaa aggtgtaaac gcaggtgact tgaacaatgc agttgttgat   6660
gcaaccaatg cagcgaccag caaaggctt t gcattacaag cagcagatgg cgctaaagtt   6720
cagaagaacc taggcgaagc agttgaagtt gttggtgcgg acagtaacat caccacgaaa   6780
gttgcaggcg gtcaggttgc aattgagtta aataaaaacc tcaacaactt aactggcatt   6840
accgtgaacg atggaaccaa tggcaccaat ggttcaactg tgattggtaa agatggtatt   6900
tcggttaaag atggttcagg caataccatt gcaggtgtag ataacacagc gttgacagtt   6960
aaagatggca gtggcaacac agaaaccagc attaaccaag cgatcaacac gttaaatgca   7020
gcgcaaggtg aaactgataa gtttgcagtg aagtacgaca aaaatgctga tggcagtgca   7080
aactataaca atgtcacttt agctggtaca aatggcacaa taatcagcaa tgttaaagcg   7140
ggtgctgtga cctcaacatc tactgatgcg atcaatggta gccaattata tggtgttgca   7200
aacagcgtga agaatgcaat tggtggttca accacaattg atgcaacgac tggtgcaatc   7260
acgacgacca atattggtgg tacaggttca aatacgattg atggtgcaat cagcagtatt   7320
aaagattcag cgactaaagc gaaaaccacg gtaagtgctg gggataatgt tgtcgttaca   7380
tcgggtacca atgcagatgg ctcaacaaac tatgaagttg cgacagcgaa agacgttaac   7440
tttgacaaag tgactgtagg tagtgttgtt gtagataaat caagcaatac aatcaaagga   7500
ttaagtaata ccacttggaa cggaacagca gtatcaggtc aagcggcgac agaagaccag   7560
ttaaaaacgg tcagcgatgc gcaaggtgaa actgataagt ttgcagtgaa gtacgacaaa   7620
aatgctgatg gcagtgcgaa ctacaacagt attactgcag gcaatggtaa cggtactgca   7680
gcaacgatcg gaactgacac agcaggtaat agtgttgtga ccagtggcgg aactaaaatt   7740
agtaatgttg cgaatggtgt caatgcaagt gatgcagtaa acaaaggtca attggatagc   7800
ttaagtacag gtcttaccaa tacaggcttt ggtttaaaag cagcagatgg caacaccgtt   7860
aacaaaaaat taggcgaagc agtagacgtt gtcggtgctg acagcaacat caccacgaaa   7920
gttgcaggcg gtcaggttgc gattgagtta aataaaaacc tcaacaactt aactggcatt   7980
accgtgaacg atggaaccaa tggcaccaat ggttcaactg tgattggtaa agatggtatt   8040
tcgattaaag atggttcagg caataccatt gcaggtgtag ataacacagc gttgacggtt   8100
aaagatagca gtggcaacac agaaaccagc attaaccaag cgatcaacac gttaaatgca   8160
gcgcaaggtg aaactgataa gtttgcagtg aagtacgata gaatgctga tggcagtgtg   8220 aactataaca atgtcacttt agcaggtaca aatggcacaa taatcagaaa tgttaaagcg   8280
ggtgctgtga cctcaacatc tactgatgcg atcaatggta gccaattata cgatattgca   8340
aacagcgtga agaatgcaat tggtggttca accacaagag atgtaacgac tggtgcaatc   8400
acaacgacca atattggtgg tacaggttca aacacgattg atggtgcaat cagcagtatt   8460
aaagattcag cgactaaagc gaaaaccacg ataagtgctg gggataatgt tgtcgttaca   8520
tcgggtacca atgcagatgg ctcaacaaac tatgaagttg cgacagcgaa agacgttaac   8580
tttgacaaag taactgtagg taatgttgtt gttgataagg caaatgacac gatccaaggt   8640
```

```
ttgagcaata aagatctaaa ttcaactgat tttgcgacca aaggtagagc tgcgactgaa    8700
gaacagttaa aagcagtgat taccagtaat atcacggaag ttgtggatgg taatggcaac    8760
aaggtgaata ttattgacca agttgtaaat accaaacctg acaataagaa ccaagattca    8820 tgttcttaa cgtatgacaa acaaggtcaa gaaaccacag atcgcctaac gattggtcaa     8880
acggtacaga agatgaatac tgatggtatt aaattcttcc ataccaatgc cgatacatca    8940
aaaggtgatt tgggtacaac aaatgactca agtgcaggtg gtttaaactc tacagcaatt    9000
ggtgtaaatg cgattgttgc gaatggtgca gatagttcag ttgctttagg tcataacacc    9060
aaagtcaatg gtaaacaatc aattgcaatt ggttctggtg cagaagcttt aggcaatcaa    9120
tcgatcagta ttggtacagg caataaagtc actggtgatc attcgggtgc gattggtgat    9180
ccaactattg taaatggtgc aaacagctac tctgtgggta ataacaacca agtacttaca    9240
gatgacactt tcgtacttgg aaacaatgtc accaaaacta ttgctggttc agtagtattg    9300
ggtaacggtt cagctgcaac gacaggtgct ggtgaggcag gctatgcctt atctgtagca    9360
acaaatgcag ataaagccgc gatcactaaa actacgtcaa gcactggtgc tgttgcagtt    9420
ggtgatgcgt cgagcggtat ttatcgtcaa attaccggtg ttgctgcggg tagcgtagat    9480
tcagatgctg tgaacgttgc acagttaaaa gcggtgggta accaagttgt aacgactcaa    9540
actacattgg tgaacagttt gggtggtaac gctaaagtaa atgcagacgg tacgattaca    9600
ggaccaactt ataatgttgc tcaaggtaat cagaccaatg ttggtgatgc attaactgcg    9660
cttgataacg caattaatac tgcggcaaca acatctaaat cgactgtttc taatggtcag    9720
aatattgttg tcagcaagag caaaaatgca gatggttcag acaactatga agtatcaaca    9780
gcaaaagact tgacagttga ttctgtcaaa gcgggtgata cggttctgaa taatgcaggt    9840
attacaattg gcaataacgc agttgtattg aacaacactg gattaaccat tagtggtgga    9900
ccaagtgtta ccttggcagg catcgatgca ggcaataaaa ccattcaaaa tgttgcgaat    9960
gcagtaaatg caacagatgc agtcaacaaa gggcaattgg acagcgcaat taacaatgtg   10020
aataacaatg taaatgagct tgccaacaac gctgttaaat atgacgatgc atcaaaagat   10080
aagatcacac ttggtggtgg ggcaactggt acaacaatca ccaatgtgaa agatggtact   10140
gttgcgcaag ttctaaaga tgctgtgaat ggcggtcaat tgtggaatgt tcaacaacaa    10200
gttgatcaga acacaactga tattagcaat atcaaaaatg atattaacaa cggtactgtt   10260
ggtttggttc aacaagcagg taaagatgca ccagtgacgg ttgcaaaaga tactggcggt   10320
acaacggtga atgtcgctgg aacagatggc aaccgagtag tgacaggtgt taaggaaggt   10380
gcagtgaatg caacatctaa agatgctgtc aatggtagtc aattgaatac aaccaaccaa   10440
gcggtagtca attatcttgg tggtggggca ggttatgaca acattacagg tagcttcaca   10500
gcgccaagtt atacggtagg tgactcgaaa tacaacaatg ttggtggcgc aattgatgca   10560
ttgaatcaag cagatcaagc attgaatagc aaaattgaca atgtcagtaa caagttggat   10620
aacgcattcc gtattaccaa caaccgtatt gatgatgtag agaaaaaagc caatgctggt   10680
attgccgctg cgatggctct ggaatcagca ccatatgtcc caggtaaata tacctatgca   10740
gcaggcgcag cttaccacgg tggtgaaaat gcggtaggtg tgactttacg taaaactgca   10800
gacaatggtc gttggtcgat tacaggcggt gtagctgcag cgtctcaagg cgatgcaagt   10860
gttcgtatcg gtatcagcgg tgtgattgac taa                                10893
```

<210> SEQ ID NO 2
<211> LENGTH: 3630

<212> TYPE: PRT
<213> ORGANISM: Acinetobacter sp. Tol5

<400> SEQUENCE: 2

```
Met Asn Lys Ile Tyr Lys Val Ile Trp Asn Ala Thr Leu Leu Ala Trp
1               5                   10                  15

Val Ala Val Ser Glu Leu Ala Lys Gly Lys Thr Lys Ser Thr Thr Ser
            20                  25                  30

Lys Ser Lys Ala Lys Ser Leu Ser Ser Val Ile Val Gly Gly Ile
        35                  40                  45

Ile Leu Thr Thr Pro Leu Ser Leu Ile Ala Ala Thr Val Gln Val Gly
    50                  55                  60

Gly Gly Thr Asn Ser Gly Thr Thr Ala Thr Ala Ser Thr Asn Cys Ala
65                  70                  75                  80

Asp Leu Tyr Asn Tyr Gln Asn Pro Glu Asn Ser Gly Ser Gly Ala Ala
                85                  90                  95

Gly Asn Tyr Asn Ala Gly Asn Pro Ser Val Cys Ser Ile Ala Ile Gly
            100                 105                 110

Glu Asn Ala Gln Gly Gly Thr Ser Gly Thr Gly Gly Ser Pro Gly Ile
        115                 120                 125

Ala Ile Gly Gly Asn Ser Lys Ala Thr Gly Gly Leu Ser Val Ala Ile
    130                 135                 140

Gly Gly Tyr Ala Gln Ala Thr Asn Val Gly Ser Ile Ala Leu Gly Thr
145                 150                 155                 160

Ala Ala Leu Ser Ser Gly Phe Asn Ser Leu Ala Ile Ser Arg Gln Ala
                165                 170                 175

Ala Ala Thr Asn Asn Tyr Ser Ile Ala Ile Gly Thr Thr Ser Val Ser
            180                 185                 190

Lys Gly Val Gly Ser Ile Ala Met Gly His Ser Thr Asn Ala Ser Gly
        195                 200                 205

Asp Gln Ser Ile Ala Ile Gly Ser Ser Asp Ala Val Asn Ser Ala Thr
    210                 215                 220

Ala Thr Thr Thr Tyr Asp Gly Thr Thr Asn Thr Gln Ala Ser Gly Ser
225                 230                 235                 240

Lys Ser Ile Ala Ile Gly Ala Ser Ala Lys Ala Ser Thr Asn Asn Ser
                245                 250                 255

Ile Ala Leu Gly Ala Gly Ser Val Thr Ser Ala Gln Ser Gly Asn Ser
            260                 265                 270

Tyr Leu Thr Gly Val Gly Ala Ser Ala Thr Asn Gly Val Val Ser Val
        275                 280                 285

Gly Thr Ser Thr Ala Thr Arg Arg Ile Gln Asn Val Ala Asp Gly Ser
    290                 295                 300

Ala Ala Ser Asp Ala Val Thr Val Ala Gln Leu Asp Lys Ala Tyr Asp
305                 310                 315                 320

Asp Thr Asn Gly Arg Leu Ala Ala Leu Gly Thr Gly Ser Gly Ala
                325                 330                 335

Ala Tyr Asn Ala Ala Asn Asn Thr Tyr Thr Ala Pro Thr Asn Ile Gly
            340                 345                 350

Gly Thr Gly Lys Asn Thr Ile Asp Asp Ala Ile Lys Ala Thr Gln Arg
        355                 360                 365

Ser Val Val Ala Gly Ser Asn Ile Val Val Thr Pro Thr Thr Ala Ser
    370                 375                 380

Asp Gly Ser Ile Ser Tyr Ser Val Ala Thr Ser Ala Thr Pro Thr Phe
385                 390                 395                 400
```

-continued

```
Thr Ser Ile Thr Val Asn Asn Ala Pro Thr Ala Gly Thr Asp Ala Thr
            405                 410                 415

Asn Lys Thr Tyr Val Asp Ser Lys Ala Ala Ser Arg Thr Glu Val
        420                 425                 430

Ala Ala Gly Ser Asn Val Ser Gly Val Val Lys Thr Thr Gly Ala Asn
            435                 440                 445

Gly Gln Asp Val Tyr Thr Val Asn Ala Asn Gly Thr Thr Ala Ser Ala
        450                 455                 460

Gly Ser Ser Ala Val Thr Val Thr Pro Gly Thr Lys Asp Ala Asn Asn
465                 470                 475                 480

Val Thr Asp Tyr Lys Val Asp Leu Ser Ala Thr Thr Lys Thr Asp Ile
                485                 490                 495

Gln Lys Gly Val Asp Ala Lys Asn Ala Val Asp Thr Ala Gly Leu Lys
            500                 505                 510

Phe Lys Gly Asp Thr Ala Thr Thr Ser Asn Thr Lys Lys Leu Gly Asp
        515                 520                 525

Thr Val Ser Ile Thr Gly Asp Thr Asn Ile Ser Thr Val Ala Thr Thr
    530                 535                 540

Asp Gly Val Gln Val Lys Leu Asn Pro Asn Leu Asp Leu Gly Ala Thr
545                 550                 555                 560

Gly Ser Val Lys Thr Gly Asn Thr Thr Ile Asn Asn Ala Gly Val Thr
                565                 570                 575

Ala Asp Gln Val Thr Val Gly Gly Val Val Ile Asn Asn Thr Ser Gly
            580                 585                 590

Ile Asn Ala Gly Gly Lys Ala Ile Thr Asn Val Ala Ala Pro Thr Asn
        595                 600                 605

Asn Thr Asp Ala Ala Asn Lys Lys Tyr Val Asp Ala Gly Thr Ala
    610                 615                 620

Leu Thr Asn Leu Gly Phe Gly Leu Lys Ala Gln Asp Gly Thr Thr Val
625                 630                 635                 640

Asn Lys Lys Leu Gly Glu Ala Val Asp Ile Val Gly Ser Asn Ser Asn
                645                 650                 655

Ile Ser Thr Lys Val Asn Ala Gly Lys Val Glu Val Ala Leu Ser Asn
            660                 665                 670

Thr Leu Asp Leu Gly Thr Thr Gly Ser Val Thr Thr Gly Ser Thr Val
        675                 680                 685

Ile Asn Asn Thr Gly Val Thr Ala Thr Gln Val Thr Ala Asn Lys Val
    690                 695                 700

Thr Ile Asn Asn Ala Pro Thr Ala Gly Thr Asp Ala Thr Asn Lys Thr
705                 710                 715                 720

Tyr Val Asp Ser Lys Ala Ala Ala Ser Arg Thr Glu Val Ala Ala Gly
                725                 730                 735

Ser Asn Val Ser Gly Val Val Lys Thr Thr Gly Ala Asn Gly Gln Asp
            740                 745                 750

Ile Tyr Ala Val Asn Ala Asn Gly Thr Thr Ala Ser Ala Gly Ser Ser
        755                 760                 765

Ala Val Thr Val Thr Pro Gly Thr Lys Asp Ala Asn Asn Val Thr Asp
    770                 775                 780

Tyr Lys Val Asp Leu Ser Ala Thr Thr Lys Thr Asp Ile Gln Lys Gly
785                 790                 795                 800

Val Asp Ala Lys Asn Ala Val Asp Thr Ala Gly Leu Lys Phe Lys Gly
                805                 810                 815

Asp Thr Ala Thr Thr Ser Asn Thr Lys Lys Leu Gly Asp Thr Val Ser
            820                 825                 830
```

```
Ile Thr Gly Asp Thr Asn Ile Ser Thr Val Ala Thr Asp Gly Val
            835                 840                 845

Gln Val Lys Leu Asn Pro Asn Leu Asp Leu Gly Ala Thr Gly Ser Val
            850                 855                 860

Lys Thr Gly Asn Thr Thr Ile Asn Asn Ala Gly Val Thr Ala Asp Gln
865                 870                 875                 880

Val Thr Val Gly Gly Val Val Ile Asn Thr Ser Gly Ile Asn Ala
                885                 890                 895

Gly Gly Lys Ala Ile Thr Asn Val Ala Ala Pro Thr Asn Asn Thr Asp
            900                 905                 910

Ala Ala Asn Lys Lys Tyr Val Asp Asp Ala Gly Thr Ala Leu Thr Asn
            915                 920                 925

Leu Gly Phe Gly Leu Lys Ala Gln Asp Gly Thr Thr Val Asn Lys Lys
            930                 935                 940

Leu Gly Glu Ala Val Asp Ile Val Gly Ser Asn Ser Asn Ile Ser Thr
945                 950                 955                 960

Lys Val Asn Ala Gly Lys Val Glu Val Ala Leu Ser Asn Thr Leu Asp
            965                 970                 975

Leu Gly Thr Thr Gly Ser Val Thr Thr Gly Ser Thr Val Ile Asn Asn
            980                 985                 990

Ala Gly Val Thr Ala Thr Gln Val Thr Ala Asn Lys Val Thr Val Asn
            995                1000                1005

Asn Ala Pro Thr Ala Gly Thr Asp Ala Thr Asn Lys Thr Tyr Val
           1010                1015                1020

Asp Ser Lys Ala Ala Ala Ser Arg Thr Glu Val Ala Ala Gly Ser
           1025                1030                1035

Asn Val Ser Gly Val Val Lys Thr Thr Gly Ala Asn Gly Gln Asp
           1040                1045                1050

Val Tyr Thr Val Asn Ala Asn Gly Thr Thr Ala Ser Ala Gly Ser
           1055                1060                1065

Ser Ala Val Thr Val Thr Pro Gly Thr Lys Asp Ala Asn Asn Val
           1070                1075                1080

Thr Asp Tyr Lys Val Asp Leu Ser Ala Thr Thr Lys Thr Asp Ile
           1085                1090                1095

Gln Lys Gly Val Asp Ala Lys Asn Ala Val Asp Thr Ala Gly Leu
           1100                1105                1110

Lys Phe Lys Gly Asp Thr Ala Thr Thr Ser Asn Thr Lys Lys Leu
           1115                1120                1125

Gly Asp Thr Val Ser Ile Thr Gly Asp Thr Asn Ile Ser Thr Val
           1130                1135                1140

Ala Thr Thr Asp Gly Val Gln Val Lys Leu Asn Pro Asn Leu Asp
           1145                1150                1155

Leu Gly Ala Thr Gly Ser Val Lys Thr Gly Asn Thr Thr Ile Asn
           1160                1165                1170

Asn Ala Gly Val Thr Ala Asp Gln Val Thr Val Gly Gly Val Val
           1175                1180                1185

Ile Asn Asn Thr Ser Gly Ile Asn Ala Gly Gly Lys Ala Ile Thr
           1190                1195                1200

Asn Val Ala Ala Pro Thr Asn Asn Thr Asp Ala Ala Asn Lys Lys
           1205                1210                1215

Tyr Val Asp Asp Ala Gly Thr Ala Leu Thr Asn Leu Gly Phe Gly
           1220                1225                1230

Leu Lys Ala Gln Asp Gly Thr Thr Val Asn Lys Lys Leu Gly Glu
```

```
              1235                1240                1245

Ala Val Glu Val Val Gly Ala Asp Ser Asn Ile Thr Thr Lys Val
1250                1255                1260

Ala Gly Gly Gln Val Ala Ile Glu Leu Asn Lys Asn Leu Asn Asn
1265                1270                1275

Leu Thr Gly Ile Thr Val Asn Asp Gly Thr Asn Gly Thr Asn Gly
1280                1285                1290

Ser Thr Val Ile Gly Lys Asp Gly Ile Ser Val Lys Asp Gly Ser
1295                1300                1305

Gly Asn Thr Ile Ala Gly Val Asp Asn Thr Ala Leu Thr Val Lys
1310                1315                1320

Asp Gly Ser Gly Asn Thr Glu Thr Ser Ile Asn Gln Ala Ile Asn
1325                1330                1335

Thr Leu Asn Ala Ala Gln Gly Glu Thr Asp Lys Phe Ala Val Lys
1340                1345                1350

Tyr Asp Lys Asn Ala Asp Gly Ser Val Asn Tyr Asn Asn Ile Thr
1355                1360                1365

Leu Ala Gly Thr Thr Ala Ser Ser Thr Gln Asp Ala Thr Thr Gly
1370                1375                1380

Lys Ile Thr Thr Thr Gly Gly Thr Ser Leu Asn Asn Val Ala Ser
1385                1390                1395

Ala Gly Asp Tyr Lys Asp Val Ala Asn Ala Ser Lys Gly Val Asn
1400                1405                1410

Ala Gly Asp Leu Asn Asn Ala Val Val Asp Ala Thr Asn Ala Ala
1415                1420                1425

Thr Ser Lys Gly Phe Ala Leu Gln Ala Ala Asp Gly Ala Lys Val
1430                1435                1440

Gln Lys Asn Leu Gly Glu Ala Val Glu Val Val Gly Ala Asp Ser
1445                1450                1455

Asn Ile Thr Thr Lys Val Ala Gly Gly Gln Val Ala Ile Glu Leu
1460                1465                1470

Asn Lys Asn Leu Asn Asn Leu Thr Gly Ile Thr Val Asn Asp Gly
1475                1480                1485

Thr Asn Gly Thr Asn Gly Ser Thr Val Ile Gly Lys Asp Gly Ile
1490                1495                1500

Ser Val Lys Asp Gly Ser Gly Asn Thr Ile Ala Gly Val Asp Asn
1505                1510                1515

Thr Ala Leu Thr Val Lys Asp Gly Ser Gly Asn Thr Glu Thr Ser
1520                1525                1530

Ile Asn Gln Ala Ile Asn Thr Leu Asn Ala Ala Gln Gly Glu Thr
1535                1540                1545

Asp Lys Phe Ala Val Lys Tyr Asp Lys Asn Thr Asp Gly Ser Thr
1550                1555                1560

Asn Tyr Asn Ser Ile Thr Ala Gly Asn Gly Asn Gly Thr Ala Ala
1565                1570                1575

Thr Ile Gly Thr Asp Thr Ala Gly Asn Ser Val Val Thr Ser Gly
1580                1585                1590

Gly Thr Lys Ile Ser Asn Val Ala Asn Gly Val Asn Ala Ser Asp
1595                1600                1605

Ala Val Asn Lys Gly Gln Leu Asp Ser Leu Ser Thr Gly Leu Thr
1610                1615                1620

Asn Thr Gly Phe Gly Leu Lys Ala Ala Asp Gly Asn Thr Val Asn
1625                1630                1635
```

-continued

Lys Lys Leu Gly Glu Ala Val Asp Val Val Gly Ala Asp Ser Asn
1640              1645              1650

Ile Thr Thr Lys Val Ala Gly Gly Gln Val Ala Ile Glu Leu Asn
1655              1660              1665

Lys Asn Leu Asn Asn Leu Thr Gly Ile Thr Val Asn Asp Gly Thr
1670              1675              1680

Asn Gly Thr Asn Gly Ser Thr Val Ile Gly Lys Asp Gly Ile Ser
1685              1690              1695

Ile Lys Asp Gly Ser Gly Asn Thr Ile Ala Gly Val Asp Asn Thr
1700              1705              1710

Ala Leu Thr Val Lys Asp Gly Ser Gly Asn Thr Glu Thr Ser Ile
1715              1720              1725

Asn Gln Ala Ile Asn Thr Leu Asn Ala Ala Gln Gly Glu Thr Asp
1730              1735              1740

Lys Phe Ala Val Lys Tyr Asp Lys Asn Ala Asp Gly Ser Ala Asn
1745              1750              1755

Tyr Asn Asn Ile Thr Leu Ala Gly Thr Thr Ala Ser Ser Thr Gln
1760              1765              1770

Asp Ala Thr Thr Gly Lys Ile Thr Thr Thr Gly Gly Thr Ser Leu
1775              1780              1785

Asn Asn Val Ala Ser Ala Gly Asp Tyr Lys Asp Val Ala Asn Ala
1790              1795              1800

Ser Lys Gly Val Asn Ala Gly Asp Leu Asn Asn Ala Val Val Asp
1805              1810              1815

Ala Thr Asn Ala Ala Thr Ser Lys Gly Phe Ala Leu Gln Ala Ala
1820              1825              1830

Asp Gly Ala Lys Val Gln Lys Asn Leu Gly Glu Ala Val Glu Val
1835              1840              1845

Val Gly Ala Asp Ser Asn Ile Thr Thr Lys Val Val Gly Gly Gln
1850              1855              1860

Val Ala Ile Glu Leu Asn Lys Asn Leu Asn Asn Leu Thr Gly Ile
1865              1870              1875

Thr Val Asn Asp Gly Thr Asn Gly Thr Asn Gly Ser Thr Val Ile
1880              1885              1890

Gly Lys Asp Gly Ile Ser Val Lys Asp Gly Ser Gly Asn Thr Ile
1895              1900              1905

Ala Gly Val Asp Asn Thr Ala Leu Thr Val Lys Asp Gly Ser Gly
1910              1915              1920

Asn Thr Glu Thr Ser Ile Asn Gln Ala Ile Asn Thr Leu Asn Ala
1925              1930              1935

Ala Gln Gly Glu Thr Asp Lys Phe Ala Val Lys Tyr Asp Lys Asn
1940              1945              1950

Ala Asp Gly Ser Val Asn Tyr Asn Asn Ile Thr Leu Ala Gly Thr
1955              1960              1965

Thr Ala Ser Ser Thr Gln Asp Ala Thr Thr Gly Lys Ile Thr Thr
1970              1975              1980

Thr Gly Gly Thr Ser Leu Asn Asn Val Ala Ser Ala Gly Asp Tyr
1985              1990              1995

Lys Asp Val Ala Asn Ala Ser Lys Gly Val Asn Ala Gly Asp Leu
2000              2005              2010

Asn Asn Ala Val Val Asp Ala Thr Asn Ala Ala Thr Ser Lys Gly
2015              2020              2025

Phe Ala Leu Gln Ala Ala Asp Gly Ala Lys Val Gln Lys Asn Leu
2030              2035              2040

-continued

```
Gly Glu Ala Val Glu Val Val Gly Ala Asp Ser Asn Ile Thr Thr
    2045                2050                2055
Lys Val Ala Gly Gly Gln Val Ala Ile Glu Leu Asn Lys Asn Leu
    2060                2065                2070
Asn Asn Leu Thr Gly Ile Thr Val Asn Asp Gly Thr Asn Gly Thr
    2075                2080                2085
Asn Gly Ser Thr Val Ile Gly Lys Asp Gly Ile Ser Val Lys Asp
    2090                2095                2100
Gly Ser Gly Asn Thr Ile Ala Gly Val Asp Asn Thr Ala Leu Thr
    2105                2110                2115
Val Lys Asp Gly Ser Gly Asn Thr Glu Thr Ser Ile Asn Gln Ala
    2120                2125                2130
Ile Asn Thr Leu Asn Ala Ala Gln Gly Glu Thr Asp Lys Phe Ala
    2135                2140                2145
Val Lys Tyr Asp Lys Asn Ala Asp Gly Ser Val Asn Tyr Asn Asn
    2150                2155                2160
Ile Thr Leu Ala Gly Thr Thr Ala Ser Ser Thr Gln Asp Ala Thr
    2165                2170                2175
Thr Gly Lys Ile Thr Thr Thr Gly Gly Thr Ser Leu Asn Asn Val
    2180                2185                2190
Ala Ser Ala Gly Asp Tyr Lys Asp Val Ala Asn Ala Ser Lys Gly
    2195                2200                2205
Val Asn Ala Gly Asp Leu Asn Asn Ala Val Val Asp Ala Thr Asn
    2210                2215                2220
Ala Ala Thr Ser Lys Gly Phe Ala Leu Gln Ala Ala Asp Gly Ala
    2225                2230                2235
Lys Val Gln Lys Asn Leu Gly Glu Ala Val Glu Val Val Gly Ala
    2240                2245                2250
Asp Ser Asn Ile Thr Thr Lys Val Ala Gly Gly Gln Val Ala Ile
    2255                2260                2265
Glu Leu Asn Lys Asn Leu Asn Asn Leu Thr Gly Ile Thr Val Asn
    2270                2275                2280
Asp Gly Thr Asn Gly Thr Asn Gly Ser Thr Val Ile Gly Lys Asp
    2285                2290                2295
Gly Ile Ser Val Lys Asp Gly Ser Gly Asn Thr Ile Ala Gly Val
    2300                2305                2310
Asp Asn Thr Ala Leu Thr Val Lys Asp Gly Ser Gly Asn Thr Glu
    2315                2320                2325
Thr Ser Ile Asn Gln Ala Ile Asn Thr Leu Asn Ala Ala Gln Gly
    2330                2335                2340
Glu Thr Asp Lys Phe Ala Val Lys Tyr Asp Lys Asn Ala Asp Gly
    2345                2350                2355
Ser Ala Asn Tyr Asn Asn Val Thr Leu Ala Gly Thr Asn Gly Thr
    2360                2365                2370
Ile Ile Ser Asn Val Lys Ala Gly Ala Val Thr Ser Thr Ser Thr
    2375                2380                2385
Asp Ala Ile Asn Gly Ser Gln Leu Tyr Gly Val Ala Asn Ser Val
    2390                2395                2400
Lys Asn Ala Ile Gly Gly Ser Thr Thr Ile Asp Ala Thr Thr Gly
    2405                2410                2415
Ala Ile Thr Thr Thr Asn Ile Gly Gly Thr Gly Ser Asn Thr Ile
    2420                2425                2430
Asp Gly Ala Ile Ser Ser Ile Lys Asp Ser Ala Thr Lys Ala Lys
```

-continued

```
            2435                2440                2445

Thr  Thr  Val  Ser  Ala  Gly  Asp  Asn  Val  Val  Thr  Ser  Gly  Thr
     2450                2455                2460

Asn  Ala  Asp  Gly  Ser  Thr  Asn  Tyr  Glu  Val  Ala  Thr  Ala  Lys  Asp
     2465                2470                2475

Val  Asn  Phe  Asp  Lys  Val  Thr  Val  Gly  Ser  Val  Val  Asp  Lys
     2480                2485                2490

Ser  Ser  Asn  Thr  Ile  Lys  Gly  Leu  Ser  Asn  Thr  Thr  Trp  Asn  Gly
     2495                2500                2505

Thr  Ala  Val  Ser  Gly  Gln  Ala  Ala  Thr  Glu  Asp  Gln  Leu  Lys  Thr
     2510                2515                2520

Val  Ser  Asp  Ala  Gln  Gly  Glu  Thr  Asp  Lys  Phe  Ala  Val  Lys  Tyr
     2525                2530                2535

Asp  Lys  Asn  Ala  Asp  Gly  Ser  Ala  Asn  Tyr  Asn  Ser  Ile  Thr  Ala
     2540                2545                2550

Gly  Asn  Gly  Asn  Gly  Thr  Ala  Ala  Thr  Ile  Gly  Thr  Asp  Thr  Ala
     2555                2560                2565

Gly  Asn  Ser  Val  Val  Thr  Ser  Gly  Gly  Thr  Lys  Ile  Ser  Asn  Val
     2570                2575                2580

Ala  Asn  Gly  Val  Asn  Ala  Ser  Asp  Ala  Val  Asn  Lys  Gly  Gln  Leu
     2585                2590                2595

Asp  Ser  Leu  Ser  Thr  Gly  Leu  Thr  Asn  Thr  Gly  Phe  Gly  Leu  Lys
     2600                2605                2610

Ala  Ala  Asp  Gly  Asn  Thr  Val  Asn  Lys  Lys  Leu  Gly  Glu  Ala  Val
     2615                2620                2625

Asp  Val  Val  Gly  Ala  Asp  Ser  Asn  Ile  Thr  Thr  Lys  Val  Ala  Gly
     2630                2635                2640

Gly  Gln  Val  Ala  Ile  Glu  Leu  Asn  Lys  Asn  Leu  Asn  Asn  Leu  Thr
     2645                2650                2655

Gly  Ile  Thr  Val  Asn  Asp  Gly  Thr  Asn  Gly  Thr  Asn  Gly  Ser  Thr
     2660                2665                2670

Val  Ile  Gly  Lys  Asp  Gly  Ile  Ser  Ile  Lys  Asp  Gly  Ser  Gly  Asn
     2675                2680                2685

Thr  Ile  Ala  Gly  Val  Asp  Asn  Thr  Ala  Leu  Thr  Val  Lys  Asp  Ser
     2690                2695                2700

Ser  Gly  Asn  Thr  Glu  Thr  Ser  Ile  Asn  Gln  Ala  Ile  Asn  Thr  Leu
     2705                2710                2715

Asn  Ala  Ala  Gln  Gly  Glu  Thr  Asp  Lys  Phe  Ala  Val  Lys  Tyr  Asp
     2720                2725                2730

Lys  Asn  Ala  Asp  Gly  Ser  Val  Asn  Tyr  Asn  Asn  Val  Thr  Leu  Ala
     2735                2740                2745

Gly  Thr  Asn  Gly  Thr  Ile  Ile  Arg  Asn  Val  Lys  Ala  Gly  Ala  Val
     2750                2755                2760

Thr  Ser  Thr  Ser  Thr  Asp  Ala  Ile  Asn  Gly  Ser  Gln  Leu  Tyr  Asp
     2765                2770                2775

Ile  Ala  Asn  Ser  Val  Lys  Asn  Ala  Ile  Gly  Gly  Ser  Thr  Thr  Arg
     2780                2785                2790

Asp  Val  Thr  Thr  Gly  Ala  Ile  Thr  Thr  Thr  Asn  Ile  Gly  Gly  Thr
     2795                2800                2805

Gly  Ser  Asn  Thr  Ile  Asp  Gly  Ala  Ile  Ser  Ser  Ile  Lys  Asp  Ser
     2810                2815                2820

Ala  Thr  Lys  Ala  Lys  Thr  Thr  Ile  Ser  Ala  Gly  Asp  Asn  Val  Val
     2825                2830                2835
```

-continued

Val Thr Ser Gly Thr Asn Ala Asp Gly Ser Thr Asn Tyr Glu Val
2840            2845            2850

Ala Thr Ala Lys Asp Val Asn Phe Asp Lys Val Thr Val Gly Asn
2855            2860            2865

Val Val Val Asp Lys Ala Asn Asp Thr Ile Gln Gly Leu Ser Asn
2870            2875            2880

Lys Asp Leu Asn Ser Thr Asp Phe Ala Thr Lys Gly Arg Ala Ala
2885            2890            2895

Thr Glu Glu Gln Leu Lys Ala Val Ile Thr Ser Asn Ile Thr Glu
2900            2905            2910

Val Val Asp Gly Asn Gly Asn Lys Val Asn Ile Ile Asp Gln Val
2915            2920            2925

Val Asn Thr Lys Pro Asp Asn Lys Asn Gln Asp Ser Leu Phe Leu
2930            2935            2940

Thr Tyr Asp Lys Gln Gly Gln Glu Thr Thr Asp Arg Leu Thr Ile
2945            2950            2955

Gly Gln Thr Val Gln Lys Met Asn Thr Asp Gly Ile Lys Phe Phe
2960            2965            2970

His Thr Asn Ala Asp Thr Ser Lys Gly Asp Leu Gly Thr Thr Asn
2975            2980            2985

Asp Ser Ser Ala Gly Gly Leu Asn Ser Thr Ala Ile Gly Val Asn
2990            2995            3000

Ala Ile Val Ala Asn Gly Ala Asp Ser Ser Val Ala Leu Gly His
3005            3010            3015

Asn Thr Lys Val Asn Gly Lys Gln Ser Ile Ala Ile Gly Ser Gly
3020            3025            3030

Ala Glu Ala Leu Gly Asn Gln Ser Ile Ser Ile Gly Thr Gly Asn
3035            3040            3045

Lys Val Thr Gly Asp His Ser Gly Ala Ile Gly Asp Pro Thr Ile
3050            3055            3060

Val Asn Gly Ala Asn Ser Tyr Ser Val Gly Asn Asn Asn Gln Val
3065            3070            3075

Leu Thr Asp Asp Thr Phe Val Leu Gly Asn Asn Val Thr Lys Thr
3080            3085            3090

Ile Ala Gly Ser Val Val Leu Gly Asn Gly Ser Ala Ala Thr Thr
3095            3100            3105

Gly Ala Gly Glu Ala Gly Tyr Ala Leu Ser Val Ala Thr Asn Ala
3110            3115            3120

Asp Lys Ala Ala Ile Thr Lys Thr Thr Ser Ser Thr Gly Ala Val
3125            3130            3135

Ala Val Gly Asp Ala Ser Ser Gly Ile Tyr Arg Gln Ile Thr Gly
3140            3145            3150

Val Ala Ala Gly Ser Val Asp Ser Asp Ala Val Asn Val Ala Gln
3155            3160            3165

Leu Lys Ala Val Gly Asn Gln Val Val Thr Thr Gln Thr Thr Leu
3170            3175            3180

Val Asn Ser Leu Gly Gly Asn Ala Lys Val Asn Ala Asp Gly Thr
3185            3190            3195

Ile Thr Gly Pro Thr Tyr Asn Val Ala Gln Gly Asn Gln Thr Asn
3200            3205            3210

Val Gly Asp Ala Leu Thr Ala Leu Asp Asn Ala Ile Asn Thr Ala
3215            3220            3225

Ala Thr Thr Ser Lys Ser Thr Val Ser Asn Gly Gln Asn Ile Val
3230            3235            3240

-continued

```
Val Ser Lys Ser Lys Asn Ala Asp Gly Ser Asp Asn Tyr Glu Val
    3245            3250            3255

Ser Thr Ala Lys Asp Leu Thr Val Asp Ser Val Lys Ala Gly Asp
    3260            3265            3270

Thr Val Leu Asn Asn Ala Gly Ile Thr Ile Gly Asn Asn Ala Val
    3275            3280            3285

Val Leu Asn Asn Thr Gly Leu Thr Ile Ser Gly Gly Pro Ser Val
    3290            3295            3300

Thr Leu Ala Gly Ile Asp Ala Gly Asn Lys Thr Ile Gln Asn Val
    3305            3310            3315

Ala Asn Ala Val Asn Ala Thr Asp Ala Val Asn Lys Gly Gln Leu
    3320            3325            3330

Asp Ser Ala Ile Asn Asn Val Asn Asn Asn Val Asn Glu Leu Ala
    3335            3340            3345

Asn Asn Ala Val Lys Tyr Asp Asp Ala Ser Lys Asp Lys Ile Thr
    3350            3355            3360

Leu Gly Gly Gly Ala Thr Gly Thr Thr Ile Thr Asn Val Lys Asp
    3365            3370            3375

Gly Thr Val Ala Gln Gly Ser Lys Asp Ala Val Asn Gly Gly Gln
    3380            3385            3390

Leu Trp Asn Val Gln Gln Gln Val Asp Gln Asn Thr Thr Asp Ile
    3395            3400            3405

Ser Asn Ile Lys Asn Asp Ile Asn Asn Gly Thr Val Gly Leu Val
    3410            3415            3420

Gln Gln Ala Gly Lys Asp Ala Pro Val Thr Val Ala Lys Asp Thr
    3425            3430            3435

Gly Gly Thr Thr Val Asn Val Ala Gly Thr Asp Gly Asn Arg Val
    3440            3445            3450

Val Thr Gly Val Lys Glu Gly Ala Val Asn Ala Thr Ser Lys Asp
    3455            3460            3465

Ala Val Asn Gly Ser Gln Leu Asn Thr Thr Asn Gln Ala Val Val
    3470            3475            3480

Asn Tyr Leu Gly Gly Gly Ala Gly Tyr Asp Asn Ile Thr Gly Ser
    3485            3490            3495

Phe Thr Ala Pro Ser Tyr Thr Val Gly Asp Ser Lys Tyr Asn Asn
    3500            3505            3510

Val Gly Gly Ala Ile Asp Ala Leu Asn Gln Ala Asp Gln Ala Leu
    3515            3520            3525

Asn Ser Lys Ile Asp Asn Val Ser Asn Lys Leu Asp Asn Ala Phe
    3530            3535            3540

Arg Ile Thr Asn Asn Arg Ile Asp Asp Val Glu Lys Lys Ala Asn
    3545            3550            3555

Ala Gly Ile Ala Ala Ala Met Ala Leu Glu Ser Ala Pro Tyr Val
    3560            3565            3570

Pro Gly Lys Tyr Thr Tyr Ala Ala Gly Ala Ala Tyr His Gly Gly
    3575            3580            3585

Glu Asn Ala Val Gly Val Thr Leu Arg Lys Thr Ala Asp Asn Gly
    3590            3595            3600

Arg Trp Ser Ile Thr Gly Gly Val Ala Ala Ala Ser Gln Gly Asp
    3605            3610            3615

Ala Ser Val Arg Ile Gly Ile Ser Gly Val Ile Asp
    3620            3625            3630
```

<210> SEQ ID NO 3
<211> LENGTH: 795
<212> TYPE: DNA
<213> ORGANISM: Acinetobacter sp. Tol5

<400> SEQUENCE: 3

```
atgaaagcat taacaaaaa aattatgttt ggtgtattca gcggtcttgt gatgtcattg      60
agccatgctg ctgaagtcga aagtgcaaat acgcaagaaa tccattttcc tgaaatcaaa    120
gacagctatt taaaacaagt gaaccgttat gaatatgacg atgtcgcacg tttagacaag    180
ggattaacca agatcagat tcgccatatt ttgggaaatc ctcaattctc tgaaggtctt     240
tttgcggtta agacatggaa ttatgtattg gatattcgtg agcctaactc aaaccaatat    300
aagcgttgcc aattacgcat agattttgat aagcaatacc gttcagacaa tctatattgg    360
aaaggtgaac aatgccaagg cttaatggct tgggggatta taatcagtc tgagactgag     420
caaacgactc tagcacctgg tgggcagtct gcaagtgttt tgttttattt tgatcatgcg    480
gataaaaatg gtgtaaagaa cgctgaagtg attcgtaaaa tcgcagatca gattaaacaa    540
tctgatgcga atagccctgt ttttgtggct ggatatactg atcgtttagg atcatttcag    600
tataaccaac gtttatctgc ccaaagagcg aatacagtcg ttgaactctt gaagcaacaa    660
ggcattcgtg gcgagcaaat tcagtacagt gctgaaaata aaacagatgt gtaccaaaag    720
tgcgcaggga tcaataaaaa gatccaactg gttgaatgtc tagcacctaa ccgtcgtgtg    780
aatatcacgt ggtaa                                                    795
```

<210> SEQ ID NO 4
<211> LENGTH: 264
<212> TYPE: PRT
<213> ORGANISM: Acinetobacter sp. Tol5

<400> SEQUENCE: 4

```
Met Lys Ala Phe Asn Lys Lys Ile Met Phe Gly Val Phe Ser Gly Leu
1               5                   10                  15

Val Met Ser Leu Ser His Ala Ala Glu Val Glu Ser Ala Asn Thr Gln
            20                  25                  30

Glu Ile His Phe Pro Glu Ile Lys Asp Ser Tyr Leu Lys Gln Val Asn
        35                  40                  45

Arg Tyr Glu Tyr Asp Asp Val Ala Arg Leu Asp Lys Gly Leu Thr Lys
    50                  55                  60

Asp Gln Ile Arg His Ile Leu Gly Asn Pro Gln Phe Ser Glu Gly Leu
65                  70                  75                  80

Phe Ala Val Lys Thr Trp Asn Tyr Val Leu Asp Ile Arg Glu Pro Asn
                85                  90                  95

Ser Asn Gln Tyr Lys Arg Cys Gln Leu Arg Ile Asp Phe Asp Lys Gln
            100                 105                 110

Tyr Arg Ser Asp Asn Leu Tyr Trp Lys Gly Glu Gln Cys Gln Gly Leu
        115                 120                 125

Met Ala Trp Gly Ile Asn Asn Gln Ser Glu Thr Glu Gln Thr Thr Leu
    130                 135                 140

Ala Pro Gly Gly Gln Ser Ala Ser Val Leu Phe Tyr Phe Asp His Ala
145                 150                 155                 160

Asp Lys Asn Gly Val Lys Asn Ala Glu Val Ile Arg Lys Ile Ala Asp
                165                 170                 175

Gln Ile Lys Gln Ser Asp Ala Asn Ser Pro Val Phe Val Ala Gly Tyr
            180                 185                 190

Thr Asp Arg Leu Gly Ser Phe Gln Tyr Asn Gln Arg Leu Ser Ala Gln
```

```
                  195                 200                 205
Arg Ala Asn Thr Val Val Glu Leu Leu Lys Gln Gln Gly Ile Arg Gly
        210                 215                 220

Glu Gln Ile Gln Tyr Ser Ala Glu Asn Lys Thr Asp Val Tyr Gln Lys
225                 230                 235                 240

Cys Ala Gly Ile Asn Lys Lys Ile Gln Leu Val Glu Cys Leu Ala Pro
                245                 250                 255

Asn Arg Arg Val Asn Ile Thr Trp
            260

<210> SEQ ID NO 5
<211> LENGTH: 11858
<212> TYPE: DNA
<213> ORGANISM: Acinetobacter sp. Tol5

<400> SEQUENCE: 5
ttgctttaat tgtatgtaaa ttgttaaata aaaaaaattg tacattttat atgcattgct      60
aaagcagaac ctactgccca aaatgcatct cctaaggaaa agcgatatga ataaaatcta     120
caaagtgatt tggaatgcga cttttgttgg catgggttgca gtatctgaat tggcaaaagg    180
gaaaaccaaa tctacgacat caaaatccaa agctaaatca ttatcttcat ctgtaatagt    240
tggtgggata atattaacaa caccttta tc tttaatagca gctactgttc aagttggagg    300
gggaactaat tctggaacaa ctgctacagc ttctacgaat tgtgcagact tatataatta    360
tcaaaatcct gagaactcag gctctggagc ggctgggaat tataatgcag gaaatccaag    420
tgtgtgttcg atcgctatag gtgaaaacgc acaaggtggt acttctggaa ctggagggtc    480
gccagggata gcgataggtg gaaattctaa agctacgggt ggtttatctg ttgctatagg    540
cggatatgct caagcgacaa atgttggaag tattgcttta ggcacagcag ctttatcaag    600
tggttttaac agtttagcaa tatccagaca agctgctgca acgaataact attcaatagc    660
tataggtaca acttcagttt cgaaaggagt tggatcgatt gctatgggc attcaacgaa     720
tgcttctgga gatcaatcga tagcaattgg tagctcggat gctgttaatt cagcaacagc    780
aacaacaaca tacgatggta caacaaatac tcaagcatca ggtagtaaat cgattgctat    840
aggtgcaagc gcaaaggcat caaccaataa cagcattgca ctaggtgcag gatcggtaac    900
ttctgcacaa tctggtaatt cttatcttac tggtgtaggt gcatcagcta caaatggtgt    960
tgtatctgtt ggaacttcaa ctgcaacacg tcgtatccaa aatgtagcag atggttcagc   1020
cgcttcagat gctgtgacag ttgctcagtt ggataaagct tatgatgata caaatggtcg   1080
tttagctgct gctttaggta caggtagtgg tgctgcctat aatgcagcaa acaatacata   1140
taccgctcca acgaatattg ggggaacagg taaaaatacg attgatgatg caattaaagc   1200
aactcaacga agtgtagtcg ctggatcaaa tattgtcgtt accccgacga cagcttctga   1260
tggttcaata tcgtattcgg ttgctacaag cgcaacaccg acgtttacaa gtataactgt   1320
aaacaatgca ccaacggcag gtacagatgc gaccaacaag acttatgtag actcaaaagc   1380
agcagcatcg agaacagaag tagcagctgg aagcaatgta tctggtgtag taaaaacgac   1440
aggcgcaaac ggtcaagacg tttatacagt aaatgccaat ggtacgactg catcagcagg   1500
ttcttcagca gttaccgtaa caccaggcac gaaagatgca aataatgtca ctgactataa   1560
agtagactta tcagcgacta caaaaaccga tatccaaaaa ggtgtagatg caaaaaatgc   1620
tgtagatacc gcaggtctaa aatttaaagg tgatacagca accacaagca ataccaagaa   1680
attaggtgac accgtttcga ttacgggtga tacgaacatt agtacagttg cgacaacaga   1740
```

```
tggtgtacag gttaagttaa atccaaactt ggatttagga gcaactggta gcgttaaaac    1800
gggtaatacc acgattaaca atgcaggtgt aacagctgat caagttacgg ttggtggtgt    1860
tgttattaac aacacatcag gtattaatgc tggtggtaaa gcgattacta atgtagcagc    1920
accaacaaat aacacagatg ctgctaacaa gaagtatgta gatgatgcag gtacagcatt    1980
aaccaatttg ggctttggat taaaagcaca agatggtacg actgtgaaca agaaattagg    2040
tgaagcagtt gatattgttg gttcaaacag caacatcagt acaaaagtaa atgcaggcaa    2100
agtagaagtt gcactatcca atacattgga cttaggtact acaggtagcg ttactacggg    2160
ttcaactgta attaacaata ctggtgttac ggcaactcag gttaccgcaa acaaagtcac    2220
aataaacaat gcaccaacag caggtacaga tgcgaccaac aagacttatg tagactcaaa    2280
agcagcagca tcaagaacag aagtcgcagc tggaagcaat gtatctggtg tagtaaaaac    2340
gacaggcgca aacggtcaag atatttatgc agtaaatgcc aatggtacga ctgcatcagc    2400
aggttcttca gcagttaccg taacaccagg cacgaaagat gcaaataatg tcactgacta    2460
taaagtagac ttgtcagcga ctacaaaaac cgatattcaa aaaggtgtag atgcaaaaaa    2520
tgctgtagat actgcaggtc taaaatttaa aggtgataca gcaaccacaa gcaataccaa    2580
gaaattaggt gacaccgttt cgattacggg tgatacgaac attagtacag ttgcaacaac    2640
tgatggtgta caggttaagt taaatccaaa cttagattta ggagcaactg gtagcgttaa    2700
aacgggtaat accacgatta acaatgcagg tgtaacagct gaccaagtta cggttggtgg    2760
tgttgttatt aacaacacat caggtattaa tgctggtggt aaagcgatta ccaatgtagc    2820
agcaccaaca aataacacag atgctgctaa caagaagtat gtagatgacg caggtacagc    2880
attaaccaat ttgggctttg gattaaaagc gcaagatggt acgactgtga acaagaaatt    2940
aggtgaagca gttgatattg ttggttcaaa cagcaacatc agtacaaaag taaatgcagg    3000
caaagtagaa gttgcactat ccaatacatt ggacttaggt actacaggta gcgttactac    3060
gggttcaact gtaattaaca atgctggtgt tacggcaact caagttaccg caaacaaagt    3120
cacagttaat aatgcaccaa cagcaggtac agatgcgacc aataaaactt atgtagactc    3180
aaaagcagcg gcatcaagaa cagaagtcgc agctggaagc aatgtatctg gcgtagtaaa    3240
aacgacaggt gcaaacggtc aagacgtttt acagtaaat gccaatggta cgactgcatc    3300
agcaggttct tcagcagtta ccgtaacacc aggcacgaaa gatgcaaata atgtcactga    3360
ctataaagta gacttgtcag cgactacaaa aaccgatatt caaaaggtg tagatgcaaa    3420 aaatgctgta gataccgcag gtctaaaatt taaaggtgat acagcaacca caagcaatac    3480
caagaaatta ggtgacaccg tttcgattac gggtgatacg aacattagta cagttgcgac    3540
aactgatggt gtacaggtta agctaaatcc aaacttggat ttaggagcaa ctggtagcgt    3600
taaaacgggt aataccacga ttaacaatgc aggtgtaaca gctgatcaag ttacagttgg    3660
tggtgttgtt attaacaaca catcaggtat taatgctggt ggtaaagcga ttaccaatgt    3720
agcagcacca acaaataaca cagatgctgc taacaagaag tatgtagatg atgcaggtac    3780
agcattaacc aatttgggct ttggattaaa agcgcaagat ggtacgactg tgaacaagaa    3840
attaggcgaa gcagttgaag ttgttggtgc ggacagtaac atcaccacga agttgcagg    3900 cggtcaggtt gcaattgagt taaataaaaa cctcaacaac ttaactggca ttaccgtgaa    3960
cgatggaacc aatggcacca atggttcaac tgtgattggt aaagatggta tttcggttaa    4020
agatggttca ggcaatacca ttgcaggtgt agataacaca gcgttgacag ttaaagatgg    4080
cagtggcaac acagaaacca gcattaacca agcgatcaac acgttaaatg cagcgcaagg    4140
```

-continued

```
tgaaactgat aagtttgcag tgaagtacga caaaaatgct gatggcagtg tgaactacaa    4200
caacatcaca ttggcaggta cgactgcaag cagtacacaa gatgcaacta caggcaagat    4260
caccacaaca ggtggaacaa gcttgaacaa tgttgcaagt gcgggtgact acaaagatgt    4320
tgccaatgca agcaaaggtg taaacgcagg tgacttaaac aatgcagttg ttgatgcaac    4380
caatgcagca accagcaaag gctttgcatt acaagcagca gatggcgcta agttcagaa     4440
gaacctaggc gaagcagttg aagttgtcgg tgccgacagc aacatcacca caaaagttgc    4500
aggcggtcag gttgcaattg agttaaataa aaaccctcaac aacttaactg gcattaccgt   4560
gaacgatgga accaatggca ccaatggttc aactgtgatt ggtaaagatg gtatttcagt    4620
taaagacggt tcaggcaata ccattgcagg tgtagataac acagcgttga cagttaaaga    4680
tggcagtgga aacacagaaa ccagcattaa ccaagcgatc aacacgttaa atgcagcgca    4740
aggtgaaact gataagtttg cagtgaagta cgacaaaaat acggatggta gtaccaacta    4800
caacagtatt actgcaggca atggtaacgg tactgcagca acgatcggaa ctgacacagc    4860
aggtaatagt gttgtgacca gtggcggaac taaaattagt aatgttgcga atggtgtcaa    4920
tgcaagtgat gcagtaaaca aaggtcaatt ggatagctta agtacaggtc ttaccaatac    4980
aggctttggt ttaaaagcag cagatggcaa caccgttaac aaaaaattag gcgaagcagt    5040
agacgttgtc ggtgctgaca gcaacatcac cacgaaagtt gcaggcggtc aggttgcgat    5100
tgagttaaat aaaaaacctca acaacttaac tggcattacc gtgaacgatg gaaccaatgg    5160
caccaatggt tcaactgtga ttggtaaaga tggtatttcg attaaagatg gttcaggcaa    5220
taccattgca ggtgtagata acacagcgtt gacagttaaa gatggcagtg gcaacacaga    5280
aaccagcatt aaccaagcga tcaacacgtt aaatgcagcg caaggtgaaa ctgacaagtt    5340
tgcagtgaag tacgacaaga atgctgatgg cagtgcaaac tacaacaaca tcacattggc    5400
aggtacgact gcaagtagca cgcaagatgc aacaacaggc aagatcacca caacaggtgg    5460
aacaagcttg aacaacgttg caagtgcagg tgactacaaa gatgttgcca atgcaagcaa    5520
aggtgtaaac gcaggtgact tgaacaatgc agttgttgat gcaaccaatg cagcaaccag    5580
caaaggcttt gcattacaag cagcagatgg cgctaaagtt cagaagaacc taggcgaagc    5640
agttgaagtt gtcggtgcgg acagcaacat caccacaaaa gtagtgggtg acaagttgc     5700
gattgagtta aataaaaacc tcaacaactt aactggcatt accgtgaacg atggaaccaa    5760
tggcacaaat ggttcaactg tgattggtaa agatggtatt tcggttaaag atggttcagg    5820
taataccatt gcaggtgtag ataacacagc gttgacagtt aaagatggca gtggcaacac    5880
agaaaccagc attaaccaag cgatcaacac gttaaatgca gcgcaaggtg aaactgataa    5940
gtttgcagtg aagtacgaca aaaatgctga tggcagtgtg aactacaaca acatcacatt    6000
ggcaggtacg actgcaagca gtacacaaga tgcaactaca ggcaagatca ccacaacagg    6060
tggaacaagc ttgaacaatg ttgcaagtgc gggtgactac aaagatgttg ccaatgcaag    6120
caaaggtgta aacgcaggtg acttaaacaa tgcagttgtt gatgcaacca atgcagcaac    6180
cagcaaaggc tttgcattac aagcagcaga tggcgctaaa gttcagaaga acctaggcga    6240
agcagttgaa gttgtcggtg ccgacagcaa catcaccaca aaagttgcag gcggtcaggt    6300
tgcaattgag ttaaataaaa acctcaacaa cttaactggc attaccgtga acgatggaac    6360
caatggcacc aatggttcaa ctgtgattgg taaagatggt atttcagtta aagacggttc    6420
aggcaatacc attgcaggtg tagataacac agcgttgaca gttaaagatg gcagtggcaa    6480
cacagaaacc agcattaacc aagcgatcaa cacgttaaat gcagcgcaag gtgaaactga    6540
```

```
taagtttgca gtgaagtacg acaaaaatgc tgatggcagt gtgaactaca acaacatcac    6600
attggcaggt acgactgcaa gcagtacaca agatgcaact acaggcaaga tcaccacaac    6660
aggtggtaca agcttgaaca atgttgcaag tgcgggtgac tacaaagatg ttgccaatgc    6720
aagcaaaggt gtaaacgcag gtgacttgaa caatgcagtt gttgatgcaa ccaatgcagc    6780
gaccagcaaa ggcttttgcat tacaagcagc agatggcgct aaagttcaga agaacctagg    6840
cgaagcagtt gaagttgttg gtgcggacag taacatcacc acgaaagttg caggcggtca    6900
ggttgcaatt gagttaaata aaaaacctcaa caacttaact ggcattaccg tgaacgatgg    6960
aaccaatggc accaatggtt caactgtgat tggtaaagat ggtatttcgg ttaaagatgg    7020
ttcaggcaat accattgcag gtgtagataa cacagcgttg acagttaaag atggcagtgg    7080
caacacagaa accagcatta accaagcgat caacacgtta aatgcagcgc aaggtgaaac    7140
tgataagttt gcagtgaagt acgacaaaaa tgctgatggc agtgcaaact ataacaatgt    7200
cactttagct ggtacaaatg gcacaataat cagcaatgtt aaagcgggtg ctgtgacctc    7260
aacatctact gatgcgatca atggtagcca attatatggt gttgcaaaca gcgtgaagaa    7320
tgcaattggt ggttcaacca caattgatgc aacgactggt gcaatcacga cgaccaatat    7380
tggtggtaca ggttcaaata cgattgatgg tgcaatcagc agtattaaag attcagcgac    7440
taaagcgaaa accacggtaa gtgctgggga taatgttgtc gttacatcgg gtaccaatgc    7500
agatggctca acaaactatg aagttgcgac agcgaaagac gttaactttg acaaagtgac    7560
tgtaggtagt gttgttgtag ataaatcaag caatacaatc aaaggattaa gtaataccac    7620
ttggaacgga acagcagtat caggtcaagc ggcgacagaa gaccagttaa aaacggtcag    7680
cgatgcgcaa ggtgaaactg ataagtttgc agtgaagtac gacaaaaatg ctgatggcag    7740
tgcgaactac aacagtatta ctgcaggcaa tggtaacggt actgcagcaa cgatcggaac    7800
tgacacagca ggtaatagtg ttgtgaccag tggcggaact aaaaattagta atgttgcgaa    7860 tggtgtcaat gcaagtgatg cagtaaacaa aggtcaattg gatagcttaa gtacaggtct    7920
taccaataca ggctttggtt taaaagcagc agatggcaac accgttaaca aaaaattagg    7980
cgaagcagta gacgttgtcg gtgctgacag caacatcacc acgaaagttg caggcggtca    8040
ggttgcgatt gagttaaata aaaaacctcaa caacttaact ggcattaccg tgaacgatgg    8100
aaccaatggc accaatggtt caactgtgat tggtaaagat ggtatttcga ttaaagatgg    8160
ttcaggcaat accattgcag gtgtagataa cacagcgttg acggttaaag atagcagtgg    8220
caacacagaa accagcatta accaagcgat caacacgtta aatgcagcgc aaggtgaaac    8280
tgataagttt gcagtgaagt acgataagaa tgctgatggc agtgtgaact ataacaatgt    8340
cactttagca ggtacaaatg gcacaataat cagaaatgtt aaagcgggtg ctgtgacctc    8400
aacatctact gatgcgatca atggtagcca attatacgat attgcaaaca gcgtgaagaa    8460
tgcaattggt ggttcaacca caagagatgt aacgactggt gcaatcacaa cgaccaatat    8520
tggtggtaca ggttcaaaca cgattgatgg tgcaatcagc agtattaaag attcagcgac    8580
taaagcgaaa accacgataa gtgctgggga taatgttgtc gttacatcgg gtaccaatgc    8640
agatggctca acaaactatg aagttgcgac agcgaaagac gttaactttg acaaagtaac    8700
tgtaggtaat gttgttgttg ataaggcaaa tgacacgatc caaggtttga gcaataaaga    8760
tctaaattca actgattttg cgaccaaagg tagagctgcg actgaagaac agttaaaagc    8820
agtgattacc agtaatatca cggaagttgt ggatggtaat ggcaacaagg tgaatatttat    8880 tgaccaagtt gtaaatacca aacctgacaa taagaaccaa gattcattgt tcttaacgta    8940
```

```
tgacaaacaa ggtcaagaaa ccacagatcg cctaacgatt ggtcaaacgg tacagaagat    9000
gaatactgat ggtattaaat tcttccatac caatgccgat acatcaaaag gtgatttggg    9060
tacaacaaat gactcaagtg caggtggttt aaactctaca gcaattggtg taaatgcgat    9120
tgttgcgaat ggtgcagata gttcagttgc tttaggtcat aacaccaaag tcaatggtaa    9180
acaatcaatt gcaattggtt ctggtgcaga agctttaggc aatcaatcga tcagtattgg    9240
tacaggcaat aaagtcactg gtgatcattc gggtgcgatt ggtgatccaa ctattgtaaa    9300
tggtgcaaac agctactctg tgggtaataa caaccaagta cttacagatg acactttcgt    9360
acttggaaac aatgtcacca aaactattgc tggttcagta gtattgggta acggttcagc    9420
tgcaacgaca ggtgctggtg aggcaggcta tgccttatct gtagcaacaa atgcagataa    9480
agccgcgatc actaaaacta cgtcaagcac tggtgctgtt gcagttggtg atgcgtcgag    9540
cggtatttat cgtcaaatta ccggtgttgc tgcgggtagc gtagattcag atgctgtgaa    9600
cgttgcacag ttaaaagcgg tgggtaacca agttgtaacg actcaaacta cattggtgaa    9660
cagtttgggt ggtaacgcta agtaaatgc agacggtacg attacaggac caacttataa    9720
tgttgctcaa ggtaatcaga ccaatgttgg tgatgcatta actgcgcttg ataacgcaat    9780
taatactgcg gcaacaacat ctaaatcgac tgtttctaat ggtcagaata ttgttgtcag    9840
caagagcaaa aatgcagatg gttcagacaa ctatgaagta tcaacagcaa aagacttgac    9900
agttgattct gtcaaagcgg gtgatacggt tctgaataat gcaggtatta caattggcaa    9960
taacgcagtt gtattgaaca acactggatt aaccattagt ggtggaccaa gtgttacctt   10020
ggcaggcatc gatgcaggca ataaaaccat tcaaaatgtt gcgaatgcag taaatgcaac   10080
agatgcagtc aacaaagggc aattggacag cgcaattaac aatgtgaata acaatgtaaa   10140
tgagcttgcc aacaacgctg ttaaatatga cgatgcatca aaagataaga tcacacttgg   10200
tggtggggca actggtacaa caatcaccaa tgtgaaagat ggtactgttg cgcaaggttc   10260
taaagatgct gtgaatggcg gtcaattgtg gaatgttcaa caacaagttg atcagaacac   10320
aactgatatt agcaatatca aaaatgatat taacaacggt actgttggtt tggttcaaca   10380
agcaggtaaa gatgcaccag tgacggttgc aaaagatact ggcggtacaa cggtgaatgt   10440
cgctggaaca gatggcaacc gagtagtgac aggtgttaag gaaggtgcag tgaatgcaac   10500
atctaaagat gctgtcaatg gtagtcaatt gaatacaacc aaccaagcgg tagtcaatta   10560
tcttggtggt ggggcaggtt atgacaacat tacaggtagc ttcacagcgc caagttatac   10620
ggtaggtgac tcgaaataca acaatgttgg tggcgcaatt gatgcattga atcaagcaga   10680
tcaagcattg aatagcaaaa ttgacaatgt cagtaacaag ttggataacg cattccgtat   10740
taccaacaac cgtattgatg atgtagagaa aaaagccaat gctggtattg ccgctgcgat   10800
ggctctggaa tcagcaccat atgtcccagg taaatatacc tatgcagcag gcgcagctta   10860
ccacggtggt gaaaatgcgg taggtgtgac tttacgtaaa actgcagaca atggtcgttg   10920
gtcgattaca ggcggtgtag ctgcagcgtc tcaaggcgat gcaagtgttc gtatcggtat   10980
cagcggtgtg attgactaat tcactcgaca gggaagatct tcgggtcttc ctttttcttc   11040
gaaatttttt aagagagaaa aaatgaaag catttaacaa aaaaattatg tttggtgtat   11100
tcagcggtct tgtgatgtca ttgagccatg ctgctgaagt cgaaagtgca aatacgcaag   11160
aaatccattt tcctgaaatc aaagacagct atttaaaaca agtgaaccgt tatgaatatg   11220
acgatgtcgc acgtttagac aagggattaa ccaaagatca gattcgccat attttgggaa   11280
atcctcaatt ctctgaaggt cttttttgcgg ttaagacatg gaattatgta ttggatattc   11340
```

```
gtgagcctaa ctcaaaccaa tataagcgtt gccaattacg catagatttt gataagcaat      11400
accgttcaga caatctatat tggaaaggtg aacaatgcca aggcttaatg gcttggggga      11460
ttaataatca gtctgagact gagcaaacga ctctagcacc tggtgggcag tctgcaagtg      11520
ttttgtttta ttttgatcat gcggataaaa atggtgtaaa gaacgctgaa gtgattcgta      11580
aaatcgcaga tcagattaaa caatctgatg cgaatagccc tgttttgtg gctggatata       11640 ctgatcgttt aggatcattt cagtataacc aacgtttatc tgcccaaaga gcgaatacag      11700
tcgttgaact cttgaagcaa caaggcattc gtggcgagca aattcagtac agtgctgaaa      11760
ataaaacaga tgtgtaccaa aagtgcgcag ggatcaataa aaagatccaa ctggttgaat      11820
gtctagcacc taaccgtcgt gtgaatatca cgtggtaa                              11858

<210> SEQ ID NO 6
<211> LENGTH: 68
<212> TYPE: DNA
<213> ORGANISM: Acinetobacter sp. Tol5

<400> SEQUENCE: 6
aagcttatga tgatacaaat ggtcgtttag ctgctgcttt aggtacaggt agtggtgctg      60
cctataat                                                              68

<210> SEQ ID NO 7
<211> LENGTH: 4907
<212> TYPE: DNA
<213> ORGANISM: Acinetobacter sp. Tol5

<400> SEQUENCE: 7
aacgcaagtt gttttactgc tgaagctgtc aattttgtc cacgacctga cttacggtcc       60
ggttgagtat acacagcgac gatttcgtgg tcagtttgaa tcagtgctgc taatgctgaa      120
gctgcaaatt cgggtgtgcc tgcaaaaatg atcttcaaag gttgtgctca gattaaattt      180
taaagtcaat tatagcaaac atggttctat ggtgggattt tcaaatgaaa atttgatttt      240
ctccaaatgt gaaaattaat tatattattt tgacacaaag ctatttattt atgattttga     300
cgtatctata gatctgatat gtttctttg attaatgaat ttgatgatat tttgatcgca      360
gtatgggtga tattaaaaaa taatgtgatt taaatcacat ttaatagact atgttttata     420
aaaattagaa tcattttca gagtatggtt tcttacatat tgaaataatg atctgttttt      480
ttgtgttttg taagtttttt ctaaacaaaa ttaataaata ttactcagaa aaacacaaag     540
tagtgaaaga taaaaataaa aagctattaa gaaaaattgt aaacacaaag aatgtaaact     600
taataaaata taattttgag gaatgagtca cacttatttt taacaaatgt gacaaaattt     660
gtcacatata taattagaaa taatgtgatt ttagtaaaac tttacaatac tgaggataaa     720
tataactcta tgtttttaa atgtaaaata ttaaaaatgt aaaataatat agcttaattt      780 caaaaaatt aaaccaattg gttaaaagt taaaaaagt gaaatatatc tcatttttt         840 gattgcttta attgtatgta aattgttaaa taaaaaaat tgtacatttt atatgcattg     900
ctaaagcaga acctactgcc caaaatgcat ctcctaagga aaagcgatat gaataaaatc     960
tacaaagtga tttggaatgc gactttgttg gcatgggttg cagtatctga attggcaaaa      1020
ggaaaaccaa atctacgac atcaaaatcc aaagctaaat cattatcttc atctgtaata       1080
gttggtggga taatattaac aacaccttta tctttaatag cagctactgt tcaagttgga      1140 ggggaacta attctggaac aactgctaca gcttctacga attgtgcaga cttatataat      1200
tatcaaaatc ctgagaactc aggctctgga gcggctggga attataatgc aggaaatcca      1260
```

```
agtgtgtgtt cgatcgctat aggtgaaaac gcacaaggtg gtacttctgg aactggaggg    1320
tcgccaggga tagcgatagg tggaaattct aaagctacgg gtggtttatc tgttgctata    1380
ggcggatatg ctcaagcgac aaatgttgga agtattgctt taggcacagc agctttatca    1440
agtggtttta acagtttagc aatatccaga caagctgctg caacgaataa ctattcaata    1500
gctataggta caacttcagt ttcgaaagga gttggatcga ttgctatggg gcattcaacg    1560
aatgcttctg gagatcaatc gatagcaatt ggtagctcgg atgctgttaa ttcagcaaca    1620
gcaacaacaa catacgatgg tacaacaaat actcaagcat caggtagtaa atcgattgct    1680
ataggtgcaa gcgcaaaggc atcaaccaat aacagcattg cactaggtgc aggatcggta    1740
acttctgcac aatctggtaa ttcttatctt actggtgtag gtgcatcagc tacaaatggt    1800
gttgtatctg ttggaacttc aactgcaaca cgtcgtatcc aaaatgtagc agatggttca    1860
gccgcttcag atgctgtgac agttgctcag ttggataaag cttatgatga tacaaatggt    1920
cgtttagctg ctgctttagg tacaggtagt ggtgctgcct ataatgcagc aaacaataca    1980
tataccgctc caacgaatat tgggggaaca ggtaaaaata cgattgatga tgcaattaaa    2040
gcaactcaac gaagtgtagt cgctggatca aatattgtcg ttaccccgac gacagcttct    2100
gatggttcaa tatcgtattc ggttgctaca agcgcaacac cgacgtttac aagtataact    2160
gtaaacaatg caccaacggc aggtacagat gcgaccaaca agacttatgt agactcaaaa    2220
gcagcagcat cgagaacaga agtagcagct ggaagcaatg tatctggtgt agtaaaaacg    2280
acaggcgcaa acggtcaaga cgtttataca gtaaatgcca atggtacgac tgcatcagca    2340
ggttcttcag cagttaccgt aacaccaggc acgaaagatg caaataatgt cactgactat    2400
aaagtagact tatcagcgac tacaaaaacc gatatccaaa aggtgtagat gcaaaaaat    2460 gctgtagata ccgcaggtct aaaatttaaa ggtgatacag caaccacaag caataccaag    2520
aaattaggtg acaccgtttc gattacgggt gatacgaaca ttagtacagt tgcgacaaca    2580
gatggtgtac aggttaagtt aaatccaaac ttggatttag gagcaactgg tagcgttaaa    2640
acgggtaata ccacgattaa caatgcaggt gtaacagctg atcaagttac ggttggtggt    2700
gttgttatta acaacacatc aggtattaat gctggtggta aagcgattac taatgtagca    2760
gcaccaacaa ataacacaga tgctgctaac aagaagtatg tagatgatgc aggtacagca    2820
ttaaccaatt tgggctttgg attaaaagca caagatggta cgactgtgaa caagaaatta    2880
ggtgaagcag ttgatattgt tggttcaaac agcaacatca gtacaaaagt aaatgcaggc    2940
aaagtagaag ttgcactatc caatacattg gacttaggta ctacaggtag cgttactacg    3000
ggttcaactg taattaacaa tactggtgtt acggcaactc aggttaccgc aaacaaagtc    3060
acaataaaca atgcaccaac agcaggtaca gatgcgacca caagactta tgtagactca    3120 aaagcagcag catcaagaac agaagtcgca gctggaagca atgtatctgg tgtagtaaaa    3180
acgacaggcg caaacggtca agatatttat gcagtaaatg ccaatggtac gactgcatca    3240
gcaggttctt cagcagttac cgtaacacca ggcacgaaag atgcaaataa tgtcactgac    3300
tataaagtag acttgtcagc gactacaaaa accgatattc aaaaggtgt agatgcaaaa    3360 aatgctgtag atactgcagg tctaaaattt aaaggtgata cagcaaccac aagcaatacc    3420
aagaaattag gtgacaccgt ttcgattacg ggtgatacga acattagtac agttgcaaca    3480
actgatggtg tacaggttaa gttaaatcca aacttagatt taggagcaac tggtagcgtt    3540
aaaacgggta ataccacgat taacaatgca ggtgtaacag ctgaccaagt tacgguttggt    3600 ggtgttgtta ttaacaacac atcaggtatt aatgctggtg gtaaagcgat taccaatgta    3660
```

| | | | | |
|---|---|---|---|---|
| gcagcaccaa | caaataacac | agatgctgct | aacaagaagt | atgtagatga cgcaggtaca | 3720 |
| gcattaacca | atttgggctt | tggattaaaa | gcgcaagatg | gtacgactgt gaacaagaaa | 3780 |
| ttaggtgaag | cagttgatat | tgttggttca | aacagcaaca | tcagtacaaa agtaaatgca | 3840 |
| ggcaaagtag | aagttgcact | atccaataca | ttggacttag | gtactacagg tagcgttact | 3900 |
| acgggttcaa | ctgtaattaa | caatgctggt | gttacggcaa | ctcaagttac cgcaaacaaa | 3960 |
| gtcacagtta | ataatgcacc | aacagcaggt | acagatgcga | ccaataaaac ttatgtagac | 4020 |
| tcaaaagcag | cggcatcaag | aacagaagtc | gcagctggaa | gcaatgtatc tggcgtagta | 4080 |
| aaaacgacag | gtgcaaacgg | tcaagacgtt | tatacagtaa | atgccaatgg tacgactgca | 4140 |
| tcagcaggtt | cttcagcagt | taccgtaaca | ccaggcacga | aagatgcaaa taatgtcact | 4200 |
| gactataaag | tagacttgtc | agcgactaca | aaaaccgata | ttcaaaaagg tgtagatgca | 4260 |
| aaaaatgctg | tagataccgc | aggtctaaaa | tttaaaggtg | atacagcaac cacaagcaat | 4320 |
| accaagaaat | taggtgacac | cgtttcgatt | acgggtgata | cgaacattag tacagttgcg | 4380 |
| acaactgatg | gtgtacaggt | taagctaaat | ccaaacttgg | atttaggagc aactggtagc | 4440 |
| gttaaaacgg | gtaataccac | gattaacaat | gcaggtgtaa | cagctgatca agttacagtt | 4500 |
| ggtggtgttg | ttattaacaa | cacatcaggt | attaatgctg | gtggtaaagc gattaccaat | 4560 |
| gtagcagcac | caacaaataa | cacagatgct | gctaacaaga | agtatgtaga tgatgcaggt | 4620 |
| acagcattaa | ccaatttggg | ctttggatta | aaagcgcaag | atggtacgac tgtgaacaag | 4680 |
| aaattaggcg | aagcagttga | agttgttggt | gcggacagta | acatcaccac gaaagttgca | 4740 |
| ggcggtcagg | ttgcaattga | gttaaataaa | aacctcaaca | acttaactgg cattaccgtg | 4800 |
| aacgatggaa | ccaatggcac | caatggttca | actgtgattg | gtaaagatgg tatttcggtt | 4860 |
| aaagatggtt | caggcaatac | cattgcaggt | gtagataaca | cagcgtt | 4907 |

<210> SEQ ID NO 8
<211> LENGTH: 2280
<212> TYPE: DNA
<213> ORGANISM: Acinetobacter sp. Tol5

<400> SEQUENCE: 8

| | | | | |
|---|---|---|---|---|
| caggtctaaa | atttaaaggt | gatacagcaa | ccacaagcaa | taccaagaaa ttaggtgaca | 60 |
| ccgtttcgat | tacgggtgat | acgaacatta | gtacagttgc | aacaactgat ggtgtacagg | 120 |
| ttaagttaaa | tccaaactta | gatttaggag | caactggtag | cgttaaaacg ggtaatacca | 180 |
| cgattaacaa | tgcaggtgta | acagctgacc | aagttacggt | tggtggtgtt gttattaaca | 240 |
| acacatcagg | tattaatgct | ggtggtaaag | cgattaccaa | tgtagcagca ccaacaaata | 300 |
| acacagatgc | tgctaacaag | aagtatgtag | atgacgcagg | tacagcatta accaatttgg | 360 |
| gctttggatt | aaaagcgcaa | gatggtacga | ctgtgaacaa | gaaattaggt gaagcagttg | 420 |
| atattgttgg | ttcaaacagc | aacatcagta | caaaagtaaa | tgcaggcaaa gtagaagttg | 480 |
| cactatccaa | tacattggac | ttaggtacta | caggtagcgt | tactacgggt tcaactgtaa | 540 |
| ttaacaatgc | tggtgttacg | gcaactcaag | ttaccgcaaa | caaagtcaca gttaataatg | 600 |
| caccaacagc | aggtacagat | gcgaccaata | aaacttatgt | agactcaaaa gcagcggcat | 660 |
| caagaacaga | agtcgcagct | ggaagcaatg | tatctggcgt | agtaaaaacg acaggtgcaa | 720 |
| acggtcaaga | cgtttataca | gtaaatgcca | atggtacgac | tgcatcagca ggttcttcag | 780 |
| cagttaccgt | aacaccaggc | acgaaagatg | caaataatgt | cactgactat aaagtagact | 840 |
| tgtcagcgac | tacaaaaacc | gatattcaaa | aaggtgtaga | tgcaaaaaat gctgtagata | 900 |

| | | | | |
|---|---|---|---|---|
| ccgcaggtct | aaaatttaaa | ggtgatacag | caaccacaag | caataccaag aaattaggtg | 960 |
| acaccgtttc | gattacgggt | gatacgaaca | ttagtacagt | tgcgacaact gatggtgtac | 1020 |
| aggttaagct | aaatccaaac | ttggatttag | gagcaactgg | tagcgttaaa acgggtaata | 1080 |
| ccacgattaa | caatgcaggt | gtaacagctg | atcaagttac | agttggtggt gttgttatta | 1140 |
| acaacacatc | aggtattaat | gctggtggta | aagcgattac | caatgtagca gcaccaacaa | 1200 |
| ataacacaga | tgctgctaac | aagaagtatg | tagatgatgc | aggtacagca ttaaccaatt | 1260 |
| tgggctttgg | attaaaagcg | caagatggta | cgactgtgaa | caagaaatta ggcgaagcag | 1320 |
| ttgaagttgt | tggtgcggac | agtaacatca | ccacgaaagt | tgcaggcggt caggttgcaa | 1380 |
| ttgagttaaa | taaaaacctc | aacaacttaa | ctggcattac | cgtgaacgat ggaaccaatg | 1440 |
| gcaccaatgg | ttcaactgtg | attggtaaag | atggtatttc | ggttaaagat ggttcaggca | 1500 |
| ataccattgc | aggtgtagat | aacacagcgt | tgacagttaa | agatggcagt ggcaacacag | 1560 |
| aaaccagcat | taaccaagcg | atcaacacgt | taaatgcagc | gcaaggtgaa actgataagt | 1620 |
| ttgcagtgaa | gtacgacaaa | aatgctgatg | gcagtgtgaa | ctacaacaac atcacattgg | 1680 |
| caggtacgac | tgcaagcagt | acacaagatg | caactacagg | caagatcacc acaacaggtg | 1740 |
| gaacaagctt | gaacaatgtt | gcaagtgcgg | gtgactacaa | agatgttgcc aatgcaagca | 1800 |
| aaggtgtaaa | cgcaggtgac | ttaaacaatg | cagttgttga | tgcaaccaat gcagcaacca | 1860 |
| gcaaaggctt | tgcattacaa | gcagcagatg | gcgctaaagt | tcagaagaac ctaggcgaag | 1920 |
| cagttgaagt | tgtcggtgcc | gacagcaaca | tcaccacaaa | agttgcaggc ggtcaggttg | 1980 |
| caattgagtt | aaataaaaac | ctcaacaact | taactggcat | taccgtgaac gatggaacca | 2040 |
| atggcaccaa | tggttcaact | gtgattggta | aagatggtat | ttcagttaaa gacggttcag | 2100 |
| gcaataccat | tgcaggtgta | gataacacag | cgttgacagt | taaagatggc agtggcaaca | 2160 |
| cagaaaccag | cattaaccaa | gcgatcaaca | cgttaaatgc | agcgcaaggt gaaactgata | 2220 |
| agtttgcagt | gaagtacgac | aaaaatacgg | atggtagtac | caactacaac agtattactg | 2280 |

<210> SEQ ID NO 9
<211> LENGTH: 2540
<212> TYPE: DNA
<213> ORGANISM: Acinetobacter sp. Tol5

<400> SEQUENCE: 9

| | | | | |
|---|---|---|---|---|
| cttgaacaat | gttgcaagtg | cgggtgacta | caaagatgtt | gccaatgcaa gcaaaggtgt | 60 |
| aaacgcaggt | gacttgaaca | atgcagttgt | tgatgcaacc | aatgcagcga ccagcaaagg | 120 |
| ctttgcatta | caagcagcag | atggcgctaa | agttcagaag | aacctaggcg aagcagttga | 180 |
| agttgttggt | gcggacagta | acatcaccac | gaaagttgca | ggcggtcagg ttgcaattga | 240 |
| gttaaataaa | aacctcaaca | acttaactgg | cattaccgtg | aacgatggaa ccaatggcac | 300 |
| caatggttca | actgtgattg | gtaaagatgg | tatttcggtt | aaagatggtt caggcaatac | 360 |
| cattgcaggt | gtagataaca | cagcgttgac | agttaaagat | ggcagtggca acacagaaac | 420 |
| cagcattaac | caagcgatca | cacgttaaa | tgcagcgcaa | ggtgaaactg ataagtttgc | 480 |
| agtgaagtac | gacaaaaatg | ctgatggcag | tgcaaactat | aacaatgtca ctttagctgg | 540 |
| tacaaatggc | acaataatca | gcaatgttaa | agcgggtgct | gtgacctcaa catctactga | 600 |
| tgcgatcaat | ggtagccaat | tatatggtgt | tgcaaacagc | gtgaagaatg caattggtgg | 660 |
| ttcaaccaca | attgatgcaa | cgactggtgc | aatcacgacg | accaatattg gtggtacagg | 720 |
| ttcaaatacg | attgatggtg | caatcagcag | tattaaagat | tcagcgacta aagcgaaaac | 780 |

-continued

```
cacggtaagt gctggggata atgttgtcgt tacatcgggt accaatgcag atggctcaac    840
aaactatgaa gttgcgacag cgaaagacgt taactttgac aaagtgactg taggtagtgt    900
tgttgtagat aaatcaagca atacaatcaa aggattaagt aataccactt ggaacggaac    960
agcagtatca ggtcaagcgg cgacagaaga ccagttaaaa acggtcagcg atgcgcaagg   1020
tgaaactgat aagtttgcag tgaagtacga caaaaatgct gatggcagtg cgaactacaa   1080
cagtattact gcaggcaatg gtaacggtac tgcagcaacg atcggaactg acacagcagg   1140
taatagtgtt gtgaccagtg gcggaactaa aattagtaat gttgcgaatg gtgtcaatgc   1200
aagtgatgca gtaaacaaag gtcaattgga tagcttaagt acaggtctta ccaatacagg   1260
ctttggttta aaagcagcag atggcaacac cgttaacaaa aaattaggcg aagcagtaga   1320
cgttgtcggt gctgacagca acatcaccac gaaagttgca ggcggtcagg ttgcgattga   1380
gttaaataaa aacctcaaca acttaactgg cattaccgtg aacgatggaa ccaatggcac   1440
caatggttca actgtgattg gtaaagatgg tatttcgatt aaagatggtt caggcaatac   1500
cattgcaggt gtagataaca cagcgttgac ggttaaagat agcagtggca cacagaaac    1560 cagcattaac caagcgatca acacgttaaa tgcagcgcaa ggtgaaactg ataagtttgc   1620
agtgaagtac gataagaatg ctgatggcag tgtgaactat aacaatgtca ctttagcagg   1680
tacaaatggc acaataatca gaaatgttaa agcgggtgct gtgacctcaa catctactga   1740
tgcgatcaat ggtagccaat tatacgatat tgcaaacagc gtgaagaatg caattggtgg   1800
ttcaaccaca agagatgtaa cgactggtgc aatcacaacg accaatattg gtggtacagg   1860
ttcaaacacg attgatggtg caatcagcag tattaaagat tcagcgacta aagcgaaaac   1920
cacgataagt gctggggata atgttgtcgt tacatcgggt accaatgcag atggctcaac   1980
aaactatgaa gttgcgacag cgaaagacgt taactttgac aaagtaactg taggtaatgt   2040
tgttgttgat aaggcaaatg acacgatcca aggtttgagc aataaagatc taaattcaac   2100
tgattttgcg accaaaggta gagctgcgac tgaagaacag ttaaaagcag tgattaccag   2160
taatatcacg gaagttgtgg atggtaatgg caacaaggtg aatattattg accaagttgt   2220
aaataccaaa cctgacaata gaaccaaga ttcattgttc ttaacgtatg acaaacaagg    2280
tcaagaaacc acagatcgcc taacgattgg tcaaacggta cagaagatga atactgatgg   2340
tattaaattc ttccatacca atgccgtata atcaaaggt gatttgggta caacaaatga    2400
ctcaagtgca ggtggtttaa actctacagc aattggtgta atgcgattg ttgcgaatgg    2460 tgcagatagt tcagttgctt taggtcataa caccaaagtc aatggtaaac aatcaattgc   2520
aattggttct ggtgcagaag                                             2540
```

<210> SEQ ID NO 10
<211> LENGTH: 1185
<212> TYPE: DNA
<213> ORGANISM: Acinetobacter sp. To15

<400> SEQUENCE: 10

```
cttgaacaat gttgcaagtg cgggtgacta caaagatgtt gccaatgcaa gcaaaggtgt     60
aaacgcaggt gacttaaaca atgcagttgt tgatgcaacc aatgcagcaa ccagcaaagg   120
ctttgcatta caagcagcag atggcgctaa agttcagaag aacctaggcg aagcagttga   180
agttgtcggt gccgacagca acatcaccac aaaagttgca ggcggtcagg ttgcaattga   240
gttaaataaa aacctcaaca acttaactgg cattaccgtg aacgatggaa ccaatggcac   300
caatggttca actgtgattg gtaaagatgg tatttcagtt aaagacggtt caggcaatac   360
```

| | | |
|---|---|---|
| cattgcaggt gtagataaca cagcgttgac agttaaagat ggcagtggca acacagaaac | 420 |
| cagcattaac caagcgatca acacgttaaa tgcagcgcaa ggtgaaactg ataagtttgc | 480 |
| agtgaagtac gacaaaaata cggatggtag taccaactac aacagtatta ctgcaggcaa | 540 |
| tggtaacggt actgcagcaa cgatcggaac tgacacagca ggtaatagtg ttgtgaccag | 600 |
| tggcggaact aaaattagta atgttgcgaa tggtgtcaat gcaagtgatg cagtaaacaa | 660 |
| aggtcaattg gatagcttaa gtacaggtct taccaataca ggctttggtt taaaagcagc | 720 |
| agatggcaac accgttaaca aaaaattagg cgaagcagta gacgttgtcg gtgctgacag | 780 |
| caacatcacc acgaaagttg caggcggtca ggttgcgatt gagttaaaata aaaacctcaa | 840 |
| caacttaact ggcattaccg tgaacgatgg aaccaatggc accaatggtt caactgtgat | 900 |
| tggtaaagat ggtatttcga ttaaagatgg ttcaggcaat accattgcag gtgtagataa | 960 |
| cacagcgttg acagttaaag atggcagtgg caacacagaa accagcatta accaagcgat | 1020 |
| caacacgtta atgcagcgc aaggtgaaac tgacaagttt gcagtgaagt acgacaagaa | 1080 |
| tgctgatggc agtgcaaact acaacaacat cacattggca ggtacgactg caagtagcac | 1140 |
| gcaagatgca acaacaggca agatcaccac aacaggtgga acaag | 1185 |

<210> SEQ ID NO 11
<211> LENGTH: 603
<212> TYPE: DNA
<213> ORGANISM: Acinetobacter sp. Tol5

<400> SEQUENCE: 11

| | | |
|---|---|---|
| cttgaacaat gttgcaagtg cgggtgacta caaagatgtt gccaatgcaa gcaaaggtgt | 60 |
| aaacgcaggt gacttaaaca atgcagttgt tgatgcaacc aatgcagcaa ccagcaaagg | 120 |
| ctttgcatta caagcagcag atggcgctaa agttcagaag aacctaggcg aagcagttga | 180 |
| agttgtcggt gccgacagca acatcaccac aaaagttgca ggcggtcagg ttgcaattga | 240 |
| gttaaataaa aacctcaaca acttaactgg cattaccgtg aacgatggaa ccaatggcac | 300 |
| caatggttca actgtgattg gtaaagatgg tatttcagtt aaagacggtt caggcaatac | 360 |
| cattgcaggt gtagataaca cagcgttgac agttaaagat ggcagtggca acacagaaac | 420 |
| cagcattaac caagcgatca acacgttaaa tgcagcgcaa ggtgaaactg ataagtttgc | 480 |
| agtgaagtac gacaaaaatg ctgatggcag tgtgaactac aacaacatca cattggcagg | 540 |
| tacgactgca agcagtacac aagatgcaac tacaggcaag atcaccacaa caggtggtac | 600 |
| aag | 603 |

<210> SEQ ID NO 12
<211> LENGTH: 2928
<212> TYPE: DNA
<213> ORGANISM: Acinetobacter sp. Tol5

<400> SEQUENCE: 12

| | | |
|---|---|---|
| cagcaacgat cggaactgac acagcaggta atagtgttgt gaccagtggc ggaactaaaa | 60 |
| ttagtaatgt tgcgaatggt gtcaatgcaa gtgatgcagt aaacaaaggt caattggata | 120 |
| gcttaagtac aggtcttacc aatacaggct ttggtttaaa agcagcagat ggcaacaccg | 180 |
| ttaacaaaaa attaggcgaa gcagtagacg ttgtcggtgc tgacagcaac atcaccacga | 240 |
| aagttgcagg cggtcaggtt gcgattgagt taaataaaaa cctcaacaac ttaactggca | 300 |
| ttaccgtgaa cgatggaacc aatggcacca atggttcaac tgtgattggt aaagatggta | 360 |
| tttcgattaa agatggttca ggcaatacca ttgcaggtgt agataacaca gcgttgacag | 420 |

```
ttaaagatgg cagtggcaac acagaaacca gcattaacca agcgatcaac acgttaaatg    480
cagcgcaagg tgaaactgac aagtttgcag tgaagtacga caagaatgct gatggcagtg    540
caaactacaa caacatcaca ttggcaggta cgactgcaag tagcacgcaa gatgcaacaa    600
caggcaagat caccacaaca ggtggaacaa gcttgaacaa cgttgcaagt gcaggtgact    660
acaaagatgt tgccaatgca agcaaaggtg taaacgcagg tgacttgaac aatgcagttg    720
ttgatgcaac caatgcagca accagcaaag gctttgcatt acaagcagca gatggcgcta    780
aagttcagaa gaacctaggc gaagcagttg aagttgtcgg tgcggacagc aacatcacca    840
caaaagtagt gggtggacaa gttgcgattg agttaaataa aaacctcaac aacttaactg    900
gcattaccgt gaacgatgga accaatggca caaatggttc aactgtgatt ggtaaagatg    960
gtatttcggt taaagatggt tcaggtaata ccattgcagg tgtagataac acagcgttga   1020
cagttaaaga tggcagtggc aacacagaaa ccagcattaa ccaagcgatc aacacgttaa   1080
atgcagcgca aggtgaaact gataagtttg cagtgaagta cgacaaaaat gctgatggca   1140
gtgtgaacta caacaacatc acattggcag gtacgactgc aagcagtaca caagatgcaa   1200
ctacaggcaa gatcaccaca acaggtggaa caagcttgaa caatgttgca agtgcgggtg   1260
actacaaaga tgttgccaat gcaagcaaag gtgtaaacgc aggtgactta aacaatgcag   1320
ttgttgatgc aaccaatgca gcaaccagca aaggcttcgc attacaagca gcagatggcg   1380
ctaaagttca gaagaaccta ggcgaagcag ttgaagttgt cggtgccgac agcaacatca   1440
ccacaaaagt tgcaggcggt caggttgcaa ttgagttaaa taaaaacctc aacaacttaa   1500
ctggcattac cgtgaacgat ggaaccaatg gcaccaatgg ttcaactgtg attggtaaag   1560
atggtatttc agttaaagac ggttcaggca ataccattgc aggtgtagat aacacagcgt   1620
tgacagttaa agatggcagt ggcaacacag aaaccagcat taaccaagcg atcaacacgt   1680
taaatgcagc gcaaggtgaa actgataagt ttgcagtgaa gtacgacaaa aatgctgatg   1740
gcagtgtgaa ctacaacaac atcacattgg caggtacgac tgcaagcagt acacaagatg   1800
caactacagg caagatcacc acaacaggtg gtacaagctt gaacaatgtt gcaagtgcgg   1860
gtgactacaa agatgttgcc aatgcaagca aggtgtaaaa cgcaggtgac ttgaacaatg   1920
cagttgttga tgcaaccaat gcagcgacca gcaaaggctt tgcattacaa gcagcagatg   1980
gcgctaaagt tcagaagaac ctaggcgaag cagttgaagt tgttggtgcg acagtaacaa   2040
tcaccacgaa agttgcaggc ggtcaggttg caattgagtt aaataaaaac ctcaacaact   2100
taactggcat taccgtgaac gatggaacca atggcaccaa tggttcaact gtgattggta   2160
agatggtatt tcggttaaaa gatggttcag gcaataccat tgcaggtgta gataacacag   2220
cgttgacagt taaagatggc agtggcaaca cagaaaccag cattaaccaa gcgatcaaca   2280
cgttaaatgc agcgcaaggt gaaactgata gtttgcagt gaagtacgac aaaaatgctg   2340
atggcagtga aaactataac aatgtcactt tagctggtac aaatggcaca ataatcagca   2400
atgttaaagc gggtgctgtg acctcaacat ctactgatgc gatcaatggt agccaattat   2460
atggtgttgc aaacagcgtg aagaatgcaa ttggtggttc aaccacaatt gatgcaacga   2520
ctggtgcaat cacgacgacc aatattggtg gtacaggttc aaatacgatt gatggtgcaa   2580
tcagcagtat taaagattca gcgactaaag cgaaaaccac ggtaagtgct ggggataatg   2640
ttgtcgttac atcgggtacc aatgcagatg gctcaacaaa ctatgaagtt gcgacagcga   2700
aagacgttaa ctttgacaaa gtgactgtag gtagtgttgt tgtagataaa tcaagcaata   2760
caatcaaagg attaagtaat accacttgga acggaacagc agtatcaggt caagcggcga   2820
```

```
cagaagacca gttaaaaacg gtcagcgatg cgcaaggtga aactgataag tttgcagtga   2880
agtacgacaa aaatgctgat ggcagtgcga actacaacag tattactg              2928

<210> SEQ ID NO 13
<211> LENGTH: 3120
<212> TYPE: DNA
<213> ORGANISM: Acinetobacter sp. To15

<400> SEQUENCE: 13
cagcaacgat cggaactgac acagcaggta atagtgttgt gaccagtggc ggaactaaaa     60
ttagtaatgt tgcgaatggt gtcaatgcaa gtgatgcagt aaacaaaggt caattggata    120
gcttaagtac aggtcttacc aatacaggct ttggtttaaa agcagcagat ggcaacaccg    180
ttaacaaaaa attaggcgaa gcagtagacg ttgtcggtgc tgacagcaac atcaccacga    240
aagttgcagg cggtcaggtt gcgattgagt taaataaaaa cctcaacaac ttaactggca    300
ttaccgtgaa cgatggaacc aatggcacca atggttcaac tgtgattggt aaagatggta    360
tttcgattaa agatggttca ggcaatacca ttgcaggtgt agataacaca gcgttgacgg    420
ttaaagatag cagtggcaac acagaaacca gcattaacca agcgatcaac acgttaaatg    480
cagcgcaagg tgaaactgat aagtttgcag tgaagtacga taagaatgct gatggcagtg    540
tgaactataa caatgtcact ttagcaggta caaatggcac aataatcaga atgttaaag    600 cgggtgctgt gacctcaaca tctactgatg cgatcaatgg tagccaatta tacgatattg    660
caaacagcgt gaagaatgca attggtggtt caaccacaag agatgtaacg actggtgcaa    720
tcacaacgac caatattggt ggtacaggtt caaacacgat tgatggtgca atcagcagta    780
ttaaagattc agcgactaaa gcgaaaacca cgataagtgc tggggataat gttgtcgtta    840
catcgggtac caatgcagat ggctcaacaa actatgaagt tgcgacagcg aaagacgtta    900
actttgacaa agtaactgta ggtaatgttg ttgttgataa ggcaaatgac acgatccaag    960
gtttgagcaa taaagatcta aattcaactg attttgcgac caaaggtaga gctgcgactg   1020
aagaacagtt aaaagcagtg attaccagta atatcacgga agttgtggat ggtaatggca   1080
acaaggtgaa tattattgac caagttgtaa ataccaaacc tgacaataag aaccaagatt   1140
cattgttctt aacgtatgac aaacaaggtc aagaaaccac agatcgccta acgattggtc   1200
aaacggtaca gaagatgaat actgatggta ttaaattctt ccataccaat gccgatacat   1260
caaaaggtga tttgggtaca acaaatgact caagtgcagg tggtttaaac tctacagcaa   1320
ttggtgtaaa tgcgattgtt gcgaatggtg cagatagttc agttgcttta ggtcataaca   1380
ccaaagtcaa tggtaaacaa tcaattgcaa ttggttctgg tgcagaagct ttaggcaatc   1440
aatcgatcag tattggtaca ggcaataaag tcactggtga tcattcgggt gcgattggtg   1500
atccaactat tgtaaatggt gcaaacagct actctgtggg taataacaac caagtactta   1560
cagatgacac tttcgtactt ggaaacaatg tcaccaaaac tattgctggt tcagtagtat   1620
tgggtaacgg ttcagctgca acgacaggtg ctggtgaggc aggctatgcc ttatctgtag   1680
caacaaatgc agataaagcc gcgatcacta aaactcgtc aagcactggt gctgttgcag   1740
ttggtgatgc gtcgagcggt atttatcgtc aaattaccgg tgttgctgcg ggtagcgtag   1800
attcagatgc tgtgaacgtt gcacagttaa agcggtggg taaccaagtt gtaacgactc   1860
aaactacatt ggtgaacagt ttgggtggta acgctaaagt aaatgcagac ggtacgatta   1920
caggaccaac ttataatgtt gctcaaggta atcagaccaa tgttggtgat gcattaactg   1980
cgcttgataa cgcaattaat actgcggcaa caacatctaa atcgactgtt tctaatggtc   2040
```

```
agaatattgt tgtcagcaag agcaaaaatg cagatggttc agacaactat gaagtatcaa    2100
cagcaaaaga cttgacagtt gattctgtca aagcgggtga tacggttctg aataatgcag    2160
gtattacaat tggcaataac gcagttgtat tgaacaacac tggattaacc attagtggtg    2220
gaccaagtgt taccttggca ggcatcgatg caggcaataa aaccattcaa aatgttgcga    2280
atgcagtaaa tgcaacagat gcagtcaaca aagggcaatt ggacagcgca attaacaatg    2340
tgaataacaa tgtaaatgag cttgccaaca acgctgttaa atatgacgat gcatcaaaag    2400
ataagatcac acttggtggt ggggcaactg gtacaacaat caccaatgtg aaagatggta    2460
ctgttgcgca aggttctaaa gatgctgtga atggcggtca attgtggaat gttcaacaac    2520
aagttgatca gaacacaact gatattagca atatcaaaaa tgatattaac aacggtactg    2580
ttggtttggt tcaacaagca ggtaaagatg caccagtgac ggttgcaaaa gatactggcg    2640
gtacaacggt gaatgtcgct ggaacagatg gcaaccgagt agtgacaggt gttaaggaag    2700
gtgcagtgaa tgcaacatct aaagatgctg tcaatggtag tcaattgaat acaaccaacc    2760
aagcggtagt caattatctt ggtggtgggg caggttatga caacattaca ggtagcttca    2820
cagcgccaag ttatacggta ggtgactcga aatacaacaa tgttggtggc gcaattgatg    2880
cattgaatca agcagatcaa gcattgaata gcaaaattga caatgtcagt aacaagttgg    2940
ataacgcatt ccgtattacc aacaaccgta ttgatgatga agagaaaaaa gccaatgctg    3000
gtattgccgc tgcgatggct ctggaatcag caccatatgt cccaggtaaa tatacctatg    3060
cagcaggcgc agcttaccac ggtggtgaaa atgcggtagg tgtgactttt cgtaaaactg    3120
```

<210> SEQ ID NO 14
<211> LENGTH: 4951
<212> TYPE: DNA
<213> ORGANISM: Acinetobacter sp. Tol5
<220> FEATURE:
<221> NAME/KEY: misc_feature
<222> LOCATION: (3231)..(3231)
<223> OTHER INFORMATION: n is a, c, g, or t
<220> FEATURE:
<221> NAME/KEY: misc_feature
<222> LOCATION: (3247)..(3247)
<223> OTHER INFORMATION: n is a, c, g, or t
<220> FEATURE:
<221> NAME/KEY: misc_feature
<222> LOCATION: (4106)..(4106)
<223> OTHER INFORMATION: n is a, c, g, or t

<400> SEQUENCE: 14

```
ctttaggcaa tcaatcgatc agtattggta caggcaataa agtcactggt gatcattcgg      60
gtgcgattgg tgatccaact attgtaaatg gtgcaaacag ctactctgtg ggtaataaca     120
accaagtact tacagatgac actttcgtac ttggaaacaa tgtcaccaaa actattgctg     180
gttcagtagt attgggtaac ggttcagctg caacgacagg tgctggtgag gcaggctatg     240
ccttatctgt agcaacaaat gcagataaag ccgcgatcac taaaactacg tcaagcactg     300
gtgctgttgc agttggtgat gcgtcgagcg gtatttatcg tcaaattacc ggtgttgctg     360
cgggtagcgt agattcagat gctgtgaacg ttgcacagtt aaaagcggtg ggtaaccaag     420
ttgtaacgac tcaaactaca ttggtgaaca gtttgggtgg taacgctaaa gtaaatgcag     480
acggtacgat tacaggacca acttataatg ttgctcaagg taatcagacc aatgttggtg     540
atgcattaac tgcgcttgat aacgcaatta atactgcggc aacaacatct aaatcgactg     600
tttctaatgg tcagaatatt gttgtcagca agagcaaaaa tgcagatggt tcagacaact     660
atgaagtatc aacagcaaaa gacttgacag ttgattctgt caaagcgggt gatacggttc     720
```

```
tgaataatgc aggtattaca attggcaata acgcagttgt attgaacaac actggattaa    780
ccattagtgg tggaccaagt gttaccttgg caggcatcga tgcaggcaat aaaaccattc    840
aaaatgttgc gaatgcagta aatgcaacag atgcagtcaa caaagggcaa ttggacagcg    900
caattaacaa tgtgaataac aatgtaaatg agcttgccaa caacgctgtt aaatatgacg    960
atgcatcaaa agataagatc acacttggtg gtggggcaac tggtacaaca atcaccaatg   1020
tgaaagatgg tactgttgcg caaggttcta agatgctgt gaatggcggt caattgtgga   1080
atgttcaaca acaagttgat cagaacacaa ctgatattag caatatcaaa atgatatta   1140
acaacggtac tgttggtttg gttcaacaag caggtaaaga tgcaccagtg acggttgcaa   1200
aagatactgg cggtacaacg gtgaatgtcg ctggaacaga tggcaaccga gtagtgacag   1260
gtgttaagga aggtgcagtg aatgcaacat ctaaagatgc tgtcaatggt agtcaattga   1320
atacaaccaa ccaagcggta gtcaattatc ttggtggtgg ggcaggttat gacaacatta   1380
caggtagctt cacagcgcca agttatacgg taggtgactc gaaatacaac aatgttggtg   1440
gcgcaattga tgcattgaat caagcagatc aagcattgaa tagcaaaatt gacaatgtca   1500
gtaacaagtt ggataacgca ttccgtatta ccaacaaccg tattgatgat gtagagaaaa   1560
aagccaatgc tggtattgcc gctgcgatgg ctctggaatc agcaccatat gtcccaggta   1620
aatataccta tgcagcaggc gcagcttacc acggtggtga aaatgcggta ggtgtgactt   1680
tacgtaaaac tgcagacaat ggtcgttggt cgattacagg cggtgtagct gcagcgtctc   1740
aaggcgatgc aagtgttcgt atcggtatca gcggtgtgat tgactaattc actcgacagg   1800
gaagatcttc gggtcttcct ttttcttcga aaatttttta agagagaaaa aatgaaagca   1860
tttaacaaaa aaattatgtt tggtgtattc agcggtcttg tgatgtcatt gagccatgct   1920
gctgaagtcg aaagtgcaaa tacgcaagaa atccattttc ctgaaatcaa agacagctat   1980
ttaaaacaag tgaaccgtta tgaatatgac gatgtcgcac gtttagacaa gggattaacc   2040
aaagatcaga ttcgccatat tttgggaaat cctcaattct ctgaaggtct ttttgcggtt   2100
aagacatgga attatgtatt ggatattcgt gagcctaact caaaccaata taagcgttgc   2160
caattacgca tagattttga taagcaatac cgttcagaca atctatattg gaaaggtgaa   2220
caatgccaag gcttaatggc ttgggggatt aataatcagt ctgagactga gcaaacgact   2280
ctagcacctg tgggcagtc tgcaagtgtt ttgttttatt ttgatcatgc ggataaaaat   2340
ggtgtaaaga acgctgaagt gattcgtaaa atcgcagatc agattaaaca atctgatgcg   2400
aatagccctg ttttttgtggc tggatatact gatcgtttag gatcatttca gtataaccaa   2460
cgtttatctg cccaaagagc gaatacagtc gttgaactct tgaagcaaca aggcattcgt   2520
ggcgagcaaa ttcagtacag tgctgaaaat aaaacagatg tgtaccaaaa gtgcgcaggg   2580
atcaataaaa agatccaact ggttgaatgt ctagcaccta accgtcgtgt gaatatcacg   2640
tggtaagtct tatttattca atctaatttt ggataatcca aacaaaaaac gatatgtgtt   2700
ccacattatc gttttttgtt ttttgagcag gtgttgatta aaaaatcaag gagctgatga   2760
gattgcaaaa atttccaatt aatttaaaac aataaagtac gcaatgatg aaaaaacagt    2820
tgtgttaatg attggcttgg ggtttacctt tctggcacaa gcatttgata aaaaagtaat   2880
gatatttcga ttatcaatat ttgagcttct atgaatagaa atcttttata aaattaaatt   2940
tagtgattat tgttaaatga taaatattat ttattaaaaa ataaaaaatt attcatagaa   3000
gttttgtgtc taatctggcg tgttagcgtt atattaaata tcaatattca tttatctcta   3060
aaccctgttg aaatataagt aaacacgtct tgtttaaaaa aagatcatac tcaaggtcat   3120
```

```
tggttctacg ttaacttata gtatgatgtg tacatatttc gactgattta ttgctatatc      3180
agttttattt agccagagtg aatctgattc atttcaagct caaacaatgt nggaaataca      3240
aatgccngac tatcgttcaa aaacatcgac acatggaaga aatatggctg gtgcacgtgg      3300
cttatggcgt gcaacaggaa tgaaagatga agatttcggt aagccgatta ttgcggtagt      3360
caactcattt acccagtttg tgcctggtca tgtccacctt aaagatttag gtcaactggt      3420
tgcggaacaa atccaagcag ctggtggtgt ggcaaaagaa tttaatacca ttgccgtgga      3480
tgatggtatc gcaatggggc atgatggcat gctgtattca ttgccttcac gtgatttgat      3540
tgcagactct gtcgaatata tggtcaatgc acactgcgca gatgccatgg tgtgtatttc      3600
aaactgtgac aaaattaccc cagggatgtt aatggcagcg atgcgcttaa acattccagt      3660
ggtgtttgtg tcgggtggac caatggaagc gggtaaagtt aaaatccgtg gtacagaacg      3720
tgcaattgac ttagttgatg cgatggtggt tgcagccgat gataatttta cagatgaaga      3780
agtaaaagaa tacgagcgtt cagcatgccc aacatgtggt tcatgttcag gtatgttcac      3840
agcaaattcg atgaactgtt tgacagaagc attggggttg tcgttaccag gaaatggttc      3900
aacattagca acgcatgcta accgtaagaa actattcgaa aaagcaggtc aattggttgt      3960
tgaattggca aaacgccatt atgaacaaga tgattacacg gtattaccac gttcgatcgc      4020
aaccaaagca tcttatgaaa atgccatgac gctcgatatt gcgatgggtg gttcaaccaa      4080
taccgtattg catttattgg ctgctnccag tgaagcaggt gttgacttta ccatggatga      4140
cattgatcgt ttatcgcgta aagtgcctgt attatgtaaa gttgctcctg caaagcagga      4200
tgtgcatatg gaagatgtgc atcgtgccgg tggcatcatg tccattctcg gtgaattgga      4260
tcgtgcaggt ttattagata catcggtaca cactgtgcat gagcacacct taaaagatgc      4320
attggataaa tgggatatta ttcgtacaga agacccagtg gtatatgagt tcttccgctc      4380
agcgccaggt ggtgttccaa ctcaaacagc attctcacaa aatcgctatt accagacttt      4440
ggatggcaat cgtgaaacag gtgtgattcg taatgctgaa catgctttct ctaaagatgg      4500
tggcttggca gtattgtatg caacattgc tgtagatggg tgtattgtta aaacagcagg      4560
tgttgatgat tcaattttaa aatttaatgg aactgcacga gtatttgaaa gccaagatgc      4620
tgcagtagat tcaattttag acatgaaat taaggctggt gatgtggttg tgatccgtta      4680
tgaaggacca cgtggtggac cgggtatgca ggaaatgctt tatccgacca gttatttaaa      4740
atcaaaaggc ttaggtaaag aatgtgcttt actgacagat ggacgtttct ctggaggttc      4800
ttctggcctt tcaattggtc atgtatcacc tgaagctgct gaaggtggtg tgattggatt      4860
ggttgaagat ggtgatttga ttgaaattga tattccaaat cgtaccatca atcttgctgt      4920
ggatgaggcg accttagctg ctcgacgtaa g                                     4951
```

<210> SEQ ID NO 15
<211> LENGTH: 15011
<212> TYPE: DNA
<213> ORGANISM: Acinetobacter sp. Tol5
<220> FEATURE:
<221> NAME/KEY: misc_feature
<222> LOCATION: (13288)..(13288)
<223> OTHER INFORMATION: n is a, c, g, or t
<220> FEATURE:
<221> NAME/KEY: misc_feature
<222> LOCATION: (13304)..(13304)
<223> OTHER INFORMATION: n is a, c, g, or t
<220> FEATURE:
<221> NAME/KEY: misc_feature
<222> LOCATION: (14163)..(14163)
<223> OTHER INFORMATION: n is a, c, g, or t

```
<400> SEQUENCE: 15
gttaacgcaa gttgttttac tgctgaagct gtcaattttt gtccacgacc tgacttacgg      60
tccggttgag tatacacagc gacgatttcg tggtcagttt gaatcagtgc tgctaatgct     120
gaagctgcaa attcgggtgt gcctgcaaaa atgatcttca aaggttgtgc tcagattaaa     180
ttttaaagtc aattatagca aacatggttc tatggtggga ttttcaaatg aaaatttgat     240
tttctccaaa tgtgaaaatt aattatatta ttttgacaca aagctattta tttatgattt     300
tgacgtatct atagatctga tatgtttctt ttgattaatg aatttgatga tattttgatc     360
gcagtatggg tgatattaaa aaataatgtg atttaaatca catttaatag actatgtttt     420
ataaaaatta gaatcatttt tcagagtatg gtttcttaca tattgaaata atgatctgtt     480
tttttgtgtt ttgtaaagtt tttctaaaca aaattaataa atattactca gaaaaacaca     540
aagtagtgaa agataaaaat aaaaagctat taagaaaaat tgtaaacaca aagaatgtaa     600
acttaataaa atataatttt gaggaatgag tcacacttat ttttaacaaa tgtgacaaaa     660
tttgtcacat aattaattag aaataatgtg attttagtaa aactttacaa tactgaggat     720
aaatataact ctatgttttt taaatgtaaa atattaaaaa tgtaaaataa tatagcttaa     780
tttcaaaaaa attaaaccaa ttggtttaaa agttaaaaaa agtgaaatat atctcatttt     840
tttgattgct ttaattgtat gtaaattgtt aaataaaaaa aattgtacat tttatatgca     900
ttgctaaagc agaacctact gcccaaaatg catctcctaa ggaaaagcga tatgaataaa     960
atctacaaag tgatttggaa tgcgactttg ttggcatggg ttgcagtatc tgaattggca    1020
aaagggaaaa ccaaatctac gacatcaaaa tccaaagcta atcattatc ttcatctgta    1080 atagttggtg ggataatatt aacaacacct ttatctttaa tagcagctac tgttcaagtt    1140 ggaggggaa ctaattctgg aacaactgct acagcttcta cgaattgtgc agacttatat    1200
aattatcaaa atcctgagaa ctcaggctct ggagcggctg ggaattataa tgcaggaaat    1260
ccaagtgtgt gttcgatcgc tataggtgaa aacgcacaag gtggtacttc tggaactgga    1320
gggtcgccag ggatagcgat aggtggaaat tctaaagcta cgggtggttt atctgttgct    1380
ataggcggat atgctcaagc gacaaatgtt ggaagtattg ctttaggcac agcagcttta    1440
tcaagtggtt ttaacagttt agcaatatcc agacaagctg ctgcaacgaa taactattca    1500
atagctatag gtacaacttc agtttcgaaa ggagttggat cgattgctat ggggcattca    1560
acgaatgctt ctggagatca atcgatagca attggtagct cggatgctgt taattcagca    1620
acagcaacaa caacatacga tggtacaaca aatactcaag catcaggtag taaatcgatt    1680
gctataggtg caagcgcaaa ggcatcaacc aataacagca ttgcactagg tgcaggatcg    1740
gtaacttctg cacaatctgg taattcttat cttactggtg taggtgcatc agctacaaat    1800
ggtgttgtat ctgttggaac ttcaactgca acacgtcgta tccaaaatgt agcagatggt    1860
tcagccgctt cagatgctgt gacagttgct cagttggata agcttatga tgatacaaat    1920 ggtcgtttag ctgctgcttt aggtacaggt agtggtgctg cctataatgc agcaaacaat    1980
acatataccg ctccaacgaa tattgggggga acaggtaaaa atacgattga tgatgcaatt    2040
aaagcaactc aacgaagtgt agtcgctgga tcaaatattg tcgttacccc gacgacagct    2100
tctgatggtt caatatcgta ttcggttgct acaagcgcaa caccgacgtt tacaagtata    2160
actgtaaaca atgcaccaac ggcaggtaca gatgcgacca acaagactta tgtagactca    2220
aaagcagcag catcgagaac agaagtagca gctggaagca atgtatctgg tgtagtaaaa    2280
acgacaggcg caaacggtca agacgtttat acagtaaatg ccaatggtac gactgcatca    2340
```

```
gcaggttctt cagcagttac cgtaacacca ggcacgaaag atgcaaataa tgtcactgac    2400
tataaagtag acttatcagc gactacaaaa accgatatcc aaaaaggtgt agatgcaaaa    2460
aatgctgtag ataccgcagg tctaaaattt aaaggtgata cagcaaccac aagcaatacc    2520
aagaaattag gtgacaccgt ttcgattacg ggtgatacga acattagtac agttgcgaca    2580
acagatggtg tacaggttaa gttaaatcca aacttggatt taggagcaac tggtagcgtt    2640
aaaacgggta ataccacgat taacaatgca ggtgtaacag ctgatcaagt tacgcttggt    2700
ggtgttgtta ttaacaacac atcaggtatt aatgctggtg gtaaagcgat tactaatgta    2760
gcagcaccaa caaataacac agatgctgct aacaagaagt atgtagatga tgcaggtaca    2820
gcattaacca atttgggctt tggattaaaa gcacaagatg gtacgactgt gaacaagaaa    2880
ttaggtgaag cagttgatat tgttggttca aacagcaaca tcagtacaaa agtaaatgca    2940
ggcaaagtag aagttgcact atccaataca ttggacttag gtactacagg tagcgttact    3000
acgggttcaa ctgtaattaa caatactggt gttacggcaa ctcaggttac cgcaaacaaa    3060
gtcacaataa acaatgcacc aacagcaggt acagatgcga ccaacaagac ttatgtagac    3120
tcaaaagcag cagcatcaag aacagaagtc gcagctggaa gcaatgtatc tggtgtagta    3180
aaaacgacag gcgcaaacgg tcaagatatt tatgcagtaa atgccaatgg tacgactgca    3240
tcagcaggtt cttcagcagt taccgtaaca ccaggcacga agatgcaaa taatgtcact    3300 gactataaag tagacttgtc agcgactaca aaaaccgata ttcaaaaagg tgtagatgca    3360
aaaaatgctg tagatactgc aggtctaaaa tttaaaggtg atacagcaac cacaagcaat    3420
accaagaaat taggtgacac cgtttcgatt acgggtgata cgaacattag tacagttgca    3480
acaactgatg gtgtacaggt taagttaaat ccaaacttag atttaggagc aactggtagc    3540
gttaaaacgg gtaataccac gattaacaat gcaggtgtaa cagctgacca agttacggtt    3600
ggtggtgttg ttattaacaa cacatcaggt attaatgctg gtggtaaagc gattaccaat    3660
gtagcagcac caacaaataa cacagatgct gctaacaaga gtatgtaga tgacgcaggt    3720 acagcattaa ccaatttggg ctttggatta aaagcgcaag atggtacgac tgtgaacaag    3780
aaattaggtg aagcagttga tattgttggt tcaaacagca acatcagtac aaaagtaaat    3840
gcaggcaaag tagaagttgc actatccaat acattggact taggtactac aggtagcgtt    3900
actacgggtt caactgtaat taacaatgct ggtgttacgg caactcaagt taccgcaaac    3960
aaagtcacag ttaataatgc accaacagca ggtacagatg cgaccaataa aacttatgta    4020
gactcaaaag cagcggcatc aagaacagaa gtcgcagctg gaagcaatgt atctggcgta    4080
gtaaaaacga caggtgcaaa cggtcaagac gtttatacag taaatgccaa tggtacgact    4140
gcatcagcag gttcttcagc agttaccgta acaccaggca cgaaagatgc aaataatgtc    4200
actgactata agtagacttg tcagcgacta caaaaaccg atattcaaaa aggtgtagat    4260
gcaaaaaatg ctgtagatac cgcaggtcta aaatttaaag gtgatacagc aaccacaagc    4320
aataccaaga aattaggtga caccgtttcg attacgggtg atacgaacat tagtacagtt    4380
gcgacaactg atggtgtaca ggttaagcta aatccaaact tggatttagg agcaactggt    4440
agcgttaaaa cgggtaatac cacgattaac aatgcaggtg taacagctga tcaagttaca    4500
gttggtggtg ttgttattaa caacacatca ggtattaatg ctggtggtaa agcgattacc    4560
aatgtagcag caccaacaaa taacacagat gctgctaaca agaagtatgt agatgatgca    4620
ggtacagcat taaccaattt gggctttgga ttaaagcgc aagatggtac gactgtgaac    4680
aagaaattag gcgaagcagt tgaagttgtt ggtgcggaca gtaacatcac cacgaaagtt    4740
```

```
gcaggcggtc aggttgcaat tgagttaaat aaaaacctca acaacttaac tggcattacc    4800
gtgaacgatg gaaccaatgg caccaatggt tcaactgtga ttggtaaaga tggtatttcg    4860
gttaaagatg gttcaggcaa taccattgca ggtgtagata cacagcgtt gacagttaaa     4920 gatggcagtg gcaacacaga aaccagcatt aaccaagcga tcaacacgtt aaatgcagcg    4980
caaggtgaaa ctgataagtt tgcagtgaag tacgacaaaa atgctgatgg cagtgtgaac    5040
tacaacaaca tcacattggc aggtacgact gcaagcagta cacaagatgc aactacaggc    5100
aagatcacca acacaggtgg aacaagcttg aacaatgttg caagtgcggg tgactacaaa    5160
gatgttgcca atgcaagcaa aggtgtaaac gcaggtgact aaacaatgc agttgttgat     5220 gcaaccaatg cagcaaccag caaaggcttt gcattacaag cagcagatgg cgctaaagtt    5280
cagaagaacc taggcgaagc agttgaagtt gtcggtgccg acagcaacat caccacaaaa    5340
gttgcaggcg gtcaggttgc aattgagtta ataaaaaacc tcaacaactt aactggcatt    5400
accgtgaacg atggaaccaa tggcaccaat ggttcaactg tgattggtaa agatggtatt    5460
tcagttaaag acggttcagg caataccatt gcaggtgtag ataacacagc gttgacagtt    5520
aaagatggca gtggcaacac agaaaccagc attaaccaag cgatcaacac gttaaatgca    5580
gcgcaaggtg aaactgataa gtttgcagtg aagtacgaca aaaatacgga tggtagtacc    5640
aactacaaca gtattactgc aggcaatggt aacggtactg cagcaacgat cggaactgac    5700
acagcaggta atagtgttgt gaccagtggc ggaactaaaa ttagtaatgt tgcgaatggt    5760
gtcaatgcaa gtgatgcagt aaacaaaggt caattggata gcttaagtac aggtcttacc    5820
aatacaggct ttggtttaaa agcagcagat ggcaacaccg ttaacaaaaa attaggcgaa    5880
gcagtagacg ttgtcggtgc tgacagcaac atcaccacga agttgcagg cggtcaggtt     5940 gcgattgagt aaataaaaaa cctcaacaac ttaactggca ttaccgtgaa cgatggaacc    6000
aatggcacca atggttcaac tgtgattggt aaagatggta tttcgattaa agatggttca    6060
ggcaatacca ttgcaggtgt agataacaca gcgttgacag ttaaagatgg cagtggcaac    6120
acagaaacca gcattaacca agcgatcaac acgttaaatg cagcgcaagg tgaaactgac    6180
aagtttgcag tgaagtacga caagaatgct gatggcagtg caaactacaa caacatcaca    6240
ttggcaggta cgactgcaag tagcacgcaa gatgcaacaa caggcaagat caccacaaca    6300
ggtggaacaa gcttgaacaa cgttgcaagt gcaggtgact acaaagatgt tgccaatgca    6360
agcaaaggtg taaacgcagg tgacttgaac aatgcagttg ttgatgcaac caatgcagca    6420
accagcaaag ctttgcatt acaagcagca gatggcgcta aagttcagaa gaacctaggc    6480
gaagcagttg aagttgtcgg tgcggacagc aacatcacca caaaagtagt gggtggacaa    6540
gttgcgattg agttaaataa aaaccctcaac aacttaactg gcattaccgt gaacgatgga    6600
accaatggca caatggttc aactgtgatt ggtaaagatg gtatttcggt taaagatggt     6660
tcaggtaata ccattgcagg tgtagataac acagcgttga cagttaaaga tggcagtggc    6720
aacacagaaa ccagcattaa ccaagcgatc aacacgttaa atgcagcgca aggtgaaact    6780
gataagtttg cagtgaagta cgacaaaaat gctgatggca gtgtgaacta caacaacatc    6840
acattggcag gtacgactgc aagcagtaca caagatgcaa ctacaggcaa gatcaccaca    6900
acaggtggaa caagcttgaa caatgttgca agtgcgggtg actacaaaga tgttgccaat    6960
gcaagcaaag gtgtaaacgc aggtgactta acaatgcag ttgttgatgc aaccaatgca     7020
gcaaccagca aaggctttgc attacaagca gcagatggcg ctaaagttca gaagaaccta    7080
ggcgaagcag ttgaagttgt cggtgccgac agcaacatca ccacaaaagt tgcaggcggt    7140
```

```
caggttgcaa ttgagttaaa taaaaacctc aacaacttaa ctggcattac cgtgaacgat    7200
ggaaccaatg gcaccaatgg ttcaactgtg attggtaaag atggtatttc agttaaagac    7260
ggttcaggca ataccattgc aggtgtagat aacacagcgt tgacagttaa agatggcagt    7320
ggcaacacag aaaccagcat taaccaagcg atcaacacgt taaatgcagc gcaaggtgaa    7380
actgataagt ttgcagtgaa gtacgacaaa aatgctgatg gcagtgtgaa ctacaacaac    7440
atcacattgg caggtacgac tgcaagcagt acacaagatg caactacagg caagatcacc    7500
acaacaggtg gtacaagctt gaacaatgtt gcaagtgcgg gtgactacaa agatgttgcc    7560
aatgcaagca aaggtgtaaa cgcaggtgac ttgaacaatg cagttgttga tgcaaccaat    7620
gcagcgacca gcaaaggctt tgcattacaa gcagcagatg gcgctaaagt tcagaagaac    7680
ctaggcgaag cagttgaagt tgttggtgcg gacagtaaca tcaccacgaa agttgcaggc    7740
ggtcaggttg caattgagtt aaataaaaac ctcaacaact taactggcat taccgtgaac    7800
gatggaacca atggcaccaa tggttcaact gtgattggta agatggtat ttcggttaaa    7860 gatggttcag gcaataccat tgcaggtgta gataacacag cgttgacagt taaagatggc    7920
agtggcaaca cagaaaccag cattaaccaa gcgatcaaca cgttaaatgc agcgcaaggt    7980
gaaactgata agtttgcagt gaagtacgac aaaaatgctg atggcagtgc aaactataac    8040
aatgtcactt tagctggtac aaatggcaca ataatcagca atgttaaagc gggtgctgtg    8100
acctcaacat ctactgatgc gatcaatggt agccaattat atggtgttgc aaacagcgtg    8160
aagaatgcaa ttggtggttc aaccacaatt gatgcaacga ctggtgcaat cacgacgacc    8220
aatattggtg gtacaggttc aaatacgatt gatggtgcaa tcagcagtat aaagattca    8280 gcgactaaag cgaaaaccac ggtaagtgct ggggataatg ttgtcgttac atcgggtacc    8340
aatgcagatg gctcaacaaa ctatgaagtt gcgacagcga aagacgttaa ctttgacaaa    8400
gtgactgtag gtagtgttgt tgtagataaa tcaagcaata caatcaaagg attaagtaat    8460
accacttgga acggaacagc agtatcaggt caagcggcga cagaagacca gttaaaaacg    8520
gtcagcgatg cgcaaggtga aactgataag tttgcagtga agtacgacaa aaatgctgat    8580
ggcagtgcga actacaacag tattactgca ggcaatggta acggtactgc agcaacgatc    8640
ggaactgaca cagcaggtaa tagtgttgtg accagtggcg gaactaaaat tagtaatgtt    8700
gcgaatggtg tcaatgcaag tgatgcagta aacaaaggtc aattggatag cttaagtaca    8760
ggtcttacca atacaggctt tggtttaaaa gcagcagatg gcaacaccgt taacaaaaaa    8820
ttaggcgaag cagtagacgt tgtcggtgct gacagcaaca tcaccacgaa agttgcaggc    8880
ggtcaggttg cgattgagtt aaataaaaac ctcaacaact taactggcat taccgtgaac    8940
gatggaacca atggcaccaa tggttcaact gtgattggta agatggtat ttcgattaaa    9000 gatggttcag gcaataccat tgcaggtgta gataacacag cgttgacggt taaagatagc    9060
agtggcaaca cagaaaccag cattaaccaa gcgatcaaca cgttaaatgc agcgcaaggt    9120
gaaactgata agtttgcagt gaagtacgat aagaatgctg atggcagtgt gaactataac    9180
aatgtcactt tagcaggtac aaatggcaca ataatcagaa atgttaaagc gggtgctgtg    9240
acctcaacat ctactgatgc gatcaatggt agccaattat acgatattgc aaacagcgtg    9300
aagaatgcaa ttggtggttc aaccacaaga gatgtaacga ctggtgcaat cacaacgacc    9360
aatattggtg gtacaggttc aaacacgatt gatggtgcaa tcagcagtat aaagattca    9420 gcgactaaag cgaaaaccac gataagtgct ggggataatg ttgtcgttac atcgggtacc    9480
aatgcagatg gctcaacaaa ctatgaagtt gcgacagcga aagacgttaa ctttgacaaa    9540
```

```
gtaactgtag gtaatgttgt tgttgataag gcaaatgaca cgatccaagg tttgagcaat   9600
aaagatctaa attcaactga ttttgcgacc aaaggtagag ctgcgactga agaacagtta   9660
aaagcagtga ttaccagtaa tatcacggaa gttgtggatg gtaatggcaa caaggtgaat   9720
attattgacc aagttgtaaa taccaaacct gacaataaga accaagattc attgttctta   9780
acgtatgaca acaaggtca agaaaccaca gatcgcctaa cgattggtca acggtacag    9840 aagatgaata ctgatggtat taaattcttc cataccaatg ccgatacatc aaaaggtgat   9900
ttgggtacaa caaatgactc aagtgcaggt ggtttaaact ctacagcaat tggtgtaaat   9960
gcgattgttg cgaatggtgc agatagttca gttgctttag gtcataacac caaagtcaat  10020
ggtaaacaat caattgcaat tggttctggt gcagaagctt taggcaatca atcgatcagt  10080
attggtacag gcaataaagt cactggtgat cattcgggtg cgattggtga tccaactatt  10140
gtaaatggtg caaacagcta ctctgtgggt aataacaacc aagtacttac agatgacact  10200
ttcgtacttg gaaacaatgt caccaaaact attgctggtt cagtagtatt gggtaacggt  10260
tcagctgcaa cgacaggtgc tggtgaggca ggctatgcct tatctgtagc aacaaatgca  10320
gataaagccg cgatcactaa aactacgtca agcactggtg ctgttgcagt tggtgatgcg  10380
tcgagcggta tttatcgtca aattaccggt gttgctgcgg gtagcgtaga ttcagatgct  10440
gtgaacgttg cacagttaaa agcggtgggt aaccaagttg taacgactca aactacattg  10500
gtgaacagtt tgggtggtaa cgctaaagta aatgcagacg gtacgattac aggaccaact  10560
tataatgttg ctcaaggtaa tcagaccaat gttggtgatg cattaactgc gcttgataac  10620
gcaattaata ctgcggcaac aacatctaaa tcgactgttt ctaatggtca gaatattgtt  10680
gtcagcaaga gcaaaaatgc agatggttca gacaactatg aagtatcaac agcaaaagac  10740
ttgacagttg attctgtcaa agcgggtgat acggttctga ataatgcagg tattacaatt  10800
ggcaataacg cagttgtatt gaacaacact ggattaacca ttagtggtgg accaagtgtt  10860
accttggcag gcatcgatgc aggcaataaa accattcaaa atgttgcgaa tgcagtaaat  10920
gcaacagatg cagtcaacaa agggcaattg gacagcgcaa ttaacaatgt gaataacaat  10980
gtaaatgagc ttgccaacaa cgctgttaaa tatgacgatg catcaaaaga taagatcaca  11040
cttggtggtg gggcaactgg tacaacaatc accaatgtga agatggtac tgttgcgcaa   11100 ggttctaaag atgctgtgaa tggcggtcaa ttgtggaatt ttcaacaaca agttgatcag  11160
aacacaactg atattagcaa tatcaaaaat gatattaaca acggtactgt tggtttggtt  11220
caacaagcag gtaaagatgc accagtgacg gttgcaaaag atactggcgg tacaacggtg  11280
aatgtcgctg gaacagatgg caaccgagta gtgacaggtg ttaaggaagg tgcagtgaat  11340
gcaacatcta aagatgctgt caatggtagt caattgaata caaccaacca agcggtagtc  11400
aattatcttg gtggtgggc aggttatgac aacattacag gtagcttcac agcgccaagt  11460
tatacggtag gtgactcgaa atacaacaat gttggtggcg caattgatgc attgaatcaa  11520
gcagatcaag cattgaatag caaaattgac aatgtcagta acaagttgga taacgcattc  11580
cgtattacca caaccgtat tgatgatgta gagaaaaaag ccaatgctgg tattgccgct   11640
gcgatggctc tggaatcagc accatatgtc ccaggtaaat atacctatgc agcaggcgca  11700
gcttaccacg gtggtgaaaa tgcggtaggt gtgactttac gtaaaactgc agacaatggt  11760
cgttggtcga ttacaggcgg tgtagctgca gcgtctcaag gcgatgcaag tgttcgtatc  11820
ggtatcagcg gtgtgattga ctaattcact cgacagggaa gatcttcggg tcttcctttt  11880
tcttcgaaaa tttttttaaga gagaaaaaat gaaagcattt aacaaaaaaa ttatgtttgg  11940
```

```
tgtattcagc ggtcttgtga tgtcattgag ccatgctgct gaagtcgaaa gtgcaaatac  12000
gcaagaaatc cattttcctg aaatcaaaga cagctattta aaacaagtga accgttatga  12060
atatgacgat gtcgcacgtt tagacaaggg attaaccaaa gatcagattc gccatatttt  12120
gggaaatcct caattctctg aaggtctttt tgcggttaag acatggaatt atgtattgga  12180
tattcgtgag cctaactcaa accaatataa gcgttgccaa ttacgcatag attttgataa  12240
gcaataccgt tcagacaatc tatattggaa aggtgaacaa tgccaaggct taatggcttg  12300
ggggattaat aatcagtctg agactgagca aacgactcta gcacctggtg gcagtctgc   12360 aagtgttttg ttttatttg atcatgcgga taaaaatggt gtaaagaacg ctgaagtgat   12420
tcgtaaaatc gcagatcaga ttaaacaatc tgatgcgaat agccctgttt tgtggctgg   12480 atatactgat cgtttaggat catttcagta taaccaacgt ttatctgccc aaagagcgaa  12540
tacagtcgtt gaactcttga agcaacaagg cattcgtggc gagcaaattc agtacagtgc  12600
tgaaaataaa acagatgtgt accaaaagtg cgcagggatc aataaaaaga tccaactggt  12660
tgaatgtcta gcacctaacc gtcgtgtgaa tatcacgtgg taagtcttat ttattcaatc  12720
taattttgga taatccaaac aaaaaacgat atgtgttcca cattatcgtt ttttgttttt   12780
tgagcaggtg ttgattaaaa aatcaaggag ctgatgagat tgcaaaaatt tccaattaat  12840
ttaaaacaat aaagtacgca aatgatgaaa aaacagttgt gttaatgatt ggcttggggt  12900
ttacctttct ggcacaagca tttgataaaa aagtaatgat atttcgatta tcaatatttg  12960
agcttctatg aatagagatc ttttataaaa ttaaatttag tgattattgt taaatgataa  13020
atattattta ttaaaaaata aaaaattatt catgaagtt  ttgtgtctaa tctggcgtgt  13080
tagcgttata ttaaatatca atattcattt atctctaaac cctgttgaaa tataagtaaa  13140
cacgtcttgt ttaaaaaaag atcatactca aggtcattgg ttctacgtta acttatagta  13200
tgatgtgtac atatttcgac tgatttattg ctatatcagt tttatttagc cagagtgaat  13260
ctgattcatt tcaagctcaa acaatgtngg aaatacaaat gccngactat cgttcaaaaa  13320
catcgacaca tggaagaaat atggctggtg cacgtggctt atggcgtgca acaggaatga  13380
aagatgaaga tttcggtaag ccgattattg cggtagtcaa ctcatttacc cagtttgtgc  13440
ctggtcatgt ccaccttaaa gatttaggtc aactggttgc ggaacaaatc caagcagctg  13500
gtggtgtggc aaaagaattt aataccattg ccgtggatga tggtatcgca atggggcatg  13560
atggcatgct gtattcattg ccttcacgtg atttgattgc agactctgtc gaatatatgg  13620
tcaatgcaca ctgcgcagat gccatggtgt gtatttcaaa ctgtgacaaa attaccccag  13680
ggatgttaat ggcagcgatg cgcttaaaca ttccagtggt gtttgtgtcg ggtggaccaa  13740
tggaagcggg taaagttaaa atccgtggta cagaacgtgc aattgactta gttgatgcga  13800
tggtggttgc agccgatgat aattttacag atgaagaagt aaaagaatac gagcgttcag  13860
catgcccaac atgtggttca tgttcaggta tgttcacagc aaattcgatg aactgtttga  13920
cagaagcatt ggggttgtcg ttaccaggaa atggttcaac attagcaacg catgctaacc  13980
gtaagaaact attcgaaaaa gcaggtcaat tggttgttga attggcaaaa cgccattatg  14040
aacaagatga ttacacggta ttaccacgtt cgatcgcaac caaagcatct tatgaaaatg  14100
ccatgacgct cgatattgcg atgggtggtt caaccaatac cgtattgcat ttattggctg  14160
ctnccagtga agcaggtgtt gactttacca tggatgacat tgatcgttta tcgcgtaaag  14220
tgcctgtatt atgtaaagtt gctcctgcaa agcaggatgt gcatatggaa gatgtgcatc  14280
gtgccggtgg catcatgtcc attctcggtg aattggatcg tgcaggttta ttagatacat  14340
```

```
cggtacacac tgtgcatgag cacaccttaa aagatgcatt ggataaatgg gatattattc    14400
gtacagaaga cccagtggta tatgagttct tccgctcagc gccaggtggt gttccaactc    14460
aaacagcatt ctcacaaaat cgctattacc agactttgga tggcaatcgt gaaacaggtg    14520
tgattcgtaa tgctgaacat gctttctcta aagatggtgg cttggcagta ttgtatggca    14580
acattgctgt agatgggtgt attgttaaaa cagcaggtgt tgatgattca attttaaaat    14640
ttaatggaac tgcacgagta tttgaaagcc aagatgctgc agtagattca attttaggac    14700
atgaaattaa ggctggtgat gtggttgtga tccgttatga aggaccacgt ggtggaccgg    14760
gtatgcagga aatgctttat ccgaccagtt atttaaaatc aaaaggctta ggtaaagaat    14820
gtgctttact gacagatgga cgtttctctg gaggttcttc tggcctttca attggtcatg    14880
tatcacctga agctgctgaa ggtggtgtga ttggattggt tgaagatggt gatttgattg    14940
aaattgatat tccaaatcgt accatcaatc ttgctgtgga tgaggcgacc ttagctgctc    15000
gacgtaagct t                                                         15011
```

<210> SEQ ID NO 16
<211> LENGTH: 33
<212> TYPE: DNA
<213> ORGANISM: Artificial Sequence
<220> FEATURE:
<223> OTHER INFORMATION: synthetic DNA

<400> SEQUENCE: 16
gtcgactaaa cgaccatttg tatcatcata agc                                  33

<210> SEQ ID NO 17
<211> LENGTH: 27
<212> TYPE: DNA
<213> ORGANISM: Artificial Sequence
<220> FEATURE:
<223> OTHER INFORMATION: synthetic DNA

<400> SEQUENCE: 17
taaacgacca tttgtatcat cataagc                                         27

<210> SEQ ID NO 18
<211> LENGTH: 29
<212> TYPE: DNA
<213> ORGANISM: Artificial Sequence
<220> FEATURE:
<223> OTHER INFORMATION: synthetic DNA

<400> SEQUENCE: 18
gtcgacggta caggtagtgg tgctgccta                                       29

<210> SEQ ID NO 19
<211> LENGTH: 23
<212> TYPE: DNA
<213> ORGANISM: Artificial Sequence
<220> FEATURE:
<223> OTHER INFORMATION: synthetic DNA

<400> SEQUENCE: 19
ggtacaggta gtggtgctgc cta                                             23

<210> SEQ ID NO 20
<211> LENGTH: 26
<212> TYPE: DNA
<213> ORGANISM: Artificial Sequence
<220> FEATURE:
<223> OTHER INFORMATION: synthetic DNA -continued

<400> SEQUENCE: 20
aatttcaaaa aaattaaacc aattgg                                        26

<210> SEQ ID NO 21
<211> LENGTH: 25
<212> TYPE: DNA
<213> ORGANISM: Artificial Sequence
<220> FEATURE:
<223> OTHER INFORMATION: synthetic DNA

<400> SEQUENCE: 21
gttaaatgct ttcatttttt ctctc                                         25

<210> SEQ ID NO 22
<211> LENGTH: 20
<212> TYPE: DNA
<213> ORGANISM: Artificial Sequence
<220> FEATURE:
<223> OTHER INFORMATION: synthetic DNA

<400> SEQUENCE: 22
cacgaaagtt gcaggcggtc                                               20

<210> SEQ ID NO 23
<211> LENGTH: 21
<212> TYPE: DNA
<213> ORGANISM: Artificial Sequence
<220> FEATURE:
<223> OTHER INFORMATION: synthetic DNA

<400> SEQUENCE: 23
acaatgttgc aagtgcgggt g                                             21

<210> SEQ ID NO 24
<211> LENGTH: 21
<212> TYPE: DNA
<213> ORGANISM: Artificial Sequence
<220> FEATURE:
<223> OTHER INFORMATION: synthetic DNA

<400> SEQUENCE: 24
tgcaatggta ttgcctgaac c                                             21

<210> SEQ ID NO 25
<211> LENGTH: 22
<212> TYPE: DNA
<213> ORGANISM: Artificial Sequence
<220> FEATURE:
<223> OTHER INFORMATION: synthetic DNA

<400> SEQUENCE: 25
gttcttctga actttagcgc ca                                            22

<210> SEQ ID NO 26
<211> LENGTH: 24
<212> TYPE: DNA
<213> ORGANISM: Artificial Sequence
<220> FEATURE:
<223> OTHER INFORMATION: synthetic DNA

<400> SEQUENCE: 26
tgtttgagct tgaaatgaat caga                                          24

<210> SEQ ID NO 27
<211> LENGTH: 22
<212> TYPE: DNA

```
<213> ORGANISM: Artificial Sequence
<220> FEATURE:
<223> OTHER INFORMATION: synthetic DNA

<400> SEQUENCE: 27
caggaaacag ctatgaccat ga                                              22

<210> SEQ ID NO 28
<211> LENGTH: 21
<212> TYPE: DNA
<213> ORGANISM: Acinetobacter sp. Tol5

<400> SEQUENCE: 28
gttttcccag tcacgacgtt g                                               21

<210> SEQ ID NO 29
<211> LENGTH: 106
<212> TYPE: DNA
<213> ORGANISM: Acinetobacter sp. Tol5

<400> SEQUENCE: 29
ttgctttaat tgtatgtaaa ttgttaaata aaaaaaattg tacattttat atgcattgct     60
aaagcagaac ctactgccca aaatgcatct cctaaggaaa agcgat                    106
```